(12) United States Patent
Issa et al.

(10) Patent No.: US 8,133,986 B2
(45) Date of Patent: Mar. 13, 2012

(54) METHYLATED CPG ISLAND AMPLIFICATION (MCA)

(75) Inventors: Jean-Pierre Issa, Timonium, MD (US); Stephen Baylin, Baltimore, MD (US); Minoru Toyota, Baltimore, MD (US)

(73) Assignee: The Johns Hopkins University School of Medicine, Baltimore, MD (US)

(*) Notice: Subject to any disclaimer, the term of this patent is extended or adjusted under 35 U.S.C. 154(b) by 0 days.

(21) Appl. No.: 12/763,917

(22) Filed: Apr. 20, 2010

(65) Prior Publication Data
US 2011/0020807 A1    Jan. 27, 2011

Related U.S. Application Data

(62) Division of application No. 09/309,175, filed on May 10, 1999, now Pat. No. 7,700,324.

(60) Provisional application No. 60/106,925, filed on Nov. 3, 1998.

(51) Int. Cl.
*C07H 21/02* (2006.01)
*C07H 21/04* (2006.01)
*C12P 19/34* (2006.01)
*C12N 1/20* (2006.01)
*C12N 15/00* (2006.01)

(52) U.S. Cl. ............... 536/23.1; 536/24.3; 536/24.33; 435/91.1; 435/252.3; 435/320.1

(58) Field of Classification Search .......... 435/6, 91.1, 435/91.2, 183, 253.2, 320.1; 436/94, 501; 536/23.1, 24.3, 24.33, 25.3
See application file for complete search history.

(56) References Cited

U.S. PATENT DOCUMENTS

| | | | |
|---|---|---|---|
| 5,296,371 A * | 3/1994 | Razin et al. ............ | 435/252.3 |
| 5,501,964 A | 3/1996 | Wigler et al. | |
| 5,786,146 A | 7/1998 | Herman et al. | |
| 5,912,147 A | 6/1999 | Stoler et al. | |
| 6,015,711 A * | 1/2000 | Olson et al. ............ | 435/375 |
| 6,017,704 A | 1/2000 | Herman et al. | |

FOREIGN PATENT DOCUMENTS

| | | |
|---|---|---|
| WO | WO 96/35704 | 11/1996 |
| WO | WO 97/45560 | 12/1997 |

OTHER PUBLICATIONS

Dobnor et al., Human HALPHA44 gene for alpha-tubulin, exons 1-3. Nucleic Acids Research, 15, 199-218, 1987.*

(Continued)

*Primary Examiner* — Frank W Lu
(74) *Attorney, Agent, or Firm* — DLA Piper LLP (US)

(57) ABSTRACT

The present invention provides a method for identifying a methylated CpG containing nucleic acid by contacting a nucleic acid with a methylation sensitive restriction endonuclease that cleaves unmethylated PcG sites and contacting the sample with an isoschizomer of the methylation sensitive restriction endonuclease, which cleaves both methylated and unmethylated CpG sites. The method also includes amplification of the CpG-containing nucleic acid using CpG-specific oligonucleotide primers. A method is also provided for detecting an age associated disorder by identification of a methylated CpG containing nucleic acid. A method is further provided for evaluating the responses of a cell to an agent. A kit is useful for detection of a CpG containing nucleic acid is also provided. Nucleic acid sequences encoding novel methylated clones.

15 Claims, 14 Drawing Sheets

OTHER PUBLICATIONS

Kochanek et al., "DNA Methylation in the Alu Sequences of Diploid and Haploid Primary Human Cells," *The EMBO Journal* (1993), 12(3):1141-1151, Oxford University Press.

Kohno et al., "Identification of CpG Islands Hypermethylated in Human Lung Cancer by the Arbitrarily Primed-PCR Method," *Hum. Genet.* (1998), 102:258-264, Springer-Verlag.

Lisitsyn et al., "Cloning the Differences Between Two Complex Genomes," *Science* (1993), 259:946-951.

Merlo and Herman, "DNA Methylation and Inactivation of Tumor Suppressor Genes," In Muller et al. (ed.), *Hereditary Cancer, Second International Research Conference on Familial Cancer* (1996), 152-160, S. Karger AG.

Sulewska et al., "DNA Methylation in States of Cell Physiology and Pathology," *Folia Histochemica et Cytobiologica* (2007) 45(3):149-158.

Toyota and Issa, "CpG Island Methylator Phenotypes in Aging and Cancer," *Cancer Biology* (1999), 9:349-357, Academic Press.

Toyota et al., "Identification of Differentially Methylated Sequences in Colorectal Cancer by Methylated CpG Island Amplification," *Cancer Research* (1999), 59:2307-2312.

Ushijima et al., "Establishment of Methylation-Sensitive-Representational Difference Analysis and Isolation of Hypo- and Hypermethylated Genomic Fragments in mouse Liver Tumors," *Proc. Natl. Acad. Sci. USA* (1997), 94:2284-2289, The National Academy of Sciences of the USA.

West et al., "Hypomethylation of the Amyloid Precursor Protein Gene in the Brain of an Alzheimer's Disease Patient," *Journal of Molecular Neuroscience* (1995), 6:141-146, Humana Press Inc.

Zrihan-Licht et al., "DNA Methylation Status of the *MUC1* Gene Coding for a Breast-Cancer-Associated Protein," *Int. J. Cancer.* (1995), 62:245-251, Wiley-Liss, Inc.

\* cited by examiner

FIG. 4B

| | | | | | | | | | | | |
|---|---|---|---|---|---|---|---|---|---|---|---|
| D | 80 | | | | | | | | | | Negative |
| | 473 | | ■ | | | | | | | | Negative |
| | 98 | | | | | | | | | | Negative |
| | 92 | | | | | | | | | | Negative |
| | 836 | | | | | | | | | | Negative |
| | 546 | ■ | | | | | | | | | Negative |
| | 1290 | | | | | | | | | | Negative |
| | 833 | | | | | | | | | | Negative |
| | 872 | | | | | | | | | | Negative |
| | 835 | | | | | | | | | | Negative |
| | 146 | ■ | | | | | | | | | Negative |
| | 108 | | | | | | | | | | Negative |
| | 256 | | ■ | | | | | | | | Negative |
| | 281 | | | | | | | | | | Negative |
| | 300 | | | | | | | | | | Negative |
| | 327 | | | | | | ■ | | | | Negative |
| | 1225 | | | | | | | | | | Negative |

| | | | | | | | | | | | |
|---|---|---|---|---|---|---|---|---|---|---|---|
| E | 373 | ■ | ■ | □ | ■ | ■ | ■ | ■ | ■ | | N.D. |
| | 91 | ■ | ■ | ▦ | ■ | □ | ■ | ■ | □ | | N.D. |
| | 236 | ■ | ■ | ■ | □ | ■ | ■ | □ | ■ | | N.D. |
| | 1292 | ■ | ■ | □ | ■ | □ | ▦ | ■ | | | N.D. |
| | 351 | ■ | ■ | ■ | ■ | □ | ■ | ■ | ■ | | N.D. |
| | 1274 | ■ | ■ | ▦ | ■ | □ | ▦ | ■ | | | N.D. |
| | 1320 | □ | ■ | | | ■ | | ■ | | | N.D. |

| | | | | | | | | | | | |
|---|---|---|---|---|---|---|---|---|---|---|---|
| F | 473 | | | | | | | | | | N.D. |
| | 391 | | | | | | | | | | N.D. |
| | 289 | | | | | | | | | | N.D. |
| | 303 | | | | | | | ▦ | | | N.D. |
| | 733 | | | | | | | | | | N.D. |
| | 427 | | | | | | | | | | N.D. |
| | 535 | | | | | | | | | | N.D. |
| | 363 | | | | | | | | | | N.D. |

MINT1 (SEQ ID NO:1)
CCCGGGCTGG GTACCTGGAC CTATACCTTC ATAGCTGCCT TAGGCTCAAC TTTTCGGCGG
GGATCCCTCT GCAGACGTGC AGGTGGCGGG AGAGCAGAGG TAGCCGCAGT AAGTGCTGAG
AGAGCCTGAA AGAAACACCA TGAATTTTCA AACTCTCCCA CATACATTCC CGAAGCGCCT
GTCTGGCGTC TAAGAGAGAG CAAGAGAGGG CTGGAGAGCA GGGGAGCCCG CGGGGCTGAG
GCTCTTTGTC AGCGCCTGCA CTTCCTACGT TACAACGCCT TCATTCAGCA AAAACCTTTT
GGGCGCCTGC TGTGCGCCAG GCCAGGCGAA GNAGACCGAG GNTGTGAAGC TCAGAGGGGA
GAGGGACCAA TCGCAGTAAA TAAGCTACCG AGGTAATCTT AGATGGNGAT GAGGGCAGGA
AAAGNCATCA GNCGACCTCT GACCTTTCTC TTAGGGGGTT TTCCCCTTCC GCCTGGGTTC
TAGAACTGGG AAGANTTTTC TCCAGAGCGT CGCGGGGAGC GCCCCGGG

MINT2 (SEQ ID NO:2)
CCCGGGCGCT GCCAAATGTA AACAATCCGC CATGATTTCT TTGTTTAGCT AATCGAACCT
GCCGCCGTCT CGAGTCCCAG GCGCTCCCTC TCCCTTCTCT CCCCTTCCCC CCTCGCGCTC
TCTTTTATTT ATTTATTTGT CTCTCCCCCC ACCCCGCCCT TAGTCTTTCC CTCTCTTTAG
TCTTAGTAGC TGCTTTTAAT GGAAGTCGAG GCAGTTGGGT AGTTGGTGCA GGGAGTGCGG
TGGTGGTTTT TATAAATACA GGTAAAATAA TACCCAAATT TCAGGCTGAG GTGCAGTTTC
TTGAAGAGG AGGAGGGTGT TCCTCTCCTT CCCTCCCTCT TTCCCCCTCC CCCGTTTATT
AGAGTATCCT CGGTGGAAAG TGCCAGAAAA ATGTGCTGCA TCTCTGAGTC ACCTTTTCTT
CCCGCCGAAC TCTAGCACCC AAGTTCGCTG GCGGATTTTG GACTCTGCCA AAGTGCTGAG
TTCGTCGTTT ACTTTGAAAG CCTGAAATAT AACTGATGTC CAACTGCAGA AAGGCGCACG
GAATCGCCGC CACCATCCCG GG

MINT3 (SEQ ID NO:3)
CCCGGGTTTC CAGCTTCTCC CTTCCACCTT TGTCTCCCCT CCCTCCTACA AACTTTCAGC
CTTCAGTCTG TTGGGGGNTA AGATCTGGGA AATAAGCGTG TGTGTCCGAG TGCCTTAGGG
TCTGCTGTGA GCCTGAATGC GAGTCCGGTT GGTTGTGCAG TTATGAACCT GTGTGTACAT
CTGTGTGCCT AAGACGCTGG GCAACTGTAC CCACATGACC GATGTGTGTG AACGACTGTG
TGCCTGTGTG TCTGGATCTG CGCGTGGGTG TAGTTCGTGT GGCTGTGTAA ACCGCATGCA
TAGGTATACA TGTACCTATG TCTCAGGCTG TGTGCGTCCT ACTGCGATGG TACGAGAGTG
TGGGTGTGAT GGTGTATGTG ATCCTGTGTC TGCGTGTCCG TACATTTGAG TGGGTGTTGT
GCGTGTGACT GTGTAAACTG CGAACATGTA CGTGTGCCCG CCCGTAGGTA TTACCGTGTA
CGTGTGTCTC CGTGTGCCTG TGAGGGGTGG GGTCTGCGCG GGGATTCCCG ACCCCCCCAC
ACTCACACCC TCCAAGCCCC GGG

MINT4 (SEQ ID NO:4)
CCCGGGCCTC TGGCCCTCTG CGTCTGCTAG NCTCTTTCCC CCAAGACTCC CCGAGGTGGG
GAGAGNACTG GTGNTCCCTG GAGAAATCAA GGTGTCCAAC ATTCTCTCCG AGGCGAGGCT
GCTTGAGCGC CAGCAACAGG NCCTGCTGAA CTTTCTTCCC CGGCTCCTAC GCTCCGGTTG
CTCTCCATCC TCATTTCTGG GGTCAAATGG NAAAGAGGGA ATACTCCTCG ACCCCTCTCC
CCCTTGACTA TCCAAAGCAG CCCGAAGTTG GCGAGGAGAC TCTGCCGGGT GTNCGGGCAA
ATGNCCCGCC GGGTGGCTCC AGAAATGGNC TGTGANCTGC ACTCGCCTCG GAGAAATTCC
AACTCTTGGT TGAAGACTCT GACTCAGAGG AGCCCTCTGA GGATGCGCCC CTGGAGAAAG
NGCACGGGAG GGAAAGTGGA GAGAACTCGN CCTCCCAGG GGCTAGNCAG CTACTCCCGG
G

FIG. 6A

MINT5 (SEQ ID NO:5)
```
CCCGGGTAAG TGAGCCCTGC TGCACTCCCG CACCCCTCTT CCCCATGCCC
ACCCTCCGGG GATGCAACAC CCTGTTCCCA TGGAACACGG GGGTTGGCAG
TCACACTGTC CCCACCCAGC TTCAGGCTTG GTCTCCTCTA GGTTTGCCTT
CTGAGGAAGC AGTCCCAGGG CATTTACTGA CCAANCAGAA AACAGGGGTT
GGGAAAAGTG AGTAGGTGGG TCTGCAACCG TTACAATCAC ATCACTTTAT
TCTTAATTCG AGTATATAAG GATTGGCATC ATANTGGGAT GANGAAGGTT
ACTGTCCTTG TCATTTGGGC AAAAGACCCC TACCCATATC TCAATGACCA
ATTCCTCANA AGTGTCCTCT TGGAANAANC TGANTTTTCC CCTCCGTAAN
TCCTTAACAC TCTCCGGCTT CCCCTCAATC CCAGGCCTTC CCCCTATTGA
CCTCAAGACC TCCTTTAATC CCAAAGAGNC GTTGACTTCC NCCAAATGCG
GGTGCTTTCC TTTCCAATCA AGAATATGTT TAAAAACCCT CCCAGGGAGT
ATGGACTATG TCCCCAATTT TAAAAGATGG AGGAACAAAG GCCCATTGGT
ATGCTAAAAA CCATGGGAAC AGGATCCAGA TTTCCCCCCA TCAATTCGAN
CTGCCAGTCT GTCCTCGGAG ATCCTTTGAC TTCTTGGAAT ANCCTTTTTG
TGTTGTGGTT TGGGGGTTGA TCTTGGAGAA CTTTTTTGTG TGTCTTTTAA
AAAATGTTTC ATTNGTTAAC TTTCCAAGTG ATGCTCTGAT TGGAGCAATC
TCAACACCAA GAAGAGTAGG GAAAGAAGCA GCGGNGGTCC TGGGTCCCCG
GG
```

MINT6 (SEQ ID NO:6)
```
CCCGGGCCCT CAGAGGCCGC ACCACCTATT GTGTTCCAGG CTCGCAGGAA GCCAGACCTT
GCGAGAGGTG TGTGGGGGCG GAGAGTGGCA CAGGTTTGAC ACTGCAGGTC GGAGGAGGAA
GACAGTGGCT GCAAAGGCAA AATCGGGTGT TATTTTCCCA AGAGTCCCTT CAGCGTGAGT
GCCGGGGTCA GCTCGAACTG GAGCCTGTAA TTTGTGAGTG CGAGTGGGGA GCAGCAGGAG
GATCCTTTTC ATAGGTGAGG TCCCAGGAAC GAGCCTGGTC NGTGCTTAGG CAAAGGCCCT
TCCCACTTGT CAGCCTTGTT GTTTACCCAT CCCCTGCTTC TCCCAGACTT GCATTAATTC
CGNNGTCGGT TCCATCAACC CCGGNATCCC CTCCCCCGGG
```

MINT7 (SEQ ID NO:7)
```
CCCGGGACCC GCCCAGAACG CTTTCGTGGG GTTGGAGAGG GCAGGACACA GCCTCTCTGG
GCCCGGTAGT ATGCGAAGAC ACGCATAACG CAAAAGGATT CCCGTCCTGG ACTTTGGGAA
TTAAGGCCCT GAACACATTG AGCAAAAAGT AGATCTGTCT GTACAGACGT TTCTTTCCAC
GTCTTTCATA GTAAGGACTT TATTAAAAAG CAGGCACTCG AATCCTAGGT GGGTAGATGG
GAGGCTGGGG CTGGGGATGG GGACGTCCTC TGTTTTCTGG TTGTGCACAT TAAAAATAAC
TCTCTGCTGC CTACTCCTAA ACGCAGCCGG CAAAAATGAG ACGTAACTA AGCGCCGTTT
CAGTCCCAGA GCCAGGTCGT CCATGGGGGT TTTCAAGCGT TTTCTCGATG ACTGATTTTT
CTAGAAGCGA ATGGATTTTA TTCTCCCAGG TGTAAAGGCT ACCTCCTGCT TCACACCCGG
G
```

MINT8 (SEQ ID NO:8)
```
CCCGGGCTGT GGCGGTGCAA CTCCCGCCGC CTGCGTTCTA GACAGAAAAG CCCCTTCTGA
CCATGCATTA GTAGTACTAC TCCATTATTC CTGTTAGAAC AAGTTAAAAG TAAGGGTTGA
GCCCAAAGGC CCCAGGAGGG GGGTCATGTG CGCCCCAGTC ACTCAGGCTC CCCTCGCTTC
TCCGGTTCGA GTTATGCCAT CAAGCTAATA TATTGTGACT GCTCTTCTCT CCTGTGACAA
AAGGCTTGCA GCTGCCTCCA AATCAATAGA TTGTCAAAGA ATATTGAAA ACAATCATGA
CACAAAAACT TAATCCTGGN TTGGAGGCTA CATAATCAGA AATTGTGCTA CTTGTTCTTC
CAAGNCACCC GATTTAATTT ATCCCAAAC TTTTAGGCAA ATTTTTATTT CCCGGGACCT
TTTTCCCAGC AGATCCTGCT ACGTCTGTCG GGTTTGTAAT GTAATTTGTA ATTNCTNCCC
TTCATGTGGT CCGGTGCCTT GAACCATCTT TAATTAAAAG CATAATTAAG GGAAGATCTA
AAGAAAGACA ATTACCAGAT GGTCTTTTTT TTAGAGGCGG TAGTTGCGCA GAGAGGGGCT
CGGGGTCTGT CCCCGGG
```

FIG. 6B

MINT9 (SEQ ID NO:9)
CCCGGGTCAT TGTCCATCTC CGACCAGGGG AGTAGCCACC CCCACTAGCC AGCCGTCTTT
ATCTCCTAGA AGGGGAGGTT ACCTCTTCAA ATGAGGAGGC CCCCCAGTCC TGTTCCTCCA
CCAGCCCCAC TACGGAATGG GAGCGCATTT TAGGGTGGTT ACTCTGAAAC AAGGAGGGCC
TAGGAATCTA AGAGTGTGAA GAGTAGAGAG GAAGTACCTC TACCCACCAG CCCACCCAGT
CCCTCTCTCA GCAGTGGATG GGGATGGGGT GGGGGTAGGG ACGAGAAGGC AGCTGGTGGA
GAAACAGCTT CAAGACTCTT TGGGTTCCTC CTGCTCTCCA GGGGAGCTTA CCTGGGGCTA
ACTTTAGACA CACAGGTTTG GAGGGAGGAA AGAAGGAAGA ATTCTTTTAC AACGAATCAA
TTAAGAGCAC TTCCTCTTTT CTTAACTTGG GGGGAGGGCC AGGAAAACTT CTTGAGTCAA
GAAATCTTGG GAGGNAGACA TCAGATGTNG GCAAGAGGCA GACAGATTTT GGGAAGGCAG
GCTTTGGGTC AANAAAGATC AAGCCTGTGT TGTCCCCAGG CTCTTCCCTG TTCCCCCATC
CCGGG

MINT10 (SEQ ID NO:10)
CCCGGGGGCT GCAGAATCAG GAGTCTTCNC CTAGGTTTGG CCTTGGGCTC CATCCTACNC
CCTGAATGTG ACNGCTGCGT CTTCGTCCCA CACCTACTTT TGAATGCCAA GAGGGGGCTC
CGCTGGCCAG GACNGAATAT TTTTATGGTA AAAAATGACC GGCAGTTGCA TCAGCTCCAG
GAGGGTGGGA GCCGTCACCC GAGGTCGCAC AGGCAGACTG ATGAAAATTC TGCTTATAAA
GTCACTGCTC CCCCATTAAT TAGGGGGGAG GGGGCGCTCC GGAGCCACCA CGCACCTCGC
CCACGGNCAA AAAGCTTGTC AACATTTTCC ACGAAGGATT GAAAATGTAA ATTAACTTTC
AGATTATTCA ATGTCACCAA GGTATGGAAA AAGGTCGCCA TACTGGGTGT CATTTATCTC
GTTGTGGATT TAAAGAGCTT TTTCTATTAA ATTTCTTAAA ATTAATGTTT TATGTTGCTC
AGAGTAATTT AAACAATTAT GGGCTTAAAG AATTGATCAT TACAGCCCCT GGGATTTAGC
GCTGCAGGCT GATNNCCCTG AAAAACCTCT GATTTATCAG GGNTCGTATT NGGCCGGGCA
AGCCCGGG

MINT11 (SEQ ID NO:11)
CCCGGGAGTG GCTAACCAGG AANANNAGGC ACTGNCCACA CACCANGGGC TGGGAAATCA
AGTGGCCTGC ACCAAGGCGG CTTCGGGGGA CTTGTCTGTG GCAAGTCTTG GTAGTCCCCA
TTCAAACTTT TGCCTCGAGC GTGTTAAGAA CAACAACAAA AAAAAAATCA AAGTGCCAAA
GGTCCCTCTC TTCTCTCCAG CTCAAGAACC CACCACTTTT CTATGATTTC TTTACAATTT
ATTCCCTCCC TTCCCCCAAT TCCGTTAGTC ACTTTACCCC CACCCCACCC TGGGTTTCTT
TTGTCTGAAT CTTTTTCAAC ACCAAGGTCC CTCTGTATGC CTCTCCCCAA AAGCCCTTAT
GAAAAGTTAC CTGCATTTTT TAAGTGCCTA CATTTCTTAA CTTCGCCTAA CAGCTCTTTG
CCTTAATTAA AGCCTTCTAC CAATTGCTTC TTTTTTCTAA GCTCGCGGGT TTTTTTCAAT
AAGTTTTTTG TTTTTGTTTT TTAAGGGGGG AACAAAAGAA ACGTGATTAC CTTGGAAGGC
GGCTTATTGC AGTTTGGGGG GAAAATTCAC TGCAGCGCTG CGCGACTGGG TTCGGCGTTG
CCCAGGCGGG TCACATAGGA AGCGTGGTGG CCCGGG

MINT12 (SEQ ID NO:12)
CCCGGGTCCC AGCCCTGAGG ACCAGGTTTC AGGGCTCAGA AGACTCCAGC
GAGGTTCCCT CGCAGATTGT GTCTGCGGTC GTTGGGGGAG GGGCCCCGCA
GCCTTCAGCA GATTATCCAA AGGTCAGTGA CCCAGATATG GTTTTGGNCA
CGGGCCATGT TTCACTTCCT GTGCCCCAAG CAGAATTTAG CTGAATAATT
CGGACCCCAA ACCAAACAAA ACGCTCTTAT TTCCGTTTGG GGATTCTTCG
GAGTTGGGAT TTTTCTGTCT CAAATTAGAA TAATNTGCAT TATTAACCAA
CTTAACATTT ATTTGTTGGT TGGCTGCCTG ACCTTTCTGA GCCTCAGTTT
NTTCGTCTGT AAATTGGGAG CTTACCCAGG TCGGAGGACT GTTGGAATTG
GAAATATTCG AATAAGGAAG TGTTTTTGCA AGTGCTTTGT AAGCAGCAAA
GCGCTTCTTC AGGGGTCAAT TTTTTTTAGC TCTGCAGTCA CCACCCAAAT
TCGGAAGATC GTTGTGCCTT TCTTGGATGA GAATGCCCGG CTCCAGCCCG
GG

FIG. 6C

MINT13 (SEQ ID NO:13)
CCCGGGTGTG TGTTGTTCCC CTCCATGTAC CACGTGTTTG TCCTGATGGT CTCCTACCCC
CTGTCCCCCT GAGAGGCCCT GGTGTGTGTT GTTCCCCTCC ATGTATCCAC GTGTTTGTCC
TGATGGTCTC CTACCCCCCG TCCCCTGAG AGGCCCTGGT GTGTGTTGTT CCCCTCCATG
TACCCACGTG TTTGTCCTGA TGCTCTCCTA CCCCCTGTCC CCTGAGAGG CCCTGGTGTG
TGTTGTTCCC CTCCATGTAC CCACGTGTTT GTCCTGATGC TCTCCTACCC CCTGTCCCCC
TGANANGCCC GGG

MINT14 (SEQ ID NO:14)
CCCGGGAGTG GCCCTGCCTG GCCATTTGCT CAAGCAGCAT GCAAGCCGGA TCTACAGCCG
GTGCACCTTG TTCCTTGTTC TTCCGGGCAC CGGAGGCCCA CGTGAAACCT CTCAGAGGAG
AGCGAAGAAG GCCACCTTTC ATCTCAATGA GCCAACAGCC TCACATCCTT AAGTCCTGCC
TAATCTTACG AGTCATGAGT CATCGCTTCT TCCCCGCCAA GTCATTCAGG ATTCAGTGAC
TCCAGCTGCC CTCAGGATCT GACGGAATCT TGAAGGCAGA GTTCCGAGAC TGCAGTCCAG
GATAGAGAAG CCCCCGGCTC CATCAGGGGC TCCTCGGCTT CAAGGCAGGA CCCACCCCAA
AGCTNTCAAA GCGGCAGAGG CCTGTTTTCA GGTCTATTTT TAAAGATNTC TAGGGGAAGT
GGTTTCTGAA TGCTCTGTAG GATGAGGCTG TGAACAGTGA TTGTTTCATT TGCTCGGGGC
TGGCAAAAAA GGGATGTACA ACCCGTTCTG ACCACACCAG TGAGTTAAAA AGCACTGCAG
ACTATGAATA CCTTTTGCCA GTTGGACTGG TTATGGGGAC CGATGGCTTC CCCTACAACT
GGGGAGGCTG CCAGCCCGGG

MINT15 (SEQ ID NO:15)
CCCGGGACCT CTGCGGTTAC CTGGGCCTTC CCTGCCAGCC CCCACCCCCT GCCCCCACCA
GAAAGCGTTT ACAGGACAGG TGAGGCCCGC AGGAGGAAAA GCACTCCCCT GGCGCAACAT
GACTCCAGCG CATCTGCGTC TAAGCCACAC CGTGCTCCTG GTAGATTAAA AATTAATTCT
AAAAAAAAAA TCTCTCCTAT CCCAAATGCA CTGTTTTCTG CCTTGCTTGA CAATTGATTT
GTTTTTAAAG GAAAGTTATG GGTAGATCCT CTTTTTTCTT TCCCATTCTT TNNTTCTTCT
TTTATACTGG AGGGAGGGAA ACGGAGGCGA GGACACACAC GCGCAGGCAG GGGNTGAAAA
GGCCGAGGTG GGTTTTCCTG TTTAATATCA AAGGAGGGCG AATAATGGGT TTCCTCGGTC
CGGCTAGGCC GGCCTTTGAC TCAATTGGAA ATGCAAAGGC AGCTTTTGCC TATTNTCTGG
CTGCTGGCTG AGACCCTAAA TTTCCGTAGG AAATCGTCGG ACACGCACTT AATCGGNCTT
TGCAANCTTT CCCTCGAAGT TGCACGCGGG TCTGGGCGGA GGAGGCGAGG TAACCCTGGA
TTCGAACCAG CGCCTTTCTC TCCTTCAGGC CTCCGCCCGG G

MINT16 (SEQ ID NO:16)
CCCGGGACAA GGCGGGTCAC CTCTGGGGCC TCACCGCAGT TCCACTTCCT TTCTCGGGTA
TTTGGAAACC GTCACCCCGC CATTTCGGTG TGGGAAGAGC GCGCGGGCCC TGCCGGACTT
TAGTGCTTTA GGGGTTAATT TCGGCTGACA GGGACGGAG CCTAAGGCAG TGAGCGCCCC
AGTACCCTCA AACCTTATTG CTGGCCCCTG CTGTCTGAGC TTACAAGCAT TACCGCCGCT
ATTTCCGTGC GGGCTGACAC GGGAGATGAA AGTGGTGAAG ACACCCAGGG TGCGGGGGTG
GAGGTGGGGA GAGGAGCCAG ATGGGATTGA TCCCCAGAGC CAGATGGGAT TTAAAGGTGA
GGGAGGAGGG CATCCTGATG GCGTGTGGTC AGTTGATGCC AGATTGGATG GCTGAGACAC
CTCTGCAGCT TACAGGAAAG ACAGAGGGAA AGGGTTCTAT GAATTCTAGC TGTTCATACT
CAAAGCAAAT AATTAATCAA GTGGGGGGGG GGCCTCTAGC TGTAAACCCA TACCTCTAGG
AAACCTTTTG TCATGTGGAG CCACAGTGCT CACTTGACAG ATTCCCCACT GAGAAGTGGG
CTAAGAGGTT GGCCTGCATT GCTGGGTGCC TCCAGGTGGG GAGTCCTGTA CCTGGGAGCC
CGGG

FIG. 6D

MINT17 (SEQ ID NO:17)
CCCGGGCGCC GGGGGTCCCA TCCACTTCTC CCTACCTTCT CTCTCTCCTG TTGGAGAGGC
CAGGGGCTCC CGCGACTGAA AGGGGCCAGG CTGAGGCTGC CCAATCCCAG GGACAGGAAG
AACATTTTGG ATGGATCGCG GGGTGCAGAA AAAGGAAGTT GAGCGACAGA CGCNAAGCCC
AAAGCGTGGA ATTTGGGAAG AGGCAGAAAA AAAGTGGGCG AAGAGGAAGA GAAAAAACNA
GCNACGAGAT GGGGAGGGAC AAGAAGTTTG GGGAGGATAG AGAAAAAGAG AAACTGCCTG
GAAAACAAGT TGCAAGACAA TTGAAAAGTT GAATGAGAAG GAAAGANAGG AAGGTNGTNA
AATCAAATTA GAACTGTTGG AAAAGANGGC TGGGACACGG CTTTCTCTGG TTCTGTCCTC
CCAAGAAATT GGAAACCTCT CCCCTTCCCG GCACCAANCT TNCGGGATGT TCCGGTGCCC
CTCCCCCGGG

MINT18 (SEQ ID NO:18)
CCCGGGAGTG CTCCTGCCGG CAGCATGTCC ACTTGCTAGG GGCAGAGGGG CAGTGGGAGT
GTCCCCCATG TGCCAGCCTG TCCCACACT TGGGTTAACC TTCAGTCACC AGGAGGAATA
AGGTGTGACA CCTCTGAGAC TGTGGGCACA TGTGCTGCTG CCTGACAGTC ACAGGCTGTA
CTGTGCCAGT GACAGAGGCC ATGATGCCCA CATAACCCAA ACCCGAACCC GAACCCTAAC
CCCTAACCCC TAACCCTAAC CCTACCCTAA CCCTAACCCA GCCCTAACTC TAGCCCTAGC
CCTAGCCCTA GCCCTAAGCC CTAAGCCCTT AAGCCTAACC CCAAACCCCC AACCCCAACC
CCNAACCCTA ACCCTTAACC CTTCCCTCAA GCCTCTCNAA CCCTGCTTGG GTTTACAAGG
TTATTNAACC CCGGG

MINT19 (SEQ ID NO:19)
CCCGGGATTG GTCTTTTGGC TGGGATGTAA AGGAGGAGGA ACTAGCTGGG GAAAGGCTGG
GTAAGGGGGA AAACCCAGGG AATTTAACCC CCTCTTCTGT AAAATGAGAA CCCATTCATT
CACTTAGCAA ATCTTTATGG AGCTCTGTAG GGGCCCTGGG GGAAGGCGAC CAGAGTGTCT
GAAAGCAAAG AGCAGGAGAG TGTGGACTCA GCTGAGAGGA GAGCAGAGGC TGAGTGTCAG
GGTGGGGAGT GGGAAGGGGT TTCCAGGTGC CAACAAGGAC ACAAGCCAAG GTGTTGCAGT
AGGGCATTTG GGAACGTAT GAGAAGCGCT CCTGCCAGCT TCCCTGGCGG TGTCCTATTC
CCTGCATCCA TTTTGGACCA TGAGCCCCTT CTCTTACCCT CTGGCCAGGA CCGAATGCCA
TAGACTTCCC CAGATTGCCC GGG

MINT20 (SEQ ID NO:20)
CCCGGGCCCC AGGGCGGCCC GAACCCCAGC CAAGCCGGCC AGCAGCAGGG CCAACAGAAG
CAGAAGCGCC ACCGGACGCG CTTCACCCCC GCACAGCTCA ACGAGTTGGA GAGGAGCTTC
GCCAAGACTC ACTACCCCGA CATCTTTATG CGTGAGGAGC TGGCACTGCG TATCGGGCTG
ACCGAGTCCC GAGTGCAGGT ACGAGGGGCT TGGGATCTGG GACAGAAGGC AAGGACAGGG
CGGGAGGATT TGGGCAAAGG GAGCAGGGTC TTCCCTTCCC CTGTCGAGAT CCTGGGCTGC
TTTCAGGCTG CCTGTGCGTT CCTGTATCGA GTTATCTCCA TCTCTACCCG GAAACTGGTC
CCCATCGCCA TCCCCAATG GACACGCAAG GCCCGTCTCC GGCCAGTATA GCGACATCCC
GGAAGAAGCT CCTCAAAATC GAAGCCCGGC GTTGTCGGGC TACAGGGCTC GCCTCCTCCG
CCTGAGAAGG CAACCTCAGC GCCCCCGGG

MINT21 (SEQ ID NO:21)
CCCGGGAACT ACCTAACGCT AGTTCAGTCC CAAAATGCTG CCCAACGACA GAATGCTCGC
CTCCTTGCTT CCTCTAACAC TCTGGCACAC CCACTTGGTG TCGGGCCTCT ATGGGCTCGC
AGTGAAGCCC TGAGCCTGGG CTGCCCCTTC CCATGTGCCC CCTGCCAGCC GGCCCTCCCT
CCCTTTGGGT GCCCCATCCC TCCAGTCAAC TCCTAGCCGA CCCTTAAGAG TCAGGTATTT
GTAGCCTTCC CTGACATCCC TCCCAGGCTG TCCCACTGCC AGCAGGACGA GCCTGCCCCT
CCTCCACCCT CCTTACAGCT ATACCTAGCC TTGGCCATAA TCACTAATGG ACCAGGAAAC
ACCCTGGCGC GCAGAGCCAC CGCAAAGTGG CCCGCTCAGG CCCGCCCGGG

FIG. 6E

MINT22 (SEQ ID NO:22)
CCCGGGGATC TCAGAAAGGG AAGGATGTGG GGAGAGTGAA GGTGGAGGCA GTCACACCTA
TCCTGGTGAC CTTGGCGTGC CCCCCTGGAG TGACGAGCCA GGGGCTTATA TAGGTGCGAC
TAGGATGTTG CCTCGTTTTT CACTCGGGGC TGCGAAGAGG GCATTGCTCT TTCTGATGGC
TGGAAGACAG GGGCAAGGAG AGAGAGAACC GGCCCCGAGA CGGGCTGGAG GGTGGGGACA
CTGGGGAGTT TGGAGCTGGG GGTTCGGAGT GGGAGGTTTG GGTCTTCTGA GACGCTCCAG
ACTCTCCGGA GGCGGCAGAG GTCGAGGCAG GAGGCGAATG TGACGCTTAG GGTCGCTACG
GTTGATGTTG GGCGCCTTTG GAAGCTGGTC ATTAATTCTT GTCATCGGGA GGTTTCGCGG
ANGGCGACAG CGCCCGGG

MINT23 (SEQ ID NO:23)
CCCGGGCGCC CGGCCCTGGC TCGCGGAATG GGCGGCCAGA TCTCAGGCCC TGCGTGCCCG
AGCTCAGTCC CAGTTCCAAC CGGGGGTGCC CATGGACTCT CGGAGGGCAC TCCTGGGGGG
ACAGCTAAGA CACCAGGCTG CAGGATCACT CATTGCACGC TGCATAATCG CCGCCACAAA
CTCTCCCGTG CGCAAGAACA AACGCGCGTG GGACAGAAAA AGTTCCTAGG TCTCCGCAGG
AGTGAATGCA AAATCCAGGG GACTCAGGGT CATGTTGGGA GCCCCTTCTC CCCCGAGAG
TCAGGGAGCT GTTGAGGTGG GATCGGTGAG GGTCGCGCCA CGCGGGTCCC TTCCCTACCA
GGCTCGGATA CCATGCAGCG TGGACACTCC CGAGTTGCTC TGCGGAATCC CGGG

MINT24 (SEQ ID NO:24)
CCCGGGGACG GGGAGGGAGG AGGGCTGCCG GGATGTGAAC CGGGGAAGGC AGCTGGGGCT
GGAGAGCAGC GCGGAAAGGG GGCCCAGGGA GCTGGAAAGC GAGCCAAGAG GAGGGCAAGG
AAGGTGGCGG GCTACGGGGA GGGGAAAGAA AAAGGGTGTC TTGGCGGTGG CCTTGGTAAG
AGAAAGGGGC AAGGGGTATA ATTGACAAGG CACTGAAAGT ATTGAAGTCA GAGCCTTGGG
AAGGATCTAC CGAACTCTCG GCGGTCCACG CGGGGACAGA CCTCAGCCCG TGAGCCTTGA
GCTCCACGCG GGACAGACC TCAGCCCGTG AGCCTTGAGC TCCACGCGGG ACAGACCTC
AGCCCGTGAG CCTTGAGCTC CACGCGGGA CAGACCTCAG CCCGTGAGCC TTGANCCCAG
AAGGAGTGGC AACCTCANGA CGTTTGCCAA GTGGCCTGGA ATGTTANGGA AACCCCAGCC
CCGCCAGGAA CANANCTGGC ACTAATTCCC NGCTCGGNCC GGG

MINT25 (SEQ ID NO:25)
CCCGGGGTGG GAGCTGGCTC GTGGGGGCGT GCGCTGCGCG AAAGCGAAAG CCGCCCGCCA
GAGCAACTTT GCGGCGGAAG GCGCCGACGA GGAGCTGTGC CGTGCCGCTC TTGGGGATGG
TGAGCTGGCC GCCCCGGCCG GTGGGCAGCG CGTCCGGGCG CGGTGCTTCG CTAGCTATAA
ATAGGTGCTG TGCGGGGACA GGAAGATGGT TCCGCCCTT TACAAGCACC GGCCCGTTAT
GTGCGCTGGG CTAGGACCTT GCCCCGCAGC GGAGTGGGAG GAGTGAGGTT AGGGGTAACG
GTTGCATGGG ATGGGGGGTG GGCACATAGA GCCTACAGCA GAGTTGGCGG CGGGGCTCTC
CCATGCACTT GGTTGTTTGT CGTTTCTGCT TTTCCCGGG

MINT26 (SEQ ID NO:26)
CCCGGGCTCC GGCATAGCTC TAGATTAACG AGCTGGGCGA CGGGGGCGGG GGCAGCATGC
CCAGCGTCGG TGCACGGCCG GGGTTCTTAG ACATCACAAA CTGTGGAGCG ATACATTGGA
AGCGAAATCC AAGAACGACA CCGGCCGGCG TGTTTCTGAT GTAGTCGTGA TTAGTGTTGG
AGATGGCCAA GGGCGGCTTG CGGAGCCCAG GGAACGCAGC GAGCCAGGCC CGCGCCCCCC
TGCAAAGCTC TGCCTTGAAC CACGTAATTC AGGCACCCAG GGTGTCCCTC CCTAGGTCCT
GGCCACATTT CCCGAAGGTT ATTAAATGGA GAATTCAGCA GTGGAGTTAG AGACGGACGA
ATGTACAGGA AGATAAGAGG GAAACTCTTC CTCATTTGCT TTAGGGGGTT GTGCTGGGAA
AATGCGGGGA GGTTAAACAA AGCTTCTCCT ANGACTCCAC GATTCATTTC TAACAACTTC
TTAAAAGACT CCCGTCTCNG GAGCAGACGC NCCCTCCCCG CTCTCTAAGC CCCGCTGCAT
GAAANGATGC CCTCGGCCCC TTGCCAGAGG GCCGGGTCCG GGATTCCCGG G

FIG. 6F

MINT27 (SEQ ID NO:27)
```
CCCGGGATCC GGGAAGGCTC CCCCGAGCCG GGGTCGGAAC TGCGGCTGGA GGGGCCTCGG
CTTGAGGAGG ATCTGGGAGG GCGGGGGCTC AGTCCTGGCC ACCAGGTGTG AGGGGTCGGG
TGCGGAGCCC TGTGTCAGAC GCGGCGGTGA AGGCTGTAGC CCTGCTCTCC GGGATGGGGG
TGGTACTCTC ACCGCACCCT GCCCCAAGCC GCAGGGAGCC CCTGGCGCCC CTGGCGCCCG
GG
```

MINT28 (SEQ ID NO:28)
```
CCCGGGCCCC TGGCGGGGAC ACCGGGGGGG CGCCGGGGGC CTCCCACTTA TTCTACACCT
CTCATGTCTC TTCACCGTGC CAGACTAGAG TCAAGCTCAA CAGGGTCTTC TTTCCCCGCT
GATTCCGCCA AGCCCGTTCC CTTGGCTGTG GTTTCGCTGG ATAGTAGGTA GGGACAGTGG
GAATCTCGTT CATCCATTCA TGCGCGTCAC TAATTAGATG ACGAGGCATT TGGCTACCTT
AAGAGAGTCA TAGTTACTCC CGCCGTTTAC CCGCGCTTCA TTGAATTTCT TCACTTTGAC
ATTCAGAGCA CTGGGCAGAA ATCACATCGC GTCAACACCC GCCGCGGGCC TTCGCGATGC
TTTGTTTTAA TTAAACAGTC GGATTCCCCT GGTCCGCACC AGTTCTAAGT CGGCTGCTAG
GCGCCGGCCG ANGCGAAGCG CCGCGCGGAA CCGCGGGCCC GGG
```

MINT29 (SEQ ID NO:29)
```
CCCGGGAGCT GACCGTGGGG AGGCCGGTTC CGCTGGTTTC AACCAGCCCA CTCTCCCCTC
TTGGGATGCC CAACCCCGCG TACTCACCAT TTCCTGGTTT CCAGGATGTC CTGGCATCTT
AGCTATGCAT TTCCAGTACC TCCAGACCTC AGGGCAACAA AGGATGTGAC AAAGTCACCT
AGTGCTCCTG AGGGGCAACA CGCGGGACAG TAGAGATGGA TCTCAGGCTC CGGCCTGAGC
CAGAGACAAA GGCCGCGCCA AACGCTGGAA GCCACGCCCT CCTCCCCAAC TGCGTGCCTG
ATAGGACGGT TCCTACTCTG ACAGATTGAA TAAGGCTCCA GGACCCTCCC CCACACCCAC
CGTCCCCAGC ATTAGTGCGC TTTATGGACA GGGAAACGGG ATCCTGTANG CGGGGTCACA
CGCCCCGGG
```

MINT30 (SEQ ID NO:30)
```
CCCGGGCACC TGGGCTGGGG GGGCACTCAC ATGGCTACCG GAGGCCCCCA CGTGCGGCGC
CCCGCGGAGA CAGGGGTTCG CGTTCAGAGC TGGTGGCGGA TGGACCAGGT GGCCGCGGGG
ACCAGCTGGG TCCAGATGTG CTGGGCCTGC TGGAAGGGGA CAGGTGCTAC CTGGACGTGT
AATGGCCCTT GGTCTCTTTT GGCCGAACCT GCCGCTCCGA TCCCCCTCCA TCCCTTCATC
CCTCCATCCC TCCATCCCTC CATCCCTCCG GCCCTTCTCC CCTTCTTCCT CCGCTGCCTG
TGTTGCAGAG AGGGGCTGTC AGAGACTGTT GATGTGGGAA AAAATGAAAT GGGGGAGGGG
TTGTGATTGG CAAAGGCCAG TTGTGCCGGG AGCGGTGGGT AGAGGGGGTG CCCTGAGAGT
GGGAAGCCCT AAACTTGGAG GGCAGCGCTG ATGGGGAGAG GGTTCCTGGC ACCCCACCT
GCCTTGGAAG TGGGAAATGA CATAGCGGGA GGGGGGCTGC AGTTCCAGCC CCCGGG
```

MINT31 (SEQ ID NO:31)
```
CCCGGGGCCT CTATCCTGGC GGGAAGGGCA GGCCGACCCG GCAGACTGCG GCCTCTCGGG
AGGGAAGAAG GTGTCAGACG CGCGGAGCAA CCATAAATAG CCCCCCTTTC CCAGAAGACG
GCACGGGGTT CAAGACTCAG GCGCCGCATA CTCAGAATGA GAGCAGAGAC TCCCGCCAGG
AAAAAAGGGC ACTTAGGGGA TCTGCTCATT AACATGAAAT GCAAATGAGC CCGCCCGGCC
TCATTTACAC AACTCTGTGC ATGGATTCGG CGAAAGGGCA ACCAGGGAGA CGACGGCGCA
GCAGCCACTC TGCCACTTCC CCCATCCCCT CCCCCCCATC GGCCGGGCG GGAACTGAGA
CGACCCCAAC CCTCTGCGGC GGCGGGAGGT GCGCGGGGGC TGCGTGGGTG GTGCAGCCTT
AGGGGAGTGA ACAACCGCCA GGGGTGATGG CCTCAGCAAA GTGAGGGGTG GTGATGGAGG
TCATCCGACC CATCCGCGCC CCTCTCCGCA GTGGCGCAAG CGCCCCAAAA TCTCCGGAGA
NGGAACTGAG TGACCCACTA GGTTCCGCCC TGTCTACCTC TCGCAGATGT TGGGGAAGTG
CTTCCCGGCG TCTAATCCTC GCTGTTCCCC CCTCCACCGG CGCCCAGCAC ACCCGCGGCG
CTCCGCTCCC GGG
```

FIG. 6G

MINT32 (SEQ ID NO:32)
CCCGGGTACC TGCACAGCTC GCTCCCTCCC ATCCTTCGGG TCTTCGCTCG AACGTCCGCT
CCTCGGTGAG GCCTTCCCTG GACAACGCAT TTGAAACGTA ACCCCAAGGC AAGAAGCCAC
CTTCCAGGCG CGCAGCCGAA GCCCAGTGCC AAGGAGGCCG GAGACTCGGG TGCCCGCGCA
TCCCGAAAAC AGCCTCTGAG GGGTCCTCTG AGCATCCTTC CAGCGTGTTT GGGAGGCAAA
CTCGTTGACT AGCTCTTGAG AGGAGTGGCT AGAGGAATCC AGGCGGGGAA GGGGACGGTG
GACTCCAGGA GAGTGTAATT TACAAAGGCG GGGGCGGGG ACGCCAGGT CCGAGTCCCA
GGACTCTGCG CCGGACGCTT CGCCCGCCCT TTCAGGTCCC CTGCCCGGTC CTCGTACCCG
CGCGGGTCCG GAGAACCTCT GAGCACCGGC CCCCAGCCCC CGGG

MINT33 (SEQ ID NO:33)
CCCGGGCAGA AAGGCTCGGA TGGCGGTGGC AGAAAGGCTC GGAGGCGGTG GCCTCAGATC
CCTGGTCCCT CCGGGTCACT GTCGGCTAAT TCTGGGGGAA GGACTGGGCA AGGCTGTTTG
GAAGAAGTCA GCGCCCGGG

FIG. 6H

METHYLATED CPG ISLAND AMPLIFICATION (MCA)

CROSS REFERENCE TO RELATED APPLICATIONS

This application is a divisional application of U.S. application Ser. No. 09/309,175, filed May, 10, 1999 now issued as U.S. Pat. No. 7,700,324; which claims the benefit under 35 USC §119(e) to U.S. Application Ser. No. 60/106,925 filed Nov. 3, 1998, now expired. The disclosure of each of the prior applications is considered part of and is incorporated by reference in the disclosure of this application.

GRANT INFORMATION

This invention was made with government support under Grant Nos. CA43318 and CA54396 awarded by the National Cancer Institute, National Institutes of Health and Grant No. CA43318 awarded by the National Institutes of Health. The government has certain rights in the invention.

BACKGROUND OF THE INVENTION

1. Field of the Invention

The present invention relates generally to regulation of gene expression and more specifically to a method of determining the DNA methylation status of CpG sites in a given locus.

2. Background Information

DNA methylases transfer methyl groups from the universal methyl donor S-adenosyl methionine to specific sites on the DNA. Several biological functions have been attributed to the methylated bases in DNA. The most established biological function for methylated DNA is the protection of DNA from digestion by cognate restriction enzymes. The restriction modification phenomenon has, so far, been observed only in bacteria. Mammalian cells, however, possess a different methylase that exclusively methylates cytosine residues that are 5' neighbors of guanine (CpG). This modification of cytosine residues has important regulatory effects on gene expression, especially when involving CpG rich areas, known as CpG islands, located in the promoter regions of many genes.

Methylation has been shown by several lines of evidence to play a role in gene activity, cell differentiation, tumorigenesis, X-chromosome inactivation, genomic imprinting and other major biological processes (Razin, A., H., and Riggs, R. D. eds. in *DNA Methylation Biochemistry and Biological Significance.* Springer-Verlag, New York, 1984). In eukaryotic cells, methylation of cytosine residues that are immediately 5' to a guanosine, occurs predominantly in CG poor regions (Bird, A., *Nature,* 321:209, 1986). In contrast, CpG islands remain unmethylated in normal cells, except during X-chromosome inactivation (Migeon, et al, supra) and parental specific imprinting (Li, et al, *Nature,* 366:362, 1993) where methylation of 5' regulatory regions can lead to transcriptional repression. De novo methylation of the Rb gene has been demonstrated in a small fraction of retinoblastomas (Sakai, et al., *Am. J. Hum. Genet.,* 48:880, 1991), and recently, a more detailed analysis of the VHL gene showed aberrant methylation in a subset of sporadic renal cell carcinomas (Herman, et al., *Proc. Natl. Acad. Sci., U.S.A.,* 91:9700, 1994). Expression of a tumor suppressor gene can also be abolished by de novo DNA methylation of a normally unmethylated CpG island (Issa, et al, *Nature Genet.,* 7:536, 1994; Herman, et al., supra; Merlo, et al, *Nature Med.,* 1:686, 1995; Herman, et al, *Cancer Res.,* 56:722, 1996; Graff, et al, *Cancer Res.,* 55:5195, 1995; Herman, et al, *Cancer Res.,* 55:4525, 1995).

Human cancer cells typically contain somatically altered nucleic acid, characterized by mutation, amplification, or deletion of critical genes. In addition, the nucleic acid from human cancer cells often displays somatic changes in DNA methylation (E. R. Fearon, et al, *Cell,* 61:759, 1990; P. A. Jones, et al., *Cancer Res.,* 46:461, 1986; R. Holliday, Science, 238:163. 1987; A. De Bustros, et al, *Proc. Natl. Acad. Sci., USA,* 85:5693, 1988); P. A. Jones, et al, *Adv. Cancer Res.,* 54:1, 1990; S. B. Baylin, et al, *Cancer Cells,* 3:383, 1991; M. Makos, et al., *Proc. Natl. Acad. Sci., USA,* 89:1929, 1992; N. Ohtani-Fujita, et al., *Oncogene,* 8:1063, 1993). However, the precise role of abnormal DNA methylation in human tumorigenesis has not been established. Aberrant methylation of normally unmethylated CpG islands has been described as a frequent event in immortalized and transformed cells, and has been associated with transcriptional inactivation of defined tumor suppressor genes in human cancers. In the development of colorectal cancers (CRC), a series of tumor suppressor genes (TSG) such as APC, p53, DCC and DPC4 are inactivated by mutations and chromosomal. Some of these alterations result from a chromosomal instability phenotype described in a subset of CRC. Recently, an additional pathway has been shown to be involved in a familial form of CRC, hereditary non-polyposis colorectal cancer. The cancers from these patients show a characteristic mutator phenotype which causes microsatellite instability (MI), and mutations at other gene loci such as TGF-β-RII and BAX. This phenotype usually results from mutations in the mismatch repair (MMR) genes hMSH2 and hMLH1. A subset of sporadic CRC also show MI, but mutations in MMR genes appear to be less frequent in these tumors.

Another molecular defect described in CRC is CpG island (CGI) methylation. CGIs are short sequences rich in the CpG dinucleotide and can be found in the 5' region of about half of all human genes. Methylation of cytosine within 5' CGIs is associated with loss of gene expression and has been seen in physiological conditions such as X chromosome inactivation and genomic imprinting. Aberrant methylation of CGIs has been detected in genetic diseases such as the fragile-X syndrome, in aging cells and in neoplasia. About half of the tumor suppressor genes which have been shown to be mutated in the germline of patients with familial cancer syndromes have also been shown to be aberrantly methylated in some proportion of sporadic cancers, including Rb, VHL, p16, hMLH1, and BRCA1. TSG methylation in cancer is usually associated with (1) lack of gene transcription and (2) absence of coding region mutation. Thus, it has been proposed that CGI methylation serves as an alternative mechanism of gene inactivation in cancer.

The causes and global patterns of CGI methylation in human cancers remain poorly defined. Aging could play a factor in this process because methylation of several CGIs could be detected in an age-related manner in normal colon mucosa as well as in CRC. In addition, aberrant methylation of CGIs has been associated with the MI phenotype in CRC as well as specific carcinogen exposures. However, an understanding of aberrant methylation in CRC has been somewhat limited by the small number of CGIs analyzed to date. In fact, previous studies have suggested that large numbers of CGIs are methylated in immortalized cell lines, and it is not well understood whether this global aberrant methylation is caused by the cell culture conditions or whether they are an integral part of the pathogenesis of cancer.

Most of the methods developed to date for detection of methylated cytosine depend upon cleavage of the phosphodiester bond alongside cytosine residues, using either methylation-sensitive restriction enzymes or reactive chemicals such as hydrazine which differentiate between cytosine and its 5-methyl derivative. Genomic sequencing protocols which identify a 5-MeC residue in genomic DNA as a site that is not cleaved by any of the Maxam Gilbert sequencing reactions have also been used, but still suffer disadvantages such as the requirement for large amount of genomic DNA and the difficulty in detecting a gap in a sequencing ladder which may contain bands of varying intensity.

Mapping of methylated regions in DNA has relied primarily on Southern hybridization approaches, based on the inability of methylation-sensitive restriction enzymes to cleave sequences which contain one or more methylated CpG sites. This method provides an assessment of the overall methylation status of CpG islands, including some quantitative analysis, but is relatively insensitive and requires large amounts of high molecular weight DNA. Another method utilizes bisulfite treatment of DNA to convert all unmethylated cytosines to uracil. The altered DNA is amplified and sequenced to show the methylation status of all CpG sites. However, this method is technically difficult, labor intensive and without cloning amplified products, it is less sensitive than Southern analysis, requiring approximately 10% of the alleles to be methylated for detection.

Identification of the earliest genetic changes in tumorigenesis is a major focus in molecular cancer research. Diagnostic approaches based on identification of these changes are likely to allow implementation of early detection strategies and novel therapeutic approaches targeting these early changes might lead to more effective cancer treatment.

SUMMARY OF THE INVENTION

The invention provides a method for detecting a methylated CpG-containing nucleic acid. This method can be used to identify sequences which are differentially methylated during a disease process such as a cell proliferative disorder.

In one embodiment, a method is provided for identifying a methylated CpG-containing nucleic acid. The method includes contacting a nucleic acid sample suspected of containing a CpG-containing nucleic acid, with a methylation sensitive restriction endonuclease that cleaves only unmethylated CpG sites, under conditions and for a time to allow cleavage of unmethylated nucleic acid; and contacting the sample with an isoschizomer of the methylation sensitive restriction endonuclease, wherein the isoschizomer of the methylation sensitive restriction endonuclease cleaves both methylated and unmethylated CpG sites. Oligonucleotides are added to the nucleic acid sample under conditions and for a time to allow ligation of the oligonucleotides to nucleic acid cleaved by the restriction endonuclease and the digested nucleic acid is amplified for further analysis.

In another embodiment, a method is provided for detecting an age-associated disorder associated with methylation of CpG islands in a nucleic acid sequence of interest in a subject having or at risk of having said disorder. The method includes contacting a nucleic acid sample suspected of comprising a CpG-containing nucleic acid with a methylation sensitive restriction endonuclease that cleaves only unmethylated CpG sites under conditions and for a time to allow cleavage of unmethylated nucleic acid, and contacting the sample with an isoschizomer of the methylation sensitive restriction endonuclease, wherein the isoschizomer of the methylation sensitive restriction endonuclease cleaves both methylated and unmethylated CpG sites. Oligonucleotides are added to the nucleic acid sample under conditions and for a time to allow ligation of the oligonucleotides to nucleic acid cleaved by the restriction endonuclease, and the digested nucleic acid is amplified. The amplified, digested nucleic acid is contacted with a membrane and the membrane is hybridized with a probe of interest.

In yet another embodiment, a method is provided for evaluating the response of a cell to an agent. The method includes contacting a nucleic acid sample suspected of containing a CpG-containing nucleic acid with a methylation sensitive restriction endonuclease that cleaves only unmethylated CpG sites, under conditions and for a time to allow cleavage of unmethylated nucleic acid, and contacting the sample with an isoschizomer of the methylation sensitive restriction endonuclease, wherein the isoschizomer of the methylation sensitive restriction endonuclease cleaves both methylated and unmethylated CpG sites. Oligonucleotides are added to the nucleic acid sample under conditions and for a time to allow ligation of the oligonucleotides to nucleic acid cleaved by the restriction endonuclease, and the digested nucleic acid is amplified. The amplified, digested nucleic acid is adhered to a membrane and the membrane is hybridized with a probe of interest.

In a further embodiment, a kit for the detection of a methylated CpG-containing nucleic acid is provided. In one embodiment the kit includes a carrier means containing one or more containers including a container containing an oligonucleotide for ligation of the oligonucleotides to nucleic acid, a second container containing a methylation sensitive restriction endonuclease and a third container containing an isoschizomer of the methylation sensitive endonuclease. In another embodiment the kit includes a carrier means containing one or more containers containing a membrane, wherein the membrane has a member of the group consisting SEQ ID NO:1, SEQ ID NO:2, SEQ ID NO:4, SEQ ID NO:6, SEQ ID NO:8, SEQ ID NO: 9, SEQ ID NO: 10, SEQ ID NO:14, SEQ ID NO: 15, SEQ ID NO: 17, SEQ ID NO:19, SEQ ID NO:20, SEQ ID NO:22, SEQ ID NO:23, SEQ ID NO:24, SEQ ID NO:27, SEQ ID NO:30, SEQ ID NO:31, SEQ ID NO:32, and SEQ ID NO:33 (MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32, and MINT33 immobilized on the membrane.

In a further embodiment, an isolated nucleic acid including a member selected from SEQ ID NO1, SEQ ID NO:2, SEQ ID NO:4, SEQ ID NO:6, SEQ ID NO:8, SEQ ID NO: 9, SEQ ID NO:10, SEQ ID NO.14, SEQ ID NO:15, SEQ ID NO:17, SEQ ID NO:19, SEQ ID NO:20, SEQ ID NO:22, SEQ ID NO:23, SEQ ID NO:24, SEQ ID NO:27, SEQ ID NO:30, SEQ ID NO:31, SEQ ID NO:32, and SEQ ID NO:33 (MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32, and MINT33) is provided. An isolated methylated nucleic acid sequence having a sequence as set forth in a member of the group consisting of SEQ ID NOs:1-33 (MINT1-33) is also provided.

BRIEF DESCRIPTION OF THE DRAWINGS

FIGS. 4A and 4B are a pictorial representation of global hypermethylation in CRC. Each column represents a separate gene locus. Each row is a primary colorectal cancer (samples above the bold solid line) or polyp (below the bold solid line). Black squares: methylation>10%. Hatched squares: 1-10% methylation. White squares: <1% methylation. Panel A: GH+MI+, Panel B: GH+MI−, Panel C: GH−MI+, Panel D: GH−MI−, Panel E: GH+, Panel F: GH. Panels A-D are cancers. Panels E and F are adenomas. MI denotes the presence of microsatellite instability. ND, not done.

FIGS. 6A-H are the nucleic acid sequences of MINT1-33 (SEQ ID NO: 1-33).

DETAILED DESCRIPTION OF THE INVENTION

Figure 1:
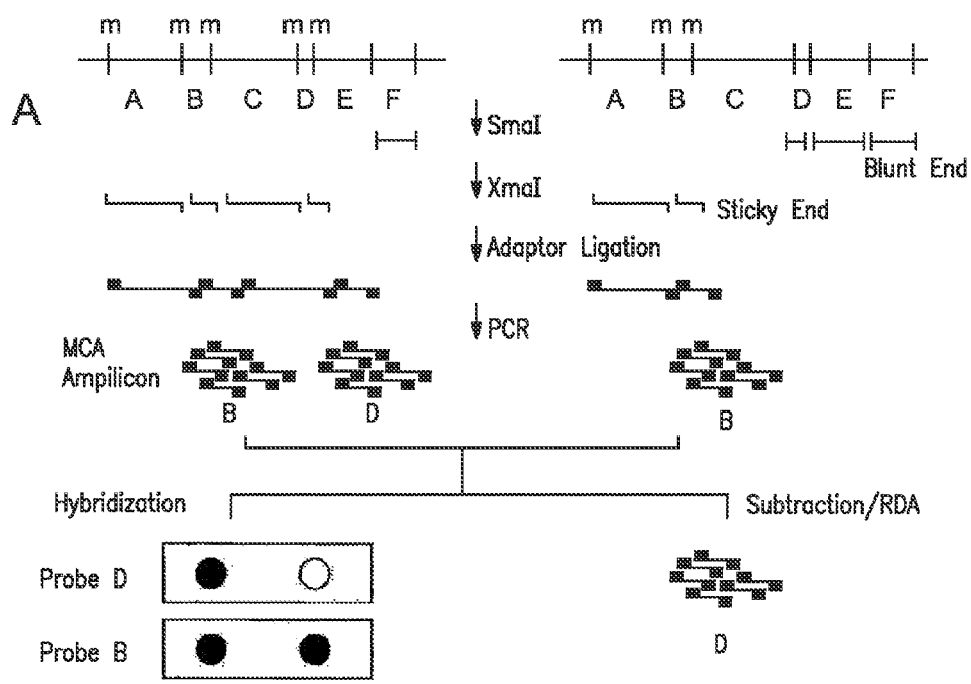
FIG. 1A is a schematic diagram of MCA. A hypothetical fragment of genomic DNA is represented by a solid line, with 7 SmaI sites depicted by tick marks. Methylated SmaI sites are indicated by an m. Fragments B and D are CpG islands. B is methylated in both normal (right) and cancer (left), while D is differentially methylated in cancer. For MCA, unmethylated SmaI sites are eliminated by digestion with SmaI (which is methylation-sensitive and does not cleave when its recognition sequence CCCGGG contains a methylated CpG), which leaves the fragment blunt ended. Methylated SmaI sites are then digested with the non-methylation sensitive SmaI isoschizomer XmaI, which digests methylated CCCGGG sites, leaving a CCGG overhang (sticky ends). Adaptors are ligated to these sticky ends, and PCR is performed to amplify the methylated sequences. The MCA amplicons can be used directly in a dot blot analysis to study the methylation status of any gene for which a probe is available (left). Alternatively, MCA products can be used to clone differentially methylated sequence by RDA (right).
FIG. 1B shows a dot blot of p16 CGI amplification in the Caco2 cell line and normal colon mucosa. To examine the quantitative aspect of MCA, DNA from Caco2 and normal colon mucosa were mixed in various proportions, and the methylation level of each mix was determined using MCA. The numbers indicate the percent Caco2 DNA in the mixture.
FIG. 1C shows the differential methylation of RDA clones by dot blot probed with MCA products from Caco2 and normal colon (N).
Figure 1:
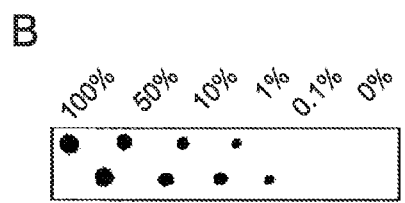
Figure 1:
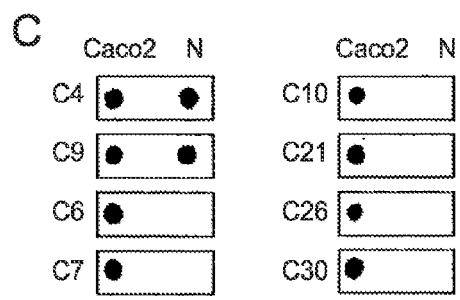

The present invention provides a method for identifying a methylated CpG-containing nucleic acid called methylated CpG island amplification (MCA). MCA can be used to study methylation in normal and neoplastic cells, and allows rapid screening of nucleic acid samples for the presence of hypermethylation of specific genes. MCA can also be used to clone genes and nucleic acid sequences differentially methylated in normal and abnormal tissues and cells.

It should be noted that as used herein and in the appended claims, the singular forms "a," "and," and "the" include plural referents unless the context clearly dictates otherwise. Thus, for example, reference to "a cell" includes a plurality of such cells and reference to "the restriction enzyme" includes reference to one or more restriction enzymes and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference in full for the purpose of describing and disclosing the methodologies which are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

Any nucleic acid sample, in purified or nonpurified form, can be utilized as the starting nucleic acid or acids, provided it contains, or is suspected of containing, a nucleic acid sequence containing the target locus (e.g., CpG-containing nucleic acid). In general the CpG-containing nucleic acid will be DNA. However, the process may employ, for example, samples that contain DNA, or DNA and RNA, including messenger RNA, wherein DNA or RNA may be single stranded or double stranded, or a DNA-RNA hybrid may be included in the sample. A mixture of nucleic acids may also be employed. The specific nucleic acid sequence to be detected may be a fraction of a larger molecule or can be present initially as a discrete molecule, so that the specific sequence constitutes the entire nucleic acid. It is not necessary that the sequence to be studied be present initially in a pure form; the nucleic acid may be a minor fraction of a complex mixture, such as contained in whole human DNA. The nucleic acid may be contained in a biological sample. Such samples include but are not limited to a serum, urine, saliva, cerebrospinal fluid, pleural fluid, ascites fluid, sputum, stool, or biopsy sample. The nucleic acid-containing sample used for detection of methylated CpG may be from any source including, but not limited to, brain, colon, urogenital, hematopoietic, thymus, testis, ovarian, uterine, prostate, breast, colon, lung and renal tissue and may be extracted by a variety of techniques such as that described by Maniatis, et al. (Molecular Cloning: a Laboratory Manual. Cold Spring Harbor, N.Y., pp 280, 281, 1982).

The nucleic acid of interest can be any nucleic acid where it is desirable to detect the presence of a CpG island. In one embodiment, the CpG island comprises a CpG island located in a gene. A "CpG island" is a CpG rich region of a nucleic acid sequence. The nucleic acid sequence may be, for example, a p16, a Rb, a VHL, a hMLH1, or a BRCA1 gene. Alternatively the nucleic acid of interest can be, for example, a MINT 1-33 nucleic acid sequence. However, any gene or nucleic acid sequence of interest containing a CpG sequence can be detected using the method of the invention.

The presence of methylated CpG in the nucleic acid-containing specimen may be indicative of a disorder. In one embodiment, the disorder is a cell proliferative disorder. A "cell proliferative disorder" is any disorder in which the proliferative capabilities of the affected cells is different from the normal proliferative capabilities of unaffected cells. An example of a cell proliferative disorder is neoplasia. Malignant cells (i.e., cancer) develop as a result of a multistep process. Specific, non-limiting examples of disorders associated with increased methylation of CpG-islands are colon cancer, lung cancer, renal cancer, leukemia, breast cancer, prostate cancer, uterine cancer, astrocytoma, glioblastoma, and neuroblastoma.

In another embodiment, the disorder is an age-associated disorder. The term "age-associated disorder" is used to describe a disorder observed with the biological progression of events occurring over time in a subject. Preferably, the subject is a human. Non-limiting examples of age-associated disorders include, but are not limited to, atherosclerosis, diabetes melitis, and dementia. An age-associated disorder may also be a cell proliferative disorder. Examples of age-associated disorders which are cell proliferative disorders include colon cancer, lung cancer, breast cancer, prostate cancer, and melanoma, amongst others. An age-associated disorder is further intended to mean the biological progression of events that occur during a disease process that affects the body, which mimic or substantially mimic all or part of the aging events which occur in a normal subject, but which occur in the diseased state over a shorter period of time.

In one embodiment, the age-associated disorder is a "memory disorders or learning disorders" which are characterized by a statistically significant decrease in memory or learning assessed over time by the Randt Memory Test (Randt et al, *Clin. Neuropsychol.*, 2:184, 1980), Wechsler Memory Scale (*J. Psych.*, 19:87-95, 1945), Forward Digit Span test (Craik, *Age Differences in Human Memory*, in: *Handbook of the Psychology of Aging*, Birren, J., and Schaie, K., Eds., New York, Van Nostrand, 1977), Mini-Mental State Exam (Folstein et al., *J. of Psych. Res.* 12:189-192, 1975), or California VeRbal Learning Test (CVLT) wherein such non-neurodegenerative pathological factors as aging, anxiety, fatigue, anger, depression, confusion, or vigor are controlled for. (See, U.S. Pat. No. 5,063,206 for example).

If the sample is impure (e.g., plasma, serum, stool, ejaculate, sputum, saliva, cerebrospinal fluid or blood or a sample embedded in paraffin), it may be treated before amplification with a reagent effective for opening the cells, fluids, tissues, or animal cell membranes of the sample, and for exposing the nucleic acid(s). Methods for purifying or partially purifying nucleic acid from a sample are well known in the art (e.g., Sambrook et al., *Molecular Cloning: a Laboratory Manual*. Cold Spring Harbor Press, 1989, herein incorporated by reference).

In one embodiment, a method is provided for identifying a methylated CpG-containing nucleic acid, including contacting a nucleic acid sample suspected of comprising a CpG-containing nucleic acid with a methylation sensitive restriction endonuclease that cleaves only unmethylated CpG sites under conditions and for a time to allow cleavage of unmethylated nucleic acid. The sample is further contacted with an isoschizomer of the methylation sensitive restriction endonuclease, that cleaves both methylated and unmethylated CpG-sites, under conditions and for a time to allow cleavage of methylated nucleic acid. Oligonucleotides are added to the nucleic acid sample under conditions and for a time to allow ligation of the oligonucleotides to nucleic acid cleaved by the restriction endonuclease, and the digested nucleic acid is amplified. Following identification, the methylated CpG-containing nucleic acid can be cloned, using method well known to one of skill in the art (see Sambrook et al., *Molecular Cloning: a Laboratory Manual*. Cold Spring Harbor Press, 1989).

A "methylation sensitive restriction endonuclease" is a restriction endonuclease that includes CG as part of its recognition site and has altered activity when the C is methylated as compared to when the C is not methylated. Preferably, the methylation sensitive restriction endonuclease has inhibited activity when the C is methylated (e.g., SmaI). Specific non-limiting examples of a methylation sensitive restriction endonucleases include Sma I, BssHII, or HpaII. Such enzymes can be used alone or in combination. Other methylation sensitive restriction endonucleases will be known to those of skill in the art and include, but are not limited to SacII, EagI, and BstUI, for example. An "isoschizomer" of a methylation sensitive restriction endonuclease is a restriction endonuclease which recognizes the same recognition site as a methylation sensitive restriction endonuclease but which cleaves both methylated and unmethylated CGs. One of skill in the art can readily determine appropriate conditions for a restriction endonuclease to cleave a nucleic acid (see Sambrook et al., *Molecular Cloning: a Laboratory Manual*. Cold Spring Harbor Press, 1989). Without being bound by theory, actively transcribed genes generally contain fewer methylated CGs than in other genes.

In the method of the invention, a nucleic acid of interest is cleaved with a methylation sensitive endonuclease. In one embodiment, cleavage with the methylation sensitive endonuclease creates a sufficient overhang on the nucleic acid of interest. Following cleavage with the isoschizomer, the cleavage product can still have a sufficient overhang. An "overhang" refers to nucleic acid having two strands wherein the strands end in such a manner that a few bases of one strand are not base paired to the other strand. A "sufficient overhang" refers to an overhang of sufficient length to allow specific hybridization of an oligonucleotide of interest. In one embodiment, a sufficient overhang is at least two bases in length. In another embodiment, the sufficient overhang is four or more bases in length. An overhang of a specific sequence on the nucleic acid of interest may be desired in order for an oligonucleotide of interest to hybridize. In this case, the isoschizomer can be used to create the overhang having the desired sequence on the nucleic acid of interest.

In another embodiment, the cleavage with a methylation sensitive endonuclease results in a reaction product of the nucleic acid of interest that has a blunt end or an insufficient overhang. In this embodiment, an isoschizomer of the methylation sensitive restriction endonuclease can create a sufficient overhang on the nucleic acid of interest. "Blunt ends" refers to a flush ending of two stands, the sense stand and the antisense strand, of a nucleic acid.

Once a sufficient overhang is created on the nucleic acid of interest, an oligonucleotide is ligated to the nucleic acid cleaved of interest which has been cleaved by the methylation specific restriction endonuclease. "Ligation" is the attachment of two nucleic acid sequences by base pairing of substantially complementary sequences or by the formation of a covalent bonds between two nucleic acid sequences. An "oligonucleotide" is a nucleic acid sequence of 2 to 40 bases in length. Preferably the oligonucleotide is from 15 to 35 bases in length. In one embodiment, the oligonucleotide is ligated to the overhang on the nucleic acid sequence of interest by base pairing.

In one embodiment, two oligonucleotides are utilized to form an adaptor. An "adaptor" is a double-stranded nucleic acid sequence with one end that has a sufficient single-stranded overhang at one or both ends such that the adaptor can be ligated by base-pairing to a sufficient overhang on a nucleic acid of interest that has been cleaved by a methylation sensitive restriction enzyme or an isoschizomer of a methylation sensitive restriction enzyme. In one embodiment, two oligonucleotides can be used to form an adaptor; these oligonucleotides are substantially complementary over their entire sequence except for the region(s) at the 5' and/or 3' ends that will form a single stranded overhang. The single stranded overhang is complementary to an overhang on the nucleic acid cleaved by a methylation sensitive restriction enzyme or an isoschizomer of a methylation sensitive restriction enzyme, such that the overhang on the nucleic acid of interest will base pair with the 3' or 5' single stranded end of the adaptor under appropriate conditions. The conditions will vary depending on the sequence composition (GC vs AT), the length, and the type of nucleic acid (see Sambrook et al., *Molecular Cloning: a Laboratory Manual* 2nd Ed.; Cold Spring Harbor Laboratory Press, Plainview, N.Y., 1998).

Following the ligation of the oligonucleotide, the nucleic acid of interest is amplified using a primer complementary to the oligonucleotide. Specifically, the term "primer" as used herein refers to a sequence comprising two or more deoxyribonucleotides or ribonucleotides, preferably more than three, and most preferably more than 8, which sequence is capable of initiating synthesis of a primer extension product, which is substantially complementary to a nucleic acid such as an adaptor or a ligated oligonucleotide. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. In one embodiment, the primer is an oligodeoxyribo-nucleotide. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12-20 or more nucleotides, although it may contain fewer nucleotides.

Primers of the invention are designed to be "substantially" complementary to each strand of the oligonucleotide to be amplified and include the appropriate G or C nucleotides as discussed above. This means that the primers must be sufficiently complementary to hybridize with their respective strands under conditions which allow the agent for polymerization to perform. In other words, the primers should have sufficient complementarity with a 5' and 3' oligonucleotide to hybridize therewith and permit amplification of CpG containing nucleic acid sequence.

Primers of the invention are employed in the amplification process which is an enzymatic chain reaction that produces exponential quantities of target locus relative to the number of reaction steps involved (e.g., polymerase chain reaction or PCR). Typically, one primer is complementary to the negative (−) strand of the locus and the other is complementary to the positive (+) strand. Annealing the primers to denatured nucleic acid followed by extension with an enzyme, such as the large fragment of DNA Polymerase I (Klenow) and nucleotides, results in newly synthesized + and − strands containing the target locus sequence. Because these newly synthesized sequences are also templates, repeated cycles of denaturing, primer annealing, and extension results in exponential production of the region (i.e., the target locus sequence) defined by the primer. The product of the chain reaction is a discrete nucleic acid duplex with termini corresponding to the ends of the specific primers employed.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (*Tetrahedron Letters*, 22:1859-1862, 1981). One method for synthesizing oligonucleotides on a modified solid support is described in U.S. Pat. No. 4,458,066.

Where the CpG-containing nucleic acid sequence of interest contains two strands, it is necessary to separate the strands of the nucleic acid before it can be used as a template for the amplification process. Strand separation can be effected either as a separate step or simultaneously with the synthesis of the primer extension products. This strand separation can be accomplished using various suitable denaturing conditions, including physical, chemical, or enzymatic means, the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffmann-Berling (*CSH-Quantitative Biology*, 43:63, 1978) and techniques for using RecA are reviewed in C. Radding (*Ann. Rev. Genetics*, 16:405-437, 1982).

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, generally at a pH of about 7-9. Preferably, a molar excess (for genomic nucleic acid, usually about 10$^8$:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. a large molar excess is preferred to improve the efficiency of the process.

The deoxyribonucleoside triphosphates dATP, dCTP, dGTP, and dTTP are added to the synthesis mixture, either separately or together with the primers, in adequate amounts and the resulting solution is heated to about 90°-100° C. from about 1 to 10 minutes, preferably from 1 to 4 minutes. After this heating period, the solution is allowed to cool to approximately room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, E. coli DNA polymerase I, Klenow fragment of E. coli DNA polymerase I, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each locus nucleic acid strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

Preferably, the method of amplifying is by PCR, as described herein and as is commonly used by those of ordinary skill in the art. However, alternative methods of amplification have been described and can also be employed.

Once amplified, the nucleic acid can be attached to a solid support, such as a membrane, and can be hybridized with any probe of interest, to detect any nucleic acid sequence. Several membranes are known to one of skill in the art for the adhesion of nucleic acid sequences. Specific non-limiting examples of these membranes include nitrocellulose (Nitropure) or other membranes used in for detection of gene expression such as polyvinylchloride, diazotized paper and other commercially available membranes such as Genescreen™, Zetaprobe™ (Biorad), and Nytran™. Methods for attaching nucleic acids to these membranes are well known to one of skill in the art. Alternatively, screening can be done in a liquid phase.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically. In general, conditions of high stringency are used for the hybridization of the probe of interest.

The probe of interest can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the probe, or will be able to ascertain such, using routine experimentation.

In one embodiment, representational difference analysis (RDA, see Lisitsyn et al., *Science* 259:946-951, 1993, herein incorporated by reference) can be performed on CpG-containing nucleic acid following MCA. MCA utilizes kinetic and subtractive enrichment to purify restriction endonuclease fragments present in one population of nucleic acid fragments but not in another. Thus, RDA enables the identification of small differences between the sequences of two nucleic acid populations. RDA uses nucleic acid from one population as a "tester" and nucleic acid from a second population as a "driver," in order to clone probes for single copy sequences present in (or absent from) one of the two populations. In one embodiment, nucleic acid from a "normal" individual or sample, not having a disorder such as a cell-proliferative disorder is used as a "driver," and nucleic acid from an "affected" individual or sample, having the disorder such as a cell proliferative disorder is used as a "tester." In one embodiment, the nucleic acid used as a "tester" is isolated from an individual having a cell proliferative disorder such as colon cancer, lung cancer, renal cancer, leukemia, breast cancer, prostate cancer, uterine cancer, astrocytoma, glioblastoma, and neuroblastoma. The nucleic acid used as a "driver" is thus normal colon, normal lung, normal kidney, normal blood cells, normal breast, normal prostate, normal uterus, normal astrocytes, normal glial and normal neurons, respectively. In an additional embodiment, the nucleic acid used as a "driver" is isolated from an individual having a cell proliferative disorder such as colon cancer, lung cancer, renal cancer, leukemia, breast cancer, prostate cancer, uterine cancer, astrocytoma, glioblastoma, and neuroblastoma. The nucleic acid used as a "tester" is thus normal colon, normal lung, normal kidney, normal blood cells, normal breast, normal prostate, normal uterus, normal astrocytes, normal glial and normal neurons, respectively. One of skill in the art will readily be able to identify the "tester" nucleic acid useful with to identify methylated nucleic acid sequences in given "driver" population.

Screening Agents for an Effect on Methylation

The invention provides a method for identifying an agent which can affect methylation. An agent can affect methylation by either increasing or decreasing methylation. The method includes incubating an agent and a sample containing a CpG-containing polynucleotide under conditions sufficient to allow the components to interact, and measuring the effect of the compound on the methylation of the CpG-containing nucleic acid. In one embodiment, the sample is a cell expressing a polynucleotide of interest. In another embodiment, the sample is substantially purified nucleic acid. "Substantially purified" nucleic acid is nucleic acid which has been separated from the cellular components which naturally accompany it, or from contaminating elements such as proteins, lipids, or chemical resins. Substantially pure nucleic acid can be extracted from any cell type, or can be chemically synthesized. Purity can be measured by any appropriate method, such as measuring the absorbance of light (e.g., $A_{260}/A_{280}$ ratio).

The nucleic acid can be identified by the methylated CpG island amplification, as described above. The methylation of the polynucleotide in the sample can then be compared to the methylation of a control sample not incubated with the agent. The effect of the agent on methylation of a polynucleotide can be measured by assessing the methylation of the polynucleotide by the methods of the invention. Alternatively, the effect of the agent on methylation of a polynucleotide can be measured by assessing the expression of the polynucleotide of interest. Means of measuring expression are well known to one of skill in the art (e.g., Northern blotting or RNA dot blotting, amongst others).

The agents which affect methylation can include peptides, peptidomimetics, polypeptides, pharmaceuticals, and chemical compounds and biological agents. Psychotropic, antiviral, and chemotherapeutic compounds can also be tested using the method of the invention.

"Incubating" includes conditions which allow contact between the test agent and the cell of interest. "Contacting" includes in solution and solid phase. The test agent may also be a combinatorial library for screening a plurality of compounds. Agents identified in the method of the invention can be further cloned, sequenced, and the like, either in solution of after binding to a solid support, by any method usually applied to the isolation of a specific DNA sequence Molecular techniques for DNA analysis (Landegren et al, *Science* 242: 229-237, 1988) and cloning have been reviewed (Sambrook et al., *Molecular Cloning: a Laboratory Manual,* 2nd Ed.; Cold Spring Harbor Laboratory Press, Plainview, N.Y., 1998.

The sample can be any sample of interest. The sample may be a cell sample or a membrane sample prepared from a cell sample. Suitable cells include any host cells containing a nucleic acid including a CpG island. The cells can be primary cells or cells of a cell line.

In one embodiment, the agent is incubated with the sample of interest suspected of including a CpG-containing nucleic acid and methylation is evaluated by MCA. Thus, nucleic acid from the sample suspected of including a CpG-containing nucleic acid is contacted with a methylation sensitive restriction endonuclease which cleaves only unmethylated CpG sites under conditions and for a time to allow cleavage of unmethylated nucleic acid. An isoschizomer of the methylation sensitive restriction endonuclease is also utilized. An oligonucleotide is added to the nucleic acid sample under conditions and for a time to allow ligation of the oligonucleotide to nucleic acid cleaved by said restriction endonuclease, and the digested nucleic acid is amplified. The digested nucleic acid is adhered to a membrane, and the membrane is hybridized with a probe of interest. In one embodiment, representation difference analysis can also be performed.

Kits

The materials for use in the assay of the invention are ideally suited for the preparation of a kit. Such a kit may comprise a carrier means containing one or more container means such as vials, tubes, and the like, each of the container means comprising one of the separate elements to be used in the method. One of the container means can comprise a container containing an oligonucleotide for ligation to nucleic acid cleaved by a methylation sensitive restriction endonuclease. One or more container means can also be included comprising a primer complementary to the oligonucleotide. In addition, one or more container means can also be included which comprise a methylation sensitive restriction endonuclease. One or more container means can also be included containing an isoschizomer of said methylation sensitive restriction enzyme.

In another embodiment, the kit may comprise a carrier means containing one or more container means comprising a solid support, wherein the solid support has a nucleic acid sequence selected from the group consisting of MINT1-33 immobilized on the solid support. In one embodiment, the solid support is a membrane. Several membranes are known to one of skill in the art for the adhesion of nucleic acid sequences. Specific non-limiting examples of these membranes include nitrocellulose (Nitropure) or other membranes used in for detection of gene expression such as polyvinylchloride, diazotized paper and other commercially available membranes such as Genescreen™, Zetaprobe™ (Biorad), and Nytran™. The MINT1-33 sequences immobilized on the solid support can then be hybridized to nucleic acid sequences produced by performing the MCA procedure on the nucleic acids of a sample of interest in order to determine if the nucleic acid sequences contained in the sample are methylated.

Polynucleotides and Polypeptides

In another embodiment, the invention provides isolated MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 and MINT33 polynucleotides (SEQ ID NO1, SEQ ID NO:2, SEQ ID NO:4, SEQ ID NO:6, SEQ ID NO:8, SEQ ID NO: 9, SEQ ID NO:10, SEQ ID NO:14, SEQ ID NO:15, SEQ ID NO:17, SEQ ID NO: 19, SEQ ID NO:20, SEQ ID NO:22, SEQ ID NO:23, SEQ ID NO:24, SEQ ID NO:27, SEQ ID NO:30, SEQ ID NO:31, SEQ ID NO:32, and SEQ ID NO:33, respectively). These polynucleotides include DNA, cDNA and RNA sequences which encode MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 and MINT33 polypeptides. It is understood that naturally occurring, synthetic, and intentionally manipulated polynucleotides are included. For example, MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 and MINT33 nucleic acids may be subjected to site-directed mutagenesis. The nucleic acid sequence for MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 and MINT33 also includes antisense sequences, and sequences encoding dominant negative forms of MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 and MINT33.

The invention provides methylated and unmethylated forms of MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 and MINT33 polynucleotides (SEQ ID NO1, SEQ ID NO:2, SEQ ID NO:4, SEQ ID NO:6, SEQ ID NO:8, SEQ ID NO: 9, SEQ ID NO:10, SEQ ID NO:14, SEQ ID NO:15, SEQ ID NO:17, SEQ ID NO:19, SEQ ID NO:20, SEQ ID NO:22, SEQ ID NO:23, SEQ ID NO:24, SEQ ID NO:27, SEQ ID NO:30, SEQ ID NO:31, SEQ ID NO:32, and SEQ ID NO:33, respectively). Methylated nucleic acid sequences are also provided which include MINT3, MINT5, MINT 7, MINT11, MINT12, MINT13, MINT16, MINT18, MINT21, MINT25, MINT26, MINT28, and MINT29 (SEQ ID NO:3, SEQ ID NO:5, SEQ ID NO:7, SEQ ID NO:11, SEQ ID NO:12, SEQ ID NO:13, SEQ ID NO:16, SEQ ID NO:18, SEQ ID NO:21, SEQ ID NO:25, SEQ ID NO:26, SEQ ID NO:28, and SEQ ID NO:29, respectively). It is understood that naturally occurring, synthetic, and intentionally manipulated polynucleotides are included.

The polynucleotides of the invention includes "degenerate variants", sequences that are degenerate as a result of the genetic code. There are 20 natural amino acids, most of which are specified by more than one codon. Therefore, all degenerate nucleotide sequences are included in the invention as long as the amino acid sequence of a polypeptide encoded by the nucleotide sequence of SEQ ID NOs: 1-33 is functionally unchanged.

Specifically disclosed herein are methylated and unmethylated isolated polynucleotide sequences of MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 and MINT33. Preferably, the nucleotide sequence is SEQ ID NO1, SEQ ID NO:2, SEQ ID NO:4, SEQ ID NO:6, SEQ ID NO:8, SEQ ID NO: 9, SEQ ID NO:10, SEQ ID NO:14, SEQ ID NO:15, SEQ ID NO:17, SEQ ID NO:19, SEQ ID NO:20, SEQ ID NO:22, SEQ ID NO:23, SEQ ID NO:24, SEQ ID NO:27, SEQ ID NO:30, SEQ ID NO:31, SEQ ID NO:32, and SEQ ID NO:33, respectively. Specifically disclosed herein are methylated isolated polynucleotide sequences of MINT3, MINT5, MINT 7, MINT11, MINT12, MINT13, MINT16, MINT18, MINT21, MINT25, MINT26, MINT28, and MINT29. Preferably, the nucleotide sequence is SEQ ID NO:3, SEQ ID NO:5, SEQ ID NO:7, SEQ ID NO:11, SEQ ID NO:12, SEQ ID NO:13, SEQ ID NO:16, SEQ ID NO:18, SEQ ID NO:21, SEQ ID NO:25, SEQ ID NO:26, SEQ ID NO:28, and SEQ ID NO:29, respectively. The term "polynucleotide" or "nucleic acid sequence" refers to a polymeric form of nucleotides at least 10 bases in length. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. The term includes single and double forms of DNA.

The polynucleotide encoding MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 and MINT33 includes SEQ ID NO1, SEQ ID NO:2, SEQ ID NO:4, SEQ ID NO:6, SEQ ID NO:8, SEQ ID NO: 9, SEQ ID NO:10, SEQ ID NO:14, SEQ ID NO:15, SEQ ID NO:17, SEQ ID NO:19, SEQ ID NO:20, SEQ ID NO:22, SEQ ID NO:23, SEQ ID NO:24, SEQ ID NO:27, SEQ ID NO:30, SEQ ID NO:31, SEQ ID NO:32, and SEQ ID NO:33, dominant negative forms of MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 and MINT33, and nucleic acid sequences complementary to SEQ ID NO1, SEQ ID NO:2, SEQ ID NO:4, SEQ ID NO:6, SEQ ID NO:8, SEQ ID NO: 9, SEQ ID NO:10, SEQ ID NO:14, SEQ ID NO:15, SEQ ID NO.17, SEQ ID NO:19, SEQ ID NO:20, SEQ ID NO:22, SEQ ID NO:23, SEQ ID NO:24, SEQ ID NO:27, SEQ ID NO:30, SEQ ID NO:31, SEQ ID NO:32, and SEQ ID NO:33. A complementary sequence may include an antisense nucleotide. When the sequence is RNA, the deoxynucleotides A, G, C, and T of SEQ ID NO1, SEQ ID NO:2, SEQ ID NO:4, SEQ ID NO:6, SEQ ID NO:8, SEQ ID NO: 9, SEQ ID NO:10, SEQ ID NO:14, SEQ ID NO:15, SEQ ID NO:17, SEQ ID NO:19, SEQ ID NO:20, SEQ ID NO:22, SEQ ID NO:23, SEQ ID NO:24, SEQ ID NO:27, SEQ ID NO:30, SEQ ID NO:31, SEQ ID NO:32, and SEQ ID NO:33 are replaced by ribonucleotides A, G, C, and U, respectively. Also included in the invention are fragments of the above-described nucleic acid sequences that are and are at least 15 bases in length, which is sufficient to permit the fragment to selectively hybridize to DNA that encoded by SEQ ID NO1, SEQ ID NO:2, SEQ ID NO:4, SEQ ID NO:6, SEQ ID NO:8, SEQ ID NO: 9, SEQ ID NO:10, SEQ ID NO:14, SEQ ID NO:15, SEQ ID NO:17, SEQ ID NO:19, SEQ ID NO:20, SEQ ID NO:22, SEQ ID NO:23, SEQ ID NO:24, SEQ ID NO:27, SEQ ID NO:30, SEQ ID NO:31, SEQ ID NO:32, and SEQ ID NO:33 under physiological conditions or a close family member of MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 and MINT33. The term "selectively hybridize" refers to hybridization under moderately or highly stringent conditions which excludes non-related nucleotide sequences. Hybridization conditions have been described above.

The MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32, and MINT33 nucleotide sequence includes the disclosed sequence and conservative variations of the polypeptides encoded by MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 and MINT33 polynucleotides. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 and MINT33 nucleic acid sequences can be expressed in vitro by DNA transfer into a suitable host cell. "Host cells" are cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In one aspect, the MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 and MINT33 polynucleotide sequences may be inserted into an expression vector. The term "expression vector" refers to a plasmid, virus or other vehicle known in the art that has been manipulated by insertion or incorporation of the sequence of interest genetic sequences. Polynucleotide sequence which encode sequence of interest can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to included, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see, e.g., Bitter et al., *Methods in Enzymology* 153:516-544, 1987). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

In the present invention, the MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 and MINT33 polynucleotide sequence may be inserted into an expression vector which contains a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., *Gene* 56:125, 1987), the pMSXND expression vector for expression in mammalian cells (Lee and Nathans, *J. Biol. Chem.* 263:3521, 1988) and baculovirus-derived vectors for expression in insect cells. The DNA segment can be present in the vector operably linked to regulatory elements, for example, a promoter {e.g., T7, metallothionein I, or polyhedron promoters).

MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 and MINT33 polynucleotide sequences can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

By "transformation" is meant a genetic change induced in a cell following incorporation of new DNA (i.e., DNA exogenous to the cell). Where the cell is a mammalian cell, the genetic change is generally achieved by introduction of the DNA into the genome of the cell (i.e., stable).

By "transformed cell" is meant a cell into which (or into an ancestor of which) has been introduced, by means of recombinant DNA techniques, a DNA molecule encoding sequence of interest. Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the CaCl$_2$ method using procedures well known in the art. Alternatively, MgCl$_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the sequence of interest, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*. Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

In one embodiment, the invention provides substantially purified polypeptide encoded by MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 and MINT33 polynucleotide sequences. The term "substantially purified" as used herein refers to a polypeptide which is substantially free of other proteins, lipids, caRbohydrates or other materials with which it is naturally associated. One skilled in the art can purify a polypeptide encoded by MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 and MINT33 polynucleotide sequence using standard techniques for protein purification. The substantially pure polypeptide will yield a single major band on a non-reducing polyacrylamide gel. The purity of the MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 and MINT33 polypeptide can also be determined by amino-terminal amino acid sequence analysis.

Minor modifications of the MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32, and MINT33 primary amino acid sequences may result in proteins which have substantially equivalent activity as compared to the unmodified counterpart polypeptide described herein. Such modifications may be deliberate, as by site-directed mutagenesis, or may be spontaneous. All of the polypeptides produced by these modifications are included herein as long as the biological activity still exists.

The polypeptides of the invention also include dominant negative forms of the MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 or MINT33 polypeptide which do not have the biological activity of MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 or MINT33 polynucleotide sequence. A "dominant negative form" of MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32, or MINT33 is a polypeptide that is structurally similar to MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 or MINT33 polypeptide but does not have wild-type MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 or MINT33 function. For example, a dominant-negative MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 or MINT33 polypeptide may interfere with wild-type MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 or MINT33 function by binding to, or otherwise sequestering, regulating agents, such as upstream or downstream components, that normally interact functionally with the MINT1, MINT2, MINT4, MINT6, MINT8, MINT 9, MINT10, MINT14, MINT15, MINT17, MINT19, MINT20, MINT22, MINT23, MINT24, MINT27, MINT30, MINT31, MINT32 or MINT33 polypeptide.

EXAMPLES

The following examples are intended to illustrate but not to limit the invention in any manner, shape, or form, either explicitly or implicitly. While they are typical of those that might be used, other procedures, methodologies, or techniques known to those skilled in the art may alternatively be used.

Example 1

Detection of Methylated CpG Islands Using MCA

The principle underlying MCA involves amplification of closely spaced methylated SmaI sites to enrich for methylated CGIs. The MCA technique is outlined in FIG. 1A. About 70 to 80% of CpG islands contain at least two closely spaced (<1 kb) SmaI sites (CCCGGG). Only those SmaI sites within these short distances can be amplified using MCA, ensuring representation of the most CpG rich sequences. Briefly, DNA is digested with SmaI, which cleaves only unmethylated sites, leaving blunt ends between the C and G. DNA is then digested with the SmaI isoschizomer XmaI, which does cleave methylated CCCGGG sites, and which leaves a 4 base overhang. Adaptors are ligated to this overhang, and PCR is performed using primers complementary to these adaptors. The amplified DNA is then spotted on a nylon membrane and can be hybridized with any probe of interest.

As a model experiment, amplification of the p16 gene CGI was examined because (1) hypermethylation of this CGI in cancer is well characterized, and correlates with silencing of the gene and (2) this CGI contains two closely spaced SmaI sites (400 bp) which can be amplified by MCA. Initially, the reaction was optimized by testing different primers with a variable GC content, and different PCR conditions. As shown in FIG. 1B, using primers with a 70% GC content, the p16 CGI is amplified strongly in the Caco2 cell line, where it is known to be hypermethylated, while no signal above background was detected from any normal colon mucosa. To examine the quantitative aspect of MCA, DNA from Caco2 and normal colon mucosa were mixed in various proportions, and the methylation level of each mix was determined using MCA. MCA detected p16 methylation in a semi-quantitative manner between 1% and 100% methylated alleles. Finally, MCA was performed on 109 samples of normal colonic mucosa and adjacent primary colorectal tumor that had previously been typed for p16 methylation by Southern blot analysis. MCA and Southern blot were concordant in 107/109 (98%) of the cases. In one case, MCA detected a low level of methylation (5-10%) in a cancer sample that had been judged negative by Southern blot. In the other discordant case (positive by MCA, negative by Southern blot), the discordance may be related to heterogeneous p16 methylation, as has been described.

MCA is a novel PCR-based technique that allows for the rapid enrichment of hypermethylated CG rich sequences, with a high representation of methylated CpG islands. This technique can have several potential applications. MCA is very useful for the determination of the methylation status of a large number of samples at multiple loci simultaneously. By optimizing the PCR conditions, it should be readily adaptable to the study of the methylation status of any gene that has two closely spaced SmaI sites. As shown herein, there is a very high concordance rate between MCA and other methods for the detection of hypermethylation such as Southern blot analysis and bisulfite-based methods. However, MCA (1) requires good quality DNA, excluding the study of paraffin-embedded samples, (2) examines only a limited number of CpG sites within a CGI and (3) is sensitive to incomplete digestion using the methylation-sensitive enzyme SmaI. Nevertheless, many steps in MCA are amenable to automation and, by allowing for the examination of multiple genes relatively quickly, may have important applications in population-based studies of CGI methylation.

Example 2

Identification of Differentially Methylated Cg in CRC by MCA/RDA

To identify novel CGIs aberrantly methylated in CRC, RDA was performed on MCA amplicons from the colon cancer cell line Caco2 as a tester, and a mixture of DNA from the normal colon mucosa of 5 different men (to avoid cloning polymorphic SmaI sites or inactive and methylated X chromosome genes from women) as a driver. Two separate experiments were conducted, one using a lower annealing temperature (72° C.), and the other using a higher annealing temperature (77° C.) and more GC rich primers. After two rounds of RDA, the PCR products were cloned, and colonies containing inserts were identified by PCR. Based on initial experiments, we expected most of the recovered clones to contain Alu repetitive sequences, which are CG rich and hypermethylated. All clones were therefore probed with an Alu fragment, and only non-hybridizing clones were analyzed further. Out of 160 non-Alu clones, 46 were independent clones and 33 of these (MINT1-33, Methylated in Tumors, SEQ ID NOs:1-33, respectively) appeared to be differentially methylated in Caco2 cells by comparing hybridization to MCA products from Caco2 and normal colon (FIG. 1C). Nineteen of the clones (MINT1-19) were obtained using the lower annealing temperature, and 14 (MINT 20-33) using the higher temperature.

To confirm the aberrant methylation of these clones, Southern blot analysis was performed using DNA digested with SmaI or XmaI. All of the 33 clones were hypermethylated in Caco2 compared to normal colon mucosa. Of these 33, one clone (MINT 13) detected highly repeated sequences and two clones (MINT 18 and MINT28) appeared to correspond to mildly repeated gene families (data not shown). All others appeared to detect single copy DNA fragments. In addition, hypermethylation at CpG sites within the clones and distinct from the SmaI sites was confirmed by bisulfite-PCR for 6 clones. In each case, Caco2 was found to be hypermethylated at these sites.

Figure 2:
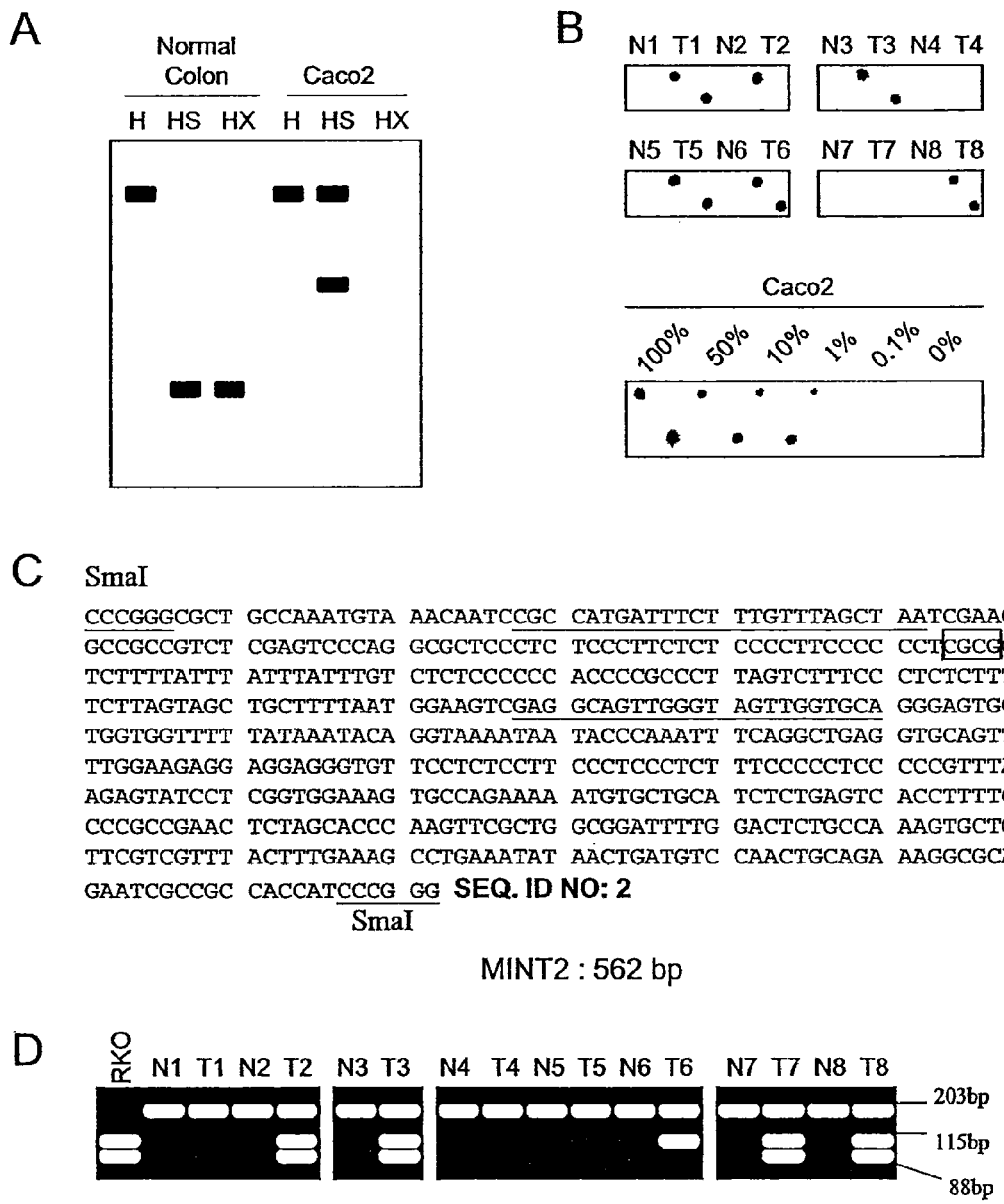
FIG. 2A illustrates methylation of MINT2 detected by Southern blot analysis. Genomic DNA from normal colon mucosa and cell line Caco2 was digested with restriction endonucleases (H, HindIII; HS, HindIII+SmaI; HX, HindIII+XmaI), electrophoresed, blotted, and hybridized with MINT2 probe.
FIG. 2B shows detection of MINT2 methylation by MCA (top panel) and quantitative MCA analysis (bottom panel). Sample numbers are shown above each lane in the top panel; N, normal colon; T, colon tumor. In the bottom panel, DNA from Caco2 and normal colon mucosa were mixed in various proportions, and the methylation level of each mix was determined using MCA. The numbers indicate the percent Caco2 DNA in the mixture.
FIG. 2C shows the nucleotide sequence of a differentially Methylated Clone, MINT2 obtained by MCA Followed by RDA. The restriction endonuclease sites for SmaI are underlined. Primer sequences used for bisulfite-PCR are also underlined. The restriction endonuclease site for BstUI used to detect methylation after bisulfite PCR is shown by a gray box.
FIG. 2D shows Bisulfite-PCR analysis of clones showing type A and type C methylation in normal colon (N) and colon tumor (T).

By DNA sequencing (example shown in FIG. 2), we found that 29 clones had a GC content greater than 50%, and satisfied the minimal criteria for CGIs (200 bp, GC content>50%, CpG/GpC>0.5). As might be expected, clones obtained with the higher annealing temperature and more GC rich primers had a relatively higher GC content (Table 1). The size of each clone, percentage of GC nucleotide, observed/expected CGs, sequence homology, and chromosomal location are summarized in Table 1. MINT5, MINT8, MINT11, MINT14 and MINT16 contained GC rich regions only in one end of the clones, and these may have been recovered from the edge of CGIs.

TABLE 1

Summary of the 33 Differentially Methylated Clones Isolated by MCA-RDA

| Clone | Size (bp) | % GC | O/E | CGI | Blast Homology | Chromosome Map | Methylation Pattern |
|---|---|---|---|---|---|---|---|
| MINT1 | 528 | 56 | 0.6 | Yes | None | 5q13-14 | Type C |
| MINT2 | 562 | 50 | 0.8 | Yes | None | 2p22-21 | Type C |
| MINT3 | 563 | 55 | 1 | Yes | Human EST AA557808 | 1p34-35 | Type a |
| MINT4 | 481 | 60 | 0.8 | Yes | None | 15q25-26 | Type a |
| MINT5 | 852 | 46 | 0.5 | Yes* | Human CpG clone 88c1 | 14q21-22 | Type a |
| MINT6 | 401 | 59 | 0.6 | Yes | None | 12q14-15 | Type a |
| MINT7 | 481 | 49 | 0.9 | Yes | Human genomic DNA | 6p21-22 | Type A |
| MINT8 | 617 | 46 | 0.5 | Yes* | None | N.D | Type A |
| MINT9 | 605 | 54 | 0.3 | No | None | 1p34-35 | Type A |
| MINT10 | 608 | 49 | 0.6 | Yes | None | 9q34-Ter | Type A |
| MINT11 | 637 | 49 | 0.6 | Yes* | Versican | 5q12-13 | Type A |
| MINT12 | 552 | 49 | 0.6 | Yes | CpG clone 33h2 | 7q31-32 | Type C |
| MINT13 | 308 | 60 | 0.9 | Yes | LINE1 | N.D | Cell line |
| MINT14 | 620 | 54 | 0.4 | Yes* | None | 10p13-15 | Type A |
| MINT15 | 641 | 53 | 0.7 | Yes | None | 11p12-13 | Type A |
| MINT16 | 664 | 62 | 0.5 | Yes* | Alpha-tubulin | 2q | Type A |
| MINT17 | 491 | 54 | 0.7 | Yes | None | 6 | Type C |
| MINT18 | 435 | 58 | 0.1 | No | Acrogranin | N.D | Cell line |
| MINT19 | 443 | 55 | 0.2 | No | None | N.D | Type A |
| MINT20 | 510 | 67 | 0.8 | Yes | mouse OTP | N.D | Type A |
| MINT21 | 411 | 62 | 0.4 | No | None | 22q13 | Type A |
| MINT22 | 438 | 60 | 0.9 | Yes | None | 10p12 | Type A |
| MINT23 | 346 | 64 | 0.8 | Yes | Csx | 5q34-35 | Type A |
| MINT24 | 525 | 63 | 0.7 | Yes | None | 3p25-26 | Type A |
| MINT25 | 339 | 60 | 0.7 | Yes | Human genomic DNA | 22q11 | Type C |
| MINT26 | 591 | 58 | 0.8 | Yes | CpG clone 73e1 | 7q11 | Type A |
| MINT27 | 242 | 74 | 0.7 | Yes | None | N.D | Type C |
| MINT28 | 463 | 58 | 1 | Yes | Ribosomal RNA gene | N.D | Type A |
| MINT29 | 429 | 60 | 0.7 | Yes | CpG clone 20b1 | 7q11 | N.D |
| MINT30 | 536 | 65 | 0.5 | Yes | None | 20q11 | Type A |
| MINT31 | 673 | 65 | 0.8 | Yes | None | 17q21 | Type C |
| MINT32 | 464 | 66 | 1 | Yes | None | 20q13 | Type A |
| MINT33 | 139 | 65 | 0.8 | Yes | None | N.D | N.D |

O/E: Observed/expected numbers of CpGs. N.D: not determined.
*Only one portion of the clones has a CpG island.

By DNA homology search using the BLAST program (BLAST 2.0, default parameters, available on the world wide web at ncbi.nlm.nih.gov), 4 clones were identical to human gene sequences, four clones were identical to CGIs randomly sequenced from a CGI library, one was identical to an EST, two clones were identical to high throughput genomic sequences deposited in Genbank, three clones had significant homology to other genes and the other 19 had no significant match in the database; MINT11 was identical to exon 1 and intron 1 of the human versican gene, and corresponded to the 3' edge of a promoter associated CGI; MINT14 was identical to exon 1 of the human alpha-tubulin gene, and was also the 3' edge of the CGI; MINT 24 corresponded to the 3' noncoding region of the human homeobox gene CSX; MINT21 had a region with 94% homology at the nucleotide level to exon 2 of the mouse OPT gene and probably represents the human homologue of this gene; MINT28 was homologous to ribosomal gene sequences; MINT18 was homologous to the acrogranin gene family. To examine the presence of potential promoter sequences in these clones, promoter prediction was performed using several computer programs (see programs available on the world wide web at dot.imgen.bcm.tmc.edu). Twenty out of the 33 clones were predicted as promoters using the NNPP program, and 6 were predicted as promoters using the TSSG program.

The chromosomal position of most of the unknown clones was determined using a somatic cell hybrid panel and a radiation hybrid panel (Table 1). Of note, MTNT3 and MTNT9 mapped to chromosome 1p35-36, MINT13 mapped to 7q31, MINT24 mapped to 3p25-26, MINT25 mapped to 22q11-Ter, and MINT31 mapped to 17q21. All of these chromosomal segments are areas that are frequently deleted in various tumors.

An important application of MCA is in the discovery of novel genes hypermethylated in cancer. As demonstrated here, MCA coupled with RDA is a rapid and powerful technology for this purpose, and compares favorably with other described techniques. In addition to the identification of genes hypermethylated in cancer, MCA could potentially be used to discover novel imprinted genes using parthenogenetic DNA, as well as novel X-chromosome genes.

Example 3

Silencing of the Versican Gene in CRC

Figure 3:
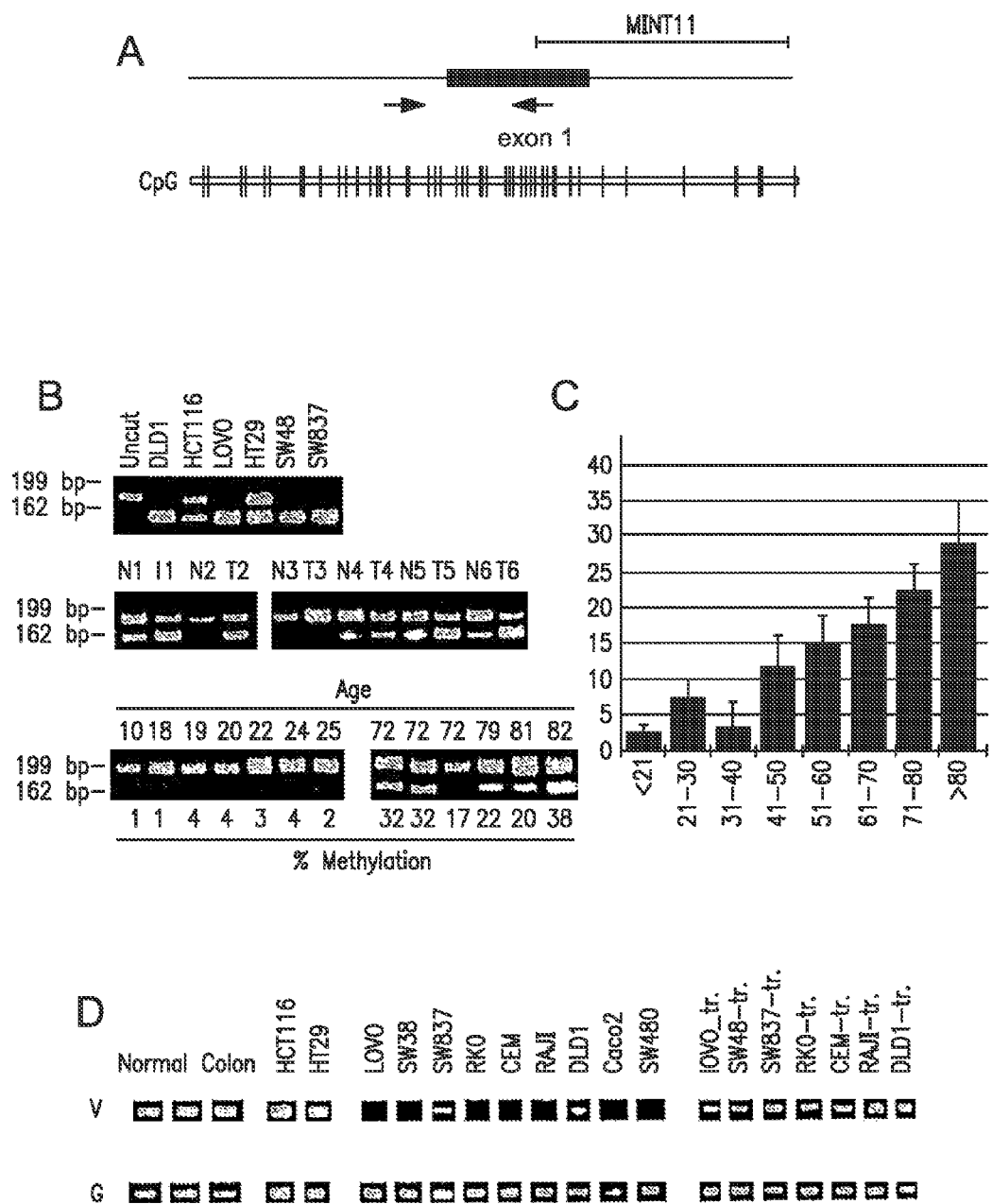
FIG. 3A shows a map of the versican gene first exon (filled box) and flanking regions. The position of MINT11 is shown by a solid line (on top). CpG sites are indicated below. Location of the primers used for bisulfite-PCR are shown by arrows.
FIG. 3B shows bisulfite-PCR analysis of the region around transcription start site of the versican gene. Following amplification, the PCR product was digested with restriction enzymes that distinguish methylated from unmethylated DNA. The top panel indicates the level of methylation in colon cancer cell lines (DLD1, LOVO, SW48, SW837, HCT116 and HT29). The middle panel shows methylation in various samples of normal colon (N) and primary colon tumor (T). The bottom panel shows age-related methylation.
FIG. 3C is a graph showing the level of methylation in normal colon mucosa with increasing age.
FIG. 3D shows bisulfite-PCR of normal colon, various cell lines, and the same cell lines following treatment with the methyl-transferase inhibitor 5-deoxy-azacitidine.

To determine whether some of these clones truly represented genes silenced by methylation, we examined the versican gene in more detail. Versican is a secreted glycoprotein that appears to be regulated by the Rb tumor suppressor gene. MINT11 corresponds to part of exon 1 and part of intron 1 of the versican gene (FIG. 3A). Hypermethylation of the two SmaI sites in exon 1 and intron 1 in colon cancer cell lines was confirmed by both Southern blot analysis and MCA. In order to determine if this methylation was representative of the entire CGI, including the proximal promoter, PCR was performed on bisulfite-treated DNA using primers designed to amplify the region around the transcription start site of this gene. The PCR product was then digested with restriction enzymes that distinguish methylated from unmethylated DNA. The versican promoter was found to be completely methylated in the colon cancer cell lines, DLD1, LOVO, SW48 and SW837, and partially methylated in HCT116 and HT29 (FIG. 3B). In primary colon tumors, versican was hypermethylated in 17 out of 25 cases (68%). Interestingly, some methylation of the versican promoter was also found in normal tissues, albeit at lower levels when compared to tumors. The level of methylation in normal colon mucosa increased with age of the patient (FIG. 3C), from an average of 6.9% in patients between 20 and 30 years of age, to an average of 28.9% in patients over 80. A linear regression analysis revealed a significant association between age and versican promoter methylation (R=0.7, P<0.000001). Using RT-PCR, we next examined the expression of versican in normal colon mucosa and CRC cell lines. Versican was found to be expressed in normal colon epithelium, but was markedly down-regulated or absent in methylated colon cancer cell lines. Expression of versican in all these cell lines was easily restored after treatment with the demethylating agent, 5-aza-deoxycytidine. These data suggest that versican becomes methylated in normal colon in an age-dependent manner, and that this leads to hypermethylation and loss of expression in most colorectal tumors.

Using MCA/RDA 33 differentially methylated clones were identified and characterized in detail. By sequencing, we found that 29 out of the 33 clones satisfy the criteria of CpG islands, demonstrating that MCA can represent CGIs specifically. Of these 29 clones 5 were already known genes (versican, alpha-tubulin, CSX, OPT homologue and ribosomal RNA gene). Of these, versican is most interesting in that this proteoglycan is an Rb inducible gene, suggesting that down regulation of this gene product may have an important role in colorectal carcinogenesis, where Rb mutations are rare. The data clearly show that aberrant methylation of the versican gene promoter is correlated with silencing of this gene. In addition, methylation of the alpha-tubulin gene in Caco2 is consistent with the results of studying the gene expression profile of colorectal cancers using SAGE, which demonstrated that alpha-tubulin is markedly down-regulated in CRC. Methylation of the CSX and OPT genes does not coincide with their 5' end, and is therefore not expected to silence these genes. It is possible, however, that these CpG islands are associated with alternate transcripts of the genes, or with other nearby genes, which would then be silenced by methylation. Finally, methylation of ribosomal genes has previously been seen in aging tissues and therefore is not surprising to find in cancers. Because some of the clones recovered are in the exon 1 region of expressed genes, identification of new tumor suppressor genes might be facilitated by using MCA/RDA clones as probes for screening cDNA library. Indeed, based on their chromosome location, several clones map to chromosomal regions thought to Harbor TSGs because they are highly deleted in various tumors (e.g., chromosome 1p35, 3p25-26, 7q31, 17q21 and 22q11-Ter).

Example 4

Two Types of Methylation in CRC

Figure 4A:
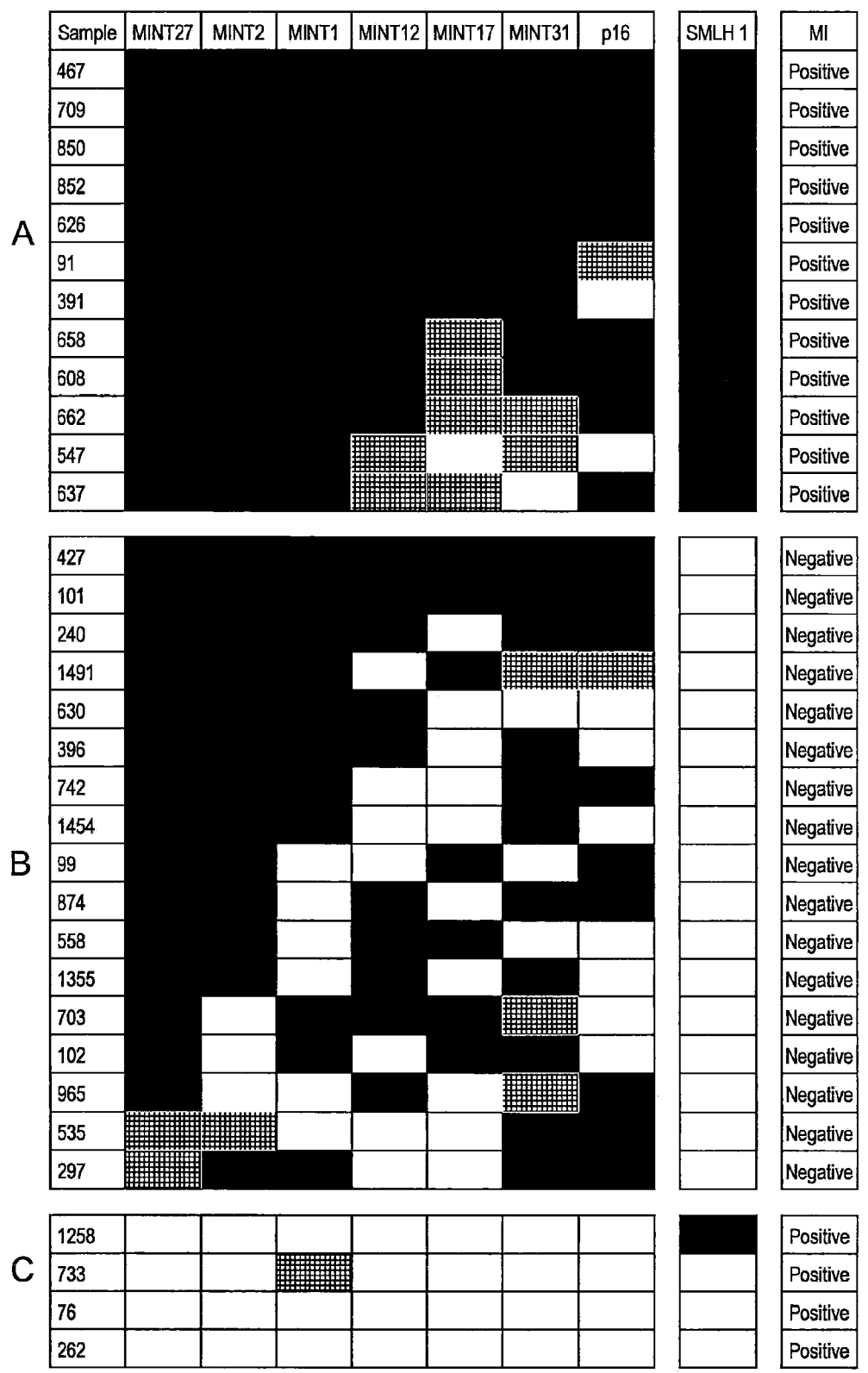

By examining the methylation status of several known genes in colorectal tumors, it has been previously demonstrated that some genes tend to be methylated in an age-dependent manner in normal colon, and are frequently methylated in CRC, while others are methylated in cancers exclusively. To examine this issue on a genome wide level in some detail, the methylation profile of 31 MINT clones in a panel of colorectal tumors and corresponding normal colon mucosa was examined using MCA (two clones could not be accurately studied because of high background (MINT29) or small size (MTNT33)). Because all of theses clones were recovered from a CRC cell line, there was an initial concern that many of these were not representative of methylation in primary (uncultured) tumors. However, of the 31 clones, 29 were also found to be methylated in some primary CRC. The two clones methylated only in the cell line Caco2 were (1) MINT14, a LINE element, and (2) MINT18, a sequence that had a very low CpG frequency and did not qualify as a CGI. Thus, all non-repetitive CGIs recovered were methylated in primary CRC as well as cell lines. Hypermethylation patterns of these 29 clones fell into two distinct categories. A majority of the clones (22 out of 29) were found to be frequently methylated (>70%) in the tumors tested, and a slight amount of methylation was also detected in normal colon mucosa. For all of these clones, the normal colon mucosa obtained from young patients showed less methylation compared to the normal mucosa from older patients (FIG. 4B). Thus, the majority of CGIs hypermethylated in CRC are methylated in normal colon mucosa as well, in an age related manner. This methylation was named Type A for aging-specific methylation.

The remaining 7 clones were methylated exclusively in CRC, and their frequency of methylation was significantly lower than type A methylation (ranging from 10% to 50%). This type of methylation was named type C for cancer-specific.

Recently, several reports have suggested that aberrant methylation of CGIs may play an important role in cancer development. However, there is little integrated information on aberrant CGI methylation in cancer at multiple loci, probably because of the lack of a method to detect methylation in a large number of samples for unselected CGIs throughout the genome. Furthermore, it has been shown that cultured cell lines have a high degree of CGI methylation but it was not known to what extent this reflects methylation in primary cancers. To address these issues, the relatively quantitative and high output features of MCA allowed us to determine the methylation profile of 31 differentially methylated loci in a panel of colorectal carcinomas.

Despite the fact that all sequences were initially recovered from a colon cancer cell line, only 2 out of the 31 clones showed cell line restricted methylation. From the sequence data, one of these two clones was a repeated sequences (LINED, and the other was not a CGI. Thus most of the single copy clones recovered proved to be methylated not only in cell lines but also in some primary colon cancers. Analysis of these 29 clones revealed two distinct types of hypermethylation in cancer (Type A for aging and Type C for cancer), which may have distinct causes, and different roles in cancer development. Type A methylation was seen in the majority of these clones: 22 of 29 (74%) clones were methylated in an age-related manner in normal colon tissue, and hypermethylated at a high frequency in CRC, as we have shown for the ER gene and others. These results suggest that a large number of CGIs in the human genome are incrementally methylated during the aging process and, for many genes, this methylation correlates with reduced gene expression as shown for ER and versican. Although the mechanism of Type A methylation is unknown, it is likely to result from physiological processes rather than a genetic alteration because (1) it is very frequent and affects large numbers of cells, (2) it is present in all individuals, not just patients with cancer and (3) this process is gene and tissue specific. Because the methylation status at a given CGI is thought to be related to positive (methylator) factors and negative (protector) factors, it is possible that for some genes, this balance favors slightly de-novo methylation, and that this is reflected by progressive hypermethylation after repeated cell divisions.

Example 5

Global Hypermethylation in CRC

Figure 5:
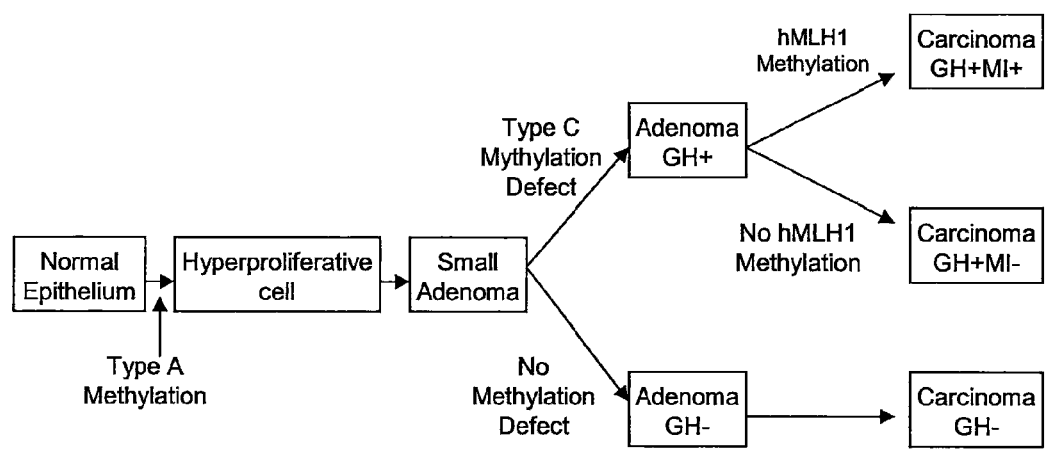
FIG. 5 shows a model integrating CGI methylation in colorectal carcinogenesis.

To understand the patterns of cancer-specific methylation in CRC, the methylation status of all 7 type C clones was analyzed, as well as p16 in primary cancers and polyps (FIG. 4). Two of these clones (MINT1 and MINT2) were studied by both MCA and bisulfite-PCR, and the concordance between the two techniques was found to be 98%. P16 was studied by both MCA and Southern blot, with a concordance rate of 98%. When we considered the six clones that were methylated in more than 10% of the cases, as well as p16, a remarkable pattern emerged (summarized in FIG. 5 and Table 2).

TABLE 2

Percentage of Tumors Methylated at Multiple MINT Loci, p16 and hMLH1

| | TypeC MethylationType | | | | | | | | Type A Methylation | | | | | |
| --- | --- | --- | --- | --- | --- | --- | --- | --- | --- | --- | --- | --- | --- | --- |
| | MINT 1 | MINT 2 | MINT 12 | MINT 17 | MINT 25 | MINT 31 | p16 | hMLH1 | MINT 6 | MINT 8 | MINT 22 | MINT 24 | MINT 30 | MI 3 |
| MI+ Cancer | | | | | | | | | | | | | | |
| EI+ (n = 12) | 100% | 100% | 100% | 92% | 100% | 92% | 83% | 100% | 100% | 100% | 100% | 100% | 100% | 10 |
| EI− (n = 4) | 25% | 0% | 0% | 0% | 0% | 0% | 0% | 25% | 100% | 100% | 100% | 75% | 75% | 50 |
| MI− Cancer | | | | | | | | | | | | | | |
| EI+ (n = 17) | 65% | 82% | 59% | 41% | 100% | 82% | 59% | 0% | 94% | 100% | 100% | 100% | 60% | 93 |
| EI− (n = 17) | 0% | 12% | 0% | 0% | 12% | 0% | 0% | 0% | 82% | 86% | 100% | 82% | 40% | 65 |
| Adenoma | | | | | | | | | | | | | | |
| EI+ (n = 7) | 86% | 86% | 71% | 29% | 86% | 71% | 57% | 0% | 86% | 83% | 100% | 100% | 43% | 86 |
| EI− (n = 8) | 0% | 0% | 0% | 0% | 0% | 13% | 0% | 0% | 50% | 100% | 86% | 50% | 13% | 25 |

The 50 CRC fell into two distinct groups: (1) A group with a high level of Type C methylation, whereby all the tumors had methylation of 4 or more loci simultaneously and (2) a group where methylation of any type C clone is extremely rare. Thus, the first group of tumors appears to display profound global hypermethylation (GH+), which is lacking in the second group (GH−). Interestingly, there was a great concordance between methylation of the p16 gene, which was not selected for by our cloning process, and the presence of GH. In sharp contrast, Type A methylation was not significantly different between GH+ and GH− tumors (Table 2).

GH was also detected in a subset of colorectal adenomas (FIG. 5), suggesting that it is an early event in carcinogenesis. Interestingly, while 5 of 5 small adenomas (<7 mm) were GH−, 6 of 9 large adenomas (>10 mm) were GH+, suggesting that this defect may be acquired in the transition between small and large adenomas. In 6 cases, both an adenoma and a cancer from the same patients were examined. In one of these, GH was detected both in the adenoma and the cancer; in 3 cases, GH was detected in the cancer but not in the adenoma and in 2 cases, GH was detected in neither the adenoma nor the cancer.

By contrast to type A methylation, type C methylation is relatively infrequent in primary CRC, and is never observed in normal colon mucosa. Furthermore, detailed analysis of type C methylation in CRC revealed a striking pattern, suggesting the presence of global hypermethylation in a subset of these tumors: GH positive cases are characterized by frequent and concordant methylation of all type C clones examined, such that each tumor has at least four methylation events. By contrast, type C methylation is virtually non-existent in tumors without GH. This concordance cannot be due to simple experimental variation or artifacts because (1) methylation was verified using separate methods (MCA, bisulfite-PCR and Southern blots), (2) the concordance was not limited to MCA/RDA derived clones since it also affected the p16 and hMLH1 genes, and (3) there was no significant difference in type A methylation between GH+ and GH− tumors. Global hypermethylation appears to be an early event in the development of CRC, being detectable in large pre-neoplastic adenomas. Because many genes are potential candidates for inactivation through promoter methylation, global hypermethylation may have profound pathophysiologic consequences in neoplasia through the simultaneous inactivation of tumor-suppressor genes (such as p16), metastasis-suppressor genes (such as E-cadherin), angiogenesis inhibitors (such as Thrombospondin-1) and others. In fact, our data suggest that global hypermethylation could also result in mismatch repair deficiency through methylation and inactivation of the hMLH1 promoter, and may explain up to 75% of cases of sporadic CRC with microsatellite instability. The causes of type A and type C methylation are probably different because the latter is detected only in a limited number of cases, and the genes affected are different. Because of the remarkable concordance in type C methylation among GH+ cases, it appears likely that these tumors all share a specific defect in the maintenance of the methylation-free state in CGIs. This defect could be either aberrant de-novo methylation (through a mutation in DNA-methyltransferase for example), or loss of protection against de-novo methylation, through the loss of a trans-activating factor. Because DNA-methyltransferase activity is similar in the two groups, the latter hypothesis is more likely. Thus, at least in colorectal cancer, it appears likely that type C methylation (an epigenetic error) is actually caused by a genetic event that results in an increased chance of methylating a subset of CGIs. Ironically, this epigenetic defect may then result in additional genetic lesions through the induction of mismatch-repair deficiency.

Example 6

Microsatellite Instability is Linked to Global Hypermethylation in CRC

In a previous study, a link was reported between microsatellite instability and a hypermethylator phenotype in sporadic CRC. Relatively few mutations in mismatch repair genes have been reported in sporadic MI+ cancers, but hMLH1 methylation has recently been observed in some cases. To determine the relation between global hypermethylation and microsatellite instability in CRC, we measured hMLH1 methylation using bisulfite/PCR in our panel of CRC which had also been previously typed for the presence of microsatellite instability (FIG. 5). hMLH1 was studied by bisulfite-PCR only because it does not have 2 SmaI sites in its CGI. Overall, 16 out of 50 (32%) cancers had evidence of microsatellite instability. Among the 29 GH+ cases, 12 had evidence of hMLH1 methylation, suggesting that hMLH1 is one of the targets of global hypermethylation in CRC. All of these 12 tumors had microsatellite instability. By contrast, hMLH1 methylation was detected in only one of the 21 GH− cases. These data establish a strong link between the GH phenotype, hMLH1 methylation and microsatellite instability in CRC. Two lines of evidence suggest that microsatellite instability may follow, and be caused by, global hypermethylation and hMLH1 methylation. First, GH is detectable in about half of colonic adenomas, but none of these tumors have hMLH1 methylation, and microsatellite instability is extremely rare in this pre-neoplastic lesion. Second, GH is not simply caused by mismatch repair defects because microsatellite instability is absent in more than half of the GH+ cases, and GH was absent in 4 of the 16 cancers with microsatellite instability. Overall, our data suggest that, in sporadic CRC, the majority (12 out of 16, or 75%) of cases with microsatellite instability may be caused by GH followed by hMLH1 methylation, loss of hMLH1 expression and resultant mismatch repair deficiency.

Based on these data, the following model has been developed integrating CGI methylation into CRC development (FIG. 6). In this model, CGI methylation plays two distinct roles, and appears to arise through distinct mechanisms. Initially, type A methylation arises as a function of age in normal colorectal epithelial cells. By affecting genes that regulate the growth and/or differentiation of these cells, such methylation results in a hyperproliferative state, which is thought to precede tumor formation in the colon. Such hyperproliferation is known to arise with age in colorectal epithelium, and to be marked in patients with CRC. The cause of type A methylation is unknown, but without being bound by theory it is possible that it is related to endogenous factors inherent to the structure of DNA, and that it may be modulated by factors such as level of ongoing expression and exposure to carcinogenic insults. Furthermore, modulation of type A methylation may provide one possible explanation for the reduction in CRC tumorigenesis by reducing levels of DNA-methyltransferase. A second major role for CGI methylation appears later, perhaps at the transition between small and large adenomas in the colon. This methylation (type C) affects only a subset of tumors, which then evolve along a pathway of global hypermethylation. This GH leads to cancer development through the simultaneous inactivation of multiple tumor-suppressor genes such as p16, and induction of mismatch repair deficiency through inactivation of hMLH1. The cause of this global hypermethylation is unknown, but may well be related to inactivation of a gene that protects CGIs from de-novo methylation. Finally, we propose that tumors without GH evolve along more classic genetic instability pathways, including chromosomal instability. Interestingly in this regard, Lengauer et al found an inverse correlation between chromosomal instability and MMR deficiency in CRC cell lines.

While based on CRC, this model is applicable to most human malignancies. In evidence has also been found for type A and type C methylation in brain tumors. Preliminary evidence also suggests the presence of global hypermethylation in multiple types of cancers, including stomach cancers, brain tumors and hematopoietic malignancies.

In conclusion, a novel method, MCA, has been developed to selectively amplify methylated CGIs. Using MCA/RDA 33 differentially methylated clones in CRC were isolated. The methylation profile of these clones revealed that nearly all methylation in CRC can be accounted for by (1) age-related methylation and (2) a hypermethylator phenotype presumably caused by global hypermethylation. Deciphering the mechanisms underlying these phenomena should facilitate the early detection, prevention and therapy of cancers, including colorectal cancers.

Example 7

Identification of CACNA1G as a Target for Hypermethylation on Human Chromosome 17q21

To identify genes differentially methylated in colorectal cancer, methylated CpG island amplification was used followed by representational difference analysis (Razin and Cedar, Cell 17: 473-476, 1994, herein incorporated by reference). One of the clones recovered (MINT31, see above) mapped to human chromosome 17q21 using a radiation hybrid panel, and a Blast search revealed this fragment to be completely identical to part of a BAC clone (Genbank: AC004590) sequenced by high throughput genomic sequence. The region surrounding MINT31 fulfills the criteria of a CpG island: GC content 0.67, CpG/GpC ratio 0.78 and a total of 305 CpG sites in a 4 kb region. Using this CpG island and 10 kb of flanking sequences in a Blast analysis, several regions highly homologous to the rat T-type calcium channel gene, CACNA1G, were identified (Perez-Reyes et al., Nature 391; 896-900. 1998, herein incorporated by reference). Several ESTs were also identified in this region. Using Genscan, 2 putative coding sequences (G1, and G2) were identified. Blastp analysis revealed that G1 has a high homology to the EH-domain-binding protein, epsin, while G2 is homologous to a C-elegans hypothetical protein (accession No. 2496828).

The MINT31 CpG island corresponds to the 3' regions of G1 and G2, based on the direction of the open reading frame and the presence of a poly A tail, and is unlikely to influence their transcription. The EST closest to MINT31 (H13333) was sequenced entirely and was found not to contain a continuous open reading frame, but a poly-adenylation signal was identified on one end, along with a poly A tail. These data suggest that H13333 corresponds to the last 2 exons of an unidentified gene. MINT31 is in the intron of this gene and is unlikely to influence its transcription. However, based on both promoter prediction (TSSG) analysis of this region and homology to the rat CACNA1G sequence, the MINT31 CpG island is also in the 5' region of human CACNA1G gene and may play a role in its transcriptional activity.

The human CACNA1G sequence deposited in Genbank lacks the 5' region of the gene, when compared to the rat homologue. To determine the 5' region of human CACNA1G, we amplified cDNA by RT-PCR using primers based on the BAC sequence (Genbank: AC004590, herein incorporated by reference). The PCR products were cloned and sequenced, and the genomic organization of the gene was determined by comparing the newly identified sequences as well as the known sequences to the BAC that covers this region. CACNA1G is composed of 34 exons which span a 70 kb area. Based on sequences deposited in Genbank, the gene has two possible 3' ends caused by alternate splicing. CACNA1G is highly homologous to rat CACNA1G with 93% identity at the protein level, and 89% identity at the nucleotide level. The 5' flanking region of CACNA1G lacks TATA and CAAT boxes, which is similar to many housekeeping genes. A putative TFIID binding site was identified 547-556 bp upstream from the translation start site, and several other potential transcription factor binding sites such as AP1 (1 site), AP2 (2 sites) and SP1 (10 sites), were identified upstream of CACNA1G exon 1 using the promoter prediction program, TESS (data not shown).

The CACNA1G CpG island is 4 kb, and is larger than many typical CpG islands. MINT31 corresponds to the 5' edge of the island while CACNA1G is in the 3' region. It is not known whether large CpG islands such as this are coordinately regulated with regards to protection from methylation, and aberrant methylation in cancer. To address this issue, the methylation status of the 5' region of CACNA1G was studied using bisulfite-PCR of DNA from normal tissues as well as 35 human cancer cell lines from colon, lung, prostate, breast and hematopoietic tumors. The CpG island was divided into 8 regions and their methylation status was examined separately. The genomic DNA was treated with sodium bisulfite and PCR amplified using primers containing no or a minimum number of CpG sites. Methylated alleles were detected by digesting the PCR products using restriction enzymes which specifically cleave sites created or retained due to the presence of methylated CpGs. None of the regions was methylated in normal colon, consistent with a uniform protection against de-novo methylation.

Regions 1 and 2 were frequently methylated in cancer cell lines, and behaved in a concordant manner. These 2 regions were methylated in most cancer cell types except gliomas, and most cell lines where methylation was found methylated both regions simultaneously. Region 3, which is less CG rich than any of the other regions, had either no methylation or very low levels of methylation in most cell lines. Regions 5, 6, and 7 behaved quite differently compared to 1-3. Methylation of these regions was less frequent than regions 1-2, as 22/35 cell lines had no detectable methylation there, despite often showing methylation of region 1-2. However, when methylation was present (in 13/35 cell lines), it affected all 3 regions simultaneously, although to varying extents. Finally, regions 4 and 8 behaved differentially again, being partially methylated primarily in colon and breast cell lines. Therefore, with regards to hypermethylation in cancer, the CpG rich region upstream of CACNA1G appears to be composed of 2 CpG islands which behave independently. MINT31 corresponds to the upstream CpG island (island 1, regions 1 and 2), while the 5' region of CACNA1G is contained in the downstream CpG island (island 2, regions 5-7). Regions 3, 4 and 8 correspond to the edge of these CpG islands, and behave a little differentially than the hearts of the CpG islands, as previously described for the E-Cad gene (Graff, et al., J. Biol. Chem. 272: 22322-22329, 1997).

Overall, the methylation patterns fell into 5 distinct categories: (1) No methylation in any region (normal tissue). (2) Slight methylation of island 1 (6 cell lines, see for example TSU-PRL in FIG. 2). (3) Heavy methylation of island 1 but no methylation of island 2 (16 cell lines, see for example Caco2 in FIG. 2). (4) Heavy methylation of island 1 and moderate to heavy methylation of island 2 (6 cell lines, see for example RKO and Raji in FIG. 2). (5) High methylation of island 1 and low to moderate methylation of island 2 (7 cell lines, see for example MB-231 in FIG. 2).

In a previous study of rat CACNA1G, this gene was shown to be expressed most abundantly in the brain (Perez-Reyes et al., Nature 391: 896-900. 1998). To determine the expression of CACNA1G in normal and neoplastic human cells, RT-PCR was performed using cDNA from various normal tissues and from a panel of 27 tumor cell lines. CACNA1G was expressed ubiquitously in a variety of tissues and cell lines. In normal tissues expression was relatively low but easily detectable, while most cell lines had relatively high expression of CACNA1G. However, some cell lines had negligible or totally absent levels of CACNA1G expression. The results of CACNA1G expression was correlated with the detailed methylation analysis previously described. In this analysis, a remarkable pattern emerged. Methylation of region 1-4 and 8 had no effect on CACNA1G expression. However, there was a strong correlation between methylation of regions 5-7 and expression of the gene. In fact, all cell lines that lack methylation of this region strongly express the gene. All 6 cell lines with pattern 4 methylation studied had no detectable expression. Finally, the 7 cell lines with pattern 5 methylation (examples DLD-1 and MB-453) had variable levels of expression ranging from very low to near normal. The fact that patterns 3 and 5 differ significantly with regards to expression, but are almost identical with regards to methylation of all regions except 7 suggests that this area is important in the inactivation of CACNA1G.

To confirm whether methylation of the 5' CpG island of CACNA1G is really associated with gene inactivation, 3 non-expressing cell lines showing pattern 4 methylation (RKO, SW48 and Raji) and 2 weakly expressing cell lines showing pattern 5 methylation (MB-231 and MB-435) were treated with 1 M of the methyl-transferase inhibitor 5-deoxy-azacitidine. After treatment, all these cell lines re-expressed CACNA1G mRNA. Consistent with re-expression, demethylation of region 7 was observed after 5-deoxy-azacitidine treatment (FIG. 3C).

De novo cytosine methylation is thought to sometimes occur in vitro during cell propagation (Antequera et al., *Cell* 62: 503-514, 1990). To determine whether the methylation of CACNA1G occurs in vivo, primary human tumors were examined for methylation of the 5' region of CACNA1G. Aberrant methylation was detected in 17 out of 49 (35%) colorectal cancers, 4 out of 28 colorectal adenomas (25%), 4 out of 16 (25%) gastric cancers and 3 out of 17 (18%) acute myelogenous leukemia cases. In colorectal cancers, there was a significant correlation between methylation of CACNA1G and methylation of p16 ($p<0.005$) and hMLH1 ($p<0.001$), as well as a strong correlation with the presence of microsatellite instability, and the recently identified CpG island methylator phenotype (CIMP), supporting that CACNA1G is also a target for CIMP in colorectal cancer.

To determine whether aberrant methylation of the 5' region of CACNA1G affects the expression status of this gene in primary tumors, we performed RT-PCR using cDNA from a series of colorectal adenomas. Six out of 8 cases which showed no methylation of region 7 expressed CACNA1G. In sharp contrast, all 5 cases that showed methylation of region 7 had no detectable expression of this gene.

Thus, a human T-type calcium channel gene (CACNA1G) has been identified and cloned using the MINT31 sequence as a probe. The human T-type calcium channel gene has been determined to be a target of aberrant methylation and silencing in human tumors. The data show that MINT31 (a representative sequence of MINT1-33) can be used as a probe to identify genes that play a role in disorders such as cell proliferative disorders.

Detailed analysis of the CpG island upstream of CACNA1G revealed that methylation 300 to 800 bp upstream of the gene closely correlated with transcriptional inactivation. The CACNA1G promoter is contained in a large CG rich area that is not coordinately methylated in cancer. The CpG island around MINT31 is much more frequently methylated in cancers compared to that just upstream of CACNA1G. This may simply be caused by differential susceptibility to de-novo methylation between these two regions, with methylation of MINT31 serving as a trigger, and eventually spreading to CACNA1G, as described in other genes (Graff, et al., *J. Biol. Chem.* 272: 22322-22329, 1997). However, it is likely that these 2 regions are controlled by different mechanisms because (1) cell lines kept in culture for countless generations do not in fact spread methylation from MINT31 to CACNA1G (e.g., Caco2), (2) region 3 that separates the 2 islands is infrequently and sparsely methylated in cancer and (3) 2 cases of primary colorectal cancer were found which are methylated at the CACNA1G promoter but not at MINT31). Therefore, methylation of MINT31 appears to be independent of methylation of CACNA1G suggesting that they are 2 distinct CpG islands regulated by different mechanisms. These data leave open the possibility that MINT31 is the promoter for an unidentified gene, which may perhaps be transcribed opposite to CACNA1G.

Many CpG islands of silenced genes appear to be methylated uniformly and heavily throughout the island (e.g., Graff, et al., *J. Biol. Chem.* 272: 22322-22329, 1997). In contrast the methylation patterns of the 5' region of CACNA1G (region 5-7) was heterogeneous in the cell lines which did not express this gene. Nevertheless, methylation does appear to play a role in CACNA1G repression since demethylation readily reactivates the gene.

The causes of CACNA1G methylation remain to be determined. Methylation was not detected in normal colon mucosa, placenta, normal breast epithelium and normal bone marrow, including samples from aged patients, suggesting that methylation of this region is cancer specific. However, there was a significant correlation between methylation of CACNA1G and other tumor suppressor genes such as p16 and hMLH1. Thus, CACNA1G probably is a target for the recently described CIMP phenotype, which results in a form of epigenetic instability with simultaneous inactivation of multiple genes. It should be noted that a gene identified by the method of the invention (MINT31) has been successfully utilized to identify another gene of interest (CACNA1G) whose methylation pattern correlates with the presence of specific cell proliferative disorders.

T-type calcium channels are involved not only in electrophysiological rhythm generation but also in the control of cytosolic calcium during cell proliferation and cell death (reviewed in Berridge, et al., *Nature* 395: 645-648, 1998). The results demonstrate that the expression of CACNA1G is not limited to brain and heart, suggesting that it may play a role in these other tissues. It has previously been shown that Ca2+ influx via T-type channels is an important factor during the initial stages of cell death such as apoptosis (Berridge, et al., *Nature* 395: 645-648, 1998), ischemia (Fern, *J. Neurosci.* 18: 7232-7243, 1998) and complement-induced cytotoxicity (Newsholme, et al., *Biochem. J.* 295: 773-779, 1993.). These studies determining the methylation status of the CACNA1G suggest that the impairment of voltage gated calcium channels may play an important role in cancer development and progression through altering calcium signaling.

Example 8

Experimental Procedures

Methylated CpG Island Amplification

The procedure is outlined in FIG. 1. Five μg of DNA were digested with 100 units of SmaI for 6 hours (all restriction enzymes were from NEB). The DNA was then digested with 20 units of XmaI for 16 hours. DNA fragments were then precipitated with ethanol. RXMA and RMCA PCR adaptors were prepared by incubation of the oligonucleotides RXMA24 (5'-AGCACTCTCCAGCCTCTCACCGAC-3') (SEQ ID NO: 34) and RXMA12 (5'-CCGGGTCGGTGA-3')

(SEQ ID NO:35), or RMCA24 (5'-CCACCGCCATC-CGAGCCTTTCTGC-3') (SEQ ID NO:36) and RMCA12 (5'-CCGGGCAGAAAG-3') (SEQ ID NO:37) at 65° C. for two min followed by cooling to room temperature. 0.5 µg of DNA was ligated to 0.5 nmol of RXMA or RMCA adaptor using T4 DNA ligase (NEB). PCR was performed using 3 µl of each of the ligation mix as a template in a 100 µl volume containing 100 pmol of RXA24 or RMC24 primer, 5 units of Taq DNA polymerase, (GIBCO-BRL.), 4 mM MgC12, 16 mM of NH4 (S04)2, 10 mg/ml of BSA, and 5% v/v DMSO. The reaction mixture was incubated at 72° C. at 5 min and at 95° C. for 3 min. Samples were then subjected to 25 cycles of amplification consisting of 1 min at 95° C., and 3 min either at 72° C. or 77° C. in a thermal cycler (Hybaid, Inc.). The final extension time was 10 min.

Detection of Aberrant Methylation Using MCA

MCA products from normal colon mucosa and corresponding cancer tissues were prepared as described above. One µg of MCA products was resuspended in 4 µl of TE (10 mM Tris pH 8.0, 1 mM EDTA pH 8.0), mixed with 2 µl of 20×SSC, and 1 µl aliquot of this mix was blotted onto nylon membranes (Nunc) using a 96 well replication system (Nunc). The membranes were baked at 80° C., UV crosslinked for 2 min. and hybridized using $^{32}$P labeled probes. Each sample was blotted in duplicate. Each filter included mixtures of a positive control (Caco2) and a negative control (normal colon mucosa from an 18 year old individual). The filters were exposed to a phosphor screen for 24 to 72 hours and developed using a phosphorimager (Molecular Dynamics). The intensity of each signal was calculated using the Image Quant software, and methylation levels were determined relative to the control samples.

RDA

RDA was performed essentially as previously reported with the following modifications. For the first and second rounds of competitive hybridization, 500 ng and 100 ng of ligation mix was used, respectively. To eliminate the digested adaptor, a cDNA spun column (Amersham) was used instead of excising from the agarose gel. Primers used for the first and second rounds of RDA are as follows:

```
JXMA24    (5' ACCGACGTCGACTATCCATGAACC 3'),
          (SEQ ID NO: 38)

JXMA12    (5' CCGGGGTTCATG 3'),
          (SEQ ID NO: 39)

JMCA24    (5' GTGAGGGTCGGATCTGGCTGGCTC 3'),
          (SEQ ID NO: 40)

JMCA12    (5' CCGGGAGCCAGC 3'),
          (SEQ ID NO: 41)

NXMA24    (5' AGGCAACTGTGCTATCCGAGTGAC 3'),
          (SEQ ID NO: 42)

NXMA12    (5' CCGGGTCACTCG 3'),
          (SEQ ID NO: 43)

NMCA24    (5' GTTAGCGGACACAGGGCGGGTCAC 3'),
          (SEQ ID NO: 44)

NMCA12    (5' CCGGGTGACCCG 3').
          (SEQ ID NO: 45)
```

After the second round of competitive hybridization, PCR products were digested with XmaI. The J adaptor was eliminated by column filtration. The PCR products were then subcloned into Bluescript SK(-) (Stratagene). To screen for inserts, a total of 396 clones were cultured overnight in LB medium with ampicillin and 3 µl of the culture was directly used as template for a PCR reaction. Each clone was amplified with

```
                                          (SEQ ID NO: 46)
T3    (5'-AATTAACCCTCACTAAAGGG-3')
and
                                          (SEQ ID NO: 47)
T7    (5'-GTAATACGACTCACTATAGGGC-3') primers,
``` blotted onto nylon membranes, and screened for cross hybridization with 32P labeled inserts. The clones differentially hybridizing to tester and driver MCA products were further characterized by Southern blot analysis and DNA sequencing.

Southern Blot Analysis.

Five µg of DNA was digested with 20-100 units of restriction enzymes as specified by the manufacturer (NEB). DNA fragments were separated by agarose gel electrophoresis and transferred to a nylon membrane (Zeta-probe, Bio-Rad). Filters were hybridized with 32P-labeled probes and washed at 65° C. with 2×SSC, 0.1% SDS for 10 min. twice, and 0.1× SSC, 0.1% SDS for 20 min. Filters were then exposed to a phosphor screen for 24-72 hours and analyzed by using a phosphorimager (Molecular Dynamics).

DNA Sequencing and Analysis

Plasmid DNA was prepared using the Wizard Plus Minipreps (Promega) according to the suppliers recommendation. Sequence analysis was carried out at the Johns Hopkins Core Sequencing Facility using automated DNA sequencers (Applied Biosystems). Sequence homologies were identified using the BLAST program of the National Center for Biotechnology Information (NCBI) available at ncbi.nlm.nih.gov using the default parameters of the web site. Putative promoter sequences were predicted using the computer programs NNPP and TSSG available through the Baylor college of Medicine launcher at dot.imgen.bcm.tmc.edu:9331.

Bisulfite-Restriction Methylation Analysis

DNA from colon tumors, cell lines and normal colon mucosa was treated with bisulfite as reported previously. Primers used for PCR were as follows:

```
                                          (SEQ ID NO: 56)
hMLH1,      5'-TAGTAGTYGTTTTAGGGAGGGA-3', (SEQ ID NO: 57)
            5'-TCTAAATACTCAACRAAAATACCTT-3';

(SEQ ID NO: 58)
MINT1,      5'-GGGTTGGAGAGTAGGGGAGTT-3', (SEQ ID NO: 59)
            5'-CCATCTAAAATTACCTCRATAACTTA-3';

(SEQ ID NO: 48)
MINT2,      5'-YGTTATGATTTTGTTTAGTTAAT-3', (SEQ ID NO: 49)
            5'-TACACCAACTACCCAACTACCTC-3';

(SEQ ID NO: 50)
Versican,   5'-TTATTAYGTTTTTTATGTGATT-3' (V1), (SEQ ID NO: 51)
            5'-ACCTTCTACCAATTACTTCTTT-3' (V2).
```

Ten to 20 µl of the amplified products were digested with restriction enzymes which distinguish methylated from unmethylated sequences as reported previously, electrophoresed on 3% agarose or 5% acrylamide gels, and visualized by ethidium bromide staining.

RT-PCR

Total RNA was prepared from normal colon epithelium and tumor cell lines using TRIZOL (GIBCO-BRL). To study gene expression following demethylation, cell lines were treated with 1 μM of 5-aza-2'-deoxycytidine for 2-5 days. cDNA was prepared using random hexamers and reverse transcriptase as specified by the manufacturer (Boehringer). The expression of versican was determined by RT-PCR using the primers

```
VF   5'-GCTGCCTATGAAGATGGATTTGAGC-3' (SEQ ID NO: 52)
     and

VR   5'-GGAGTTCCCCCACTGT-TGCCA-3'.   (SEQ ID NO: 53)
```

The PCR products were visualized by ethidium bromide staining. The cDNA samples were also amplified using GAPDH gene, primers

```
GAPF  5'-CGGAGTCAACGGATTGGTCGTAT-3' (SEQ ID NO: 54)
      and

GAPR  5'-AGCCTTCTCCATGGTGGTGAAGAC-3'(SEQ ID NO: 55)
``` as a control for RNA integrity. All reactions were performed using RT (−) controls where the reverse transcriptase enzyme was omitted.

Chromosomal Mapping

The chromosomal location of clones that did not correspond to known genes was determined using a human-rodent somatic cell hybrid panel and a radiation hybrid panel (Research Genetics). PCR reactions were performed using 30 ng of each of the hybrid panel DNA as a template in a 40 μl volume containing 15 pmol of each primer, 0.5 units of Taq DNA polymerase, (GIBCO BRL), 2 mM MgC12, BSA and 5% DMSO. First denaturation was carried out at 95° C. for 3 min. Samples were then subjected to 35 cycles of amplification consisting of 25 sec. at 94° C., 1 min at 60 to 68° C. and 1.5 min. at 72° C. in a thermal cycler (Hybaid). The final extension time was 10 min. Ten μl of the PCR product were electrophoresed in a 2% agarose and the genotype of each panel was determined. Linkage analysis was performed using the RH server of Stanford University as described.

Although the invention has been described with reference to the presently preferred embodiment, it should be understood that various modifications can be made without departing from the spirit of the invention. Accordingly, the invention is limited only by the following claims.

What is claimed is:

1. A kit comprising a carrier means containing one or more containers comprising a membrane, wherein the membrane has a nucleic acid sequence, and the nucleic acid sequence is selected from the group consisting of SEQ ID NO: 1, SEQ ID NO:2, SEQ ID NO:4, SEQ ID NO:6, SEQ ID NO:8, SEQ ID NO: 9, SEQ ID NO:10, SEQ ID NO:14, SEQ ID NO:15, SEQ ID NO:17, SEQ ID NO:19, SEQ ID NO:20, SEQ ID NO:22, SEQ ID NO:23, SEQ ID NO:24, SEQ ID NO:25, SEQ ID NO:27, SEQ ID NO:30, SEQ ID NO:31, SEQ ID NO:32, and SEQ ID NO:33 (MINT1, MINT2, MINT4, MINT6, MINT5, MINT 9, MINT10, MINT14, MINT15, MINT17, MINT19, MINT20, MINT22, MINT23, MINT24, MINT25, MINT27, MINT30, MINT31, MINT32, and MINT33) and is immobilized on the membrane.

2. An isolated nucleic acid selected from the group consisting of SEQ ID NO: 1, SEQ ID NO:2, SEQ ID NO:4, SEQ ID NO:6, SEQ ID NO:8, SEQ ID NO: 9, SEQ ID NO:10, SEQ ID NO:14, SEQ ID NO:15, SEQ ID NO:17, SEQ ID NO:19, SEQ ID NO:20, SEQ ID NO:22, SEQ ID NO:23, SEQ ID NO:24, SEQ ID NO:25, SEQ ID NO:27, SEQ ID NO:30, SEQ ID NO:31, SEQ ID NO:32, SEQ ID NO:33 (MINT1, MINT2, MINT4, MINT6, MINT8, MINT 9, MINT10, MINT14, MINT15, MINT17, MINT19, MINT20, MINT22, MINT23, MINT24, MINT25, MINT27, MINT30, MINT31, MINT32, and MINT33).

3. The nucleic acid of claim 2, wherein the nucleic acid is methylated.

4. The nucleic acid of claim 3, wherein said nucleic acid is unmethylated.

5. The nucleic acid of claim 2, wherein the nucleic acid is operatively linked to an expression control sequence.

6. The nucleic acid of claim 5, wherein the expression control sequence is a promoter.

7. The nucleic acid of claim 6, wherein the promoter is tissue specific.

8. An expression vector containing the nucleic acid of claim 2.

9. The vector of claim 8, wherein the vector is a plasmid.

10. The vector of claim 8, wherein the vector is a viral vector.

11. The vector of claim 10, wherein the viral vector is a retroviral vector.

12. A host cell containing the vector of claim 8.

13. The host cell of claim 12, wherein the cell is an eukaryotic cell.

14. The host cell of claim 12, wherein the cell is a prokaryotic cell.

15. An isolated nucleic acid sequence comprising at least one methylated CpG dinucleotide, wherein the isolated nucleic acid sequence is selected from the group consisting of SEQ ID NOs: 1-15 and 17-33.

* * * * *

SEQUENCE LISTING

```
<160> NUMBER OF SEQ ID NOS: 59

<210> SEQ ID NO 1
<211> LENGTH: 528
<212> TYPE: DNA
<213> ORGANISM: Artificial Sequence
<220> FEATURE:
<223> OTHER INFORMATION: Synthetic construct: methylated gene MINT1
<220> FEATURE:
<221> NAME/KEY: misc_feature
<222> LOCATION: (1)...(528)
<223> OTHER INFORMATION: n = A,T,C or G

<400> SEQUENCE: 1
cccgggctgg gtacctggac ctataccttc atagctgcct taggctcaac ttttcggcgg      60
ggatccctct gcagacgtgc aggtggcggg agagcagagg tagccgcagt aagtgctgag     120
agagcctgaa agaaacacca tgaattttca aactctccca catacattcc cgaagcgcct     180
gtctggcgtc taagagagag caagagaggg ctggagagca ggggagcccg cggggctgag     240
gctctttgtc agcgcctgca cttcctacgt tacaacgcct tcattcagca aaaaccttt      300 gggcgcctgc tgtgcgccag gccaggcgaa gnagaccgag gntgtgaagc tcagagggga     360
gagggaccaa tcgcagtaaa taagctaccg aggtaatctt agatggngat gagggcagga     420
aaagncatca gncgacctct gacctttctc ttagggggtt ttccccttcc gcctgggttc     480
tagaactggg aaganttttc tccagagcgt cgcggggagc gccccggg                  528

<210> SEQ ID NO 2
<211> LENGTH: 562
<212> TYPE: DNA
<213> ORGANISM: Artificial Sequence
<220> FEATURE:
<223> OTHER INFORMATION: Synthetic construct: methylated gene MINT2

<400> SEQUENCE: 2
cccgggcgct gccaaatgta aacaatccgc catgatttct ttgtttagct aatcgaacct      60
gccgccgtct cgagtcccag gcgctccctc tcccttctct ccccttcccc cctcgcgctc     120
```

```
tcttttattt atttatttgt ctctccccc accccgccct tagtctttcc ctctctttag      180
tcttagtagc tgcttttaat ggaagtcgag gcagttgggt agttggtgca gggagtgcgg      240
tggtggtttt tataaataca ggtaaaataa tacccaaatt tcaggctgag gtgcagtttc      300
ttggaagagg aggagggtgt tcctctcctt ccctccctct ttccccctcc cccgtttatt      360
agagtatcct cggtggaaag tgccagaaaa atgtgctgca tctctgagtc acctttctt       420 cccgccgaac tctagcaccc aagttcgctg gcggattttg gactctgcca aagtgctgag      480
ttcgtcgttt actttgaaag cctgaaatat aactgatgtc caactgcaga aaggcgcacg      540
gaatcgccgc caccatcccg gg                                                562

<210> SEQ ID NO 3
<211> LENGTH: 563
<212> TYPE: DNA
<213> ORGANISM: Artificial Sequence
<220> FEATURE:
<223> OTHER INFORMATION: Synthetic construct: methylated gene MINT3
<220> FEATURE:
<221> NAME/KEY: misc_feature
<222> LOCATION: (1)...(563)
<223> OTHER INFORMATION: n = A,T,C or G

<400> SEQUENCE: 3
cccgggtttc cagcttctcc cttccacctt tgtctcccct ccctcctaca aactttcagc       60
cttcagtctg ttgggggnta agatctggga aataagcgtg tgtgtccgag tgccttaggg      120
tctgctgtga gcctgaatgc gagtccggtt ggttgtgcag ttatgaacct gtgtgtacat      180
ctgtgtgcct aagacgctgg gcaactgtac ccacatgacc gatgtgtgtg aacgactgtg      240
tgcctgtgtg tctggatctg cgcgtgggtg tagttcgtgt ggctgtgtaa accgcatgca      300
taggtataca tgtacctatg tctcaggctg tgtgcgtcct actgcgatgg tacgagagtg      360
tgggtgtgat ggtgtatgtg atcctgtgtc tgcgtgtccg tacatttgag tgggtgttgt      420
gcgtgtgact gtgtaaactg cgaacatgta cgtgtgcccg cccgtaggta ttaccgtgta      480
cgtgtgtctc cgtgtgcctg tgaggggtgg ggtctgcgcg gggattcccg accccccac      540 actcacaccc tccaagcccc ggg                                                563

<210> SEQ ID NO 4
<211> LENGTH: 481
<212> TYPE: DNA
<213> ORGANISM: Artificial Sequence
<220> FEATURE:
<223> OTHER INFORMATION: Synthetic construct: methylated gene MINT4
<220> FEATURE:
<221> NAME/KEY: misc_feature
<222> LOCATION: (1)...(481)
<223> OTHER INFORMATION: n = A,T,C or G

<400> SEQUENCE: 4
cccgggcctc tggccctctg cgtctgctag nctctttccc ccaagactcc ccgaggtggg       60
gagagnactg gtgntccctg gagaaatcaa ggtgtccaac attctctccg aggcgaggct      120
gcttgagcgc cagcaacagg ncctgctgaa ctttcttccc cggctcctac gctccggttg      180
ctctccatcc tcatttctgg ggtcaaatgg naaagaggga atactcctcg accccctctcc      240 cccttgacta tccaaagcag cccgaagttg gcgaggagac tctgccgggt gtncgggcaa      300
atgncccgcc gggtggctcc agaaatggnc tgtganctgc actcgcctcg gagaaattcc      360
aactcttggt tgaagactct gactcagagg agccctctga ggatgcgccc ctggagaaag      420
ngcacgggag ggaaagtgga gagaactcgn cctccccagg ggctagncag ctactcccgg      480
``` g   481

<210> SEQ ID NO 5
<211> LENGTH: 852
<212> TYPE: DNA
<213> ORGANISM: Artificial Sequence
<220> FEATURE:
<223> OTHER INFORMATION: Synthetic construct: methylated gene MINT5
<220> FEATURE:
<221> NAME/KEY: misc_feature
<222> LOCATION: (1)...(852)
<223> OTHER INFORMATION: n = A,T,C or G

<400> SEQUENCE: 5

```
cccgggtaag tgagccctgc tgcactcccg caccccctctt ccccatgccc accctccggg    60
gatgcaacac cctgttccca tggaacacgg gggttggcag tcacactgtc cccacccagc   120
ttcaggcttg gtctcctcta ggtttgcctt ctgaggaagc agtcccaggg catttactga   180
ccaancagaa aacaggggtt gggaaaagtg agtaggtggg tctgcaaccg ttacaatcac   240
atcactttat tcttaattcg agtatataag gattggcatc atantgggat gangaaggtt   300
actgtccttg tcatttgggc aaaagacccc tacccatatc tcaatgacca attcctcana   360
agtgtcctct tggaanaanc tganttttcc cctccgtaan tccttaacac tctccggctt   420
cccctcaatc ccaggccttc ccctattga cctcaagacc tcctttaatc ccaaagagnc   480
gttgacttcc nccaaatgcg ggtgctttcc tttccaatca agaatatgtt taaaaccct   540 cccagggagt atggactatg tccccaattt taaaagatgg aggaacaaag gcccattggt   600
atgctaaaaa ccatgggaac aggatccaga tttcccccca tcaattcgan ctgccagtct   660
gtcctcggag atcctttgac ttcttggaat anccttttg tgttgtggtt tggggggttga   720 tcttggagaa cttttttgtg tgtcttttaa aaaatgtttc attngttaac tttccaagtg   780
atgctctgat tggagcaatc tcaacaccaa gaagagtagg gaaagaagca gcggnggtcc   840
tgggtccccg gg                                                        852
```

<210> SEQ ID NO 6
<211> LENGTH: 400
<212> TYPE: DNA
<213> ORGANISM: Artificial Sequence
<220> FEATURE:
<223> OTHER INFORMATION: Synthetic construct: methylated gene MINT6
<220> FEATURE:
<221> NAME/KEY: misc_feature
<222> LOCATION: (1)...(400)
<223> OTHER INFORMATION: n = A,T,C or G

<400> SEQUENCE: 6

```
cccgggccct cagaggccgc accacctatt gtgttccagg ctcgcaggaa gccagacctt    60
gcgagaggtg tgtgggggcg gagagtggca caggtttgac actgcaggtc ggaggaggaa   120
gacagtggct gcaaaggcaa aatcgggtgt tattttccca agagtcccctt cagcgtgagt   180 gccggggtca gctcgaactg gagccctgaa tttgtgagtg cgagtgggga gcagcaggag   240
gatccttttc ataggtgagg tcccaggaac gagcctggtc ngtgcttagg caaaggccct   300
tcccacttgt cagccttgtt gtttacccat ccctgcttc tcccagactt gcattaattc   360
cgnngtcggt tccatcaacc ccggnatccc ctcccccggg                          400
```

<210> SEQ ID NO 7
<211> LENGTH: 481
<212> TYPE: DNA
<213> ORGANISM: Artificial Sequence

```
<220> FEATURE:
<223> OTHER INFORMATION: Synthetic construct: methylated gene MINT7

<400> SEQUENCE: 7
cccgggaccc gcccagaacg ctttcgtggg gttggagagg gcaggacaca gcctctctgg      60
gcccggtagt atgcgaagac acgcataacg caaaaggatt cccgtcctgg actttgggaa    120
ttaaggccct gaacacattg agcaaaaagt agatctgtct gtacagacgt ttctttccac    180
gtctttcata gtaaggactt tattaaaaag caggcactcg aatcctaggt gggtagatgg    240
gaggctgggg ctggggatgg ggacgtcctc tgttttctgg ttgtgcacat taaaaataac    300
tctctgctgc ctactcctaa acgcagccgg caaaaatgag acgtcaacta agcgccgttt    360
cagtcccaga gccaggtcgt ccatgggggt tttcaagcgt tttctcgatg actgattttt    420
ctagaagcga atggatttta ttctcccagg tgtaaaggct acctcctgct tcacacccgg    480
g                                                                   481

<210> SEQ ID NO 8
<211> LENGTH: 617
<212> TYPE: DNA
<213> ORGANISM: Artificial Sequence
<220> FEATURE:
<223> OTHER INFORMATION: Synthetic construct: methylated gene MINT8
<220> FEATURE:
<221> NAME/KEY: misc_feature
<222> LOCATION: (1)...(617)
<223> OTHER INFORMATION: n = A,T,C or G

<400> SEQUENCE: 8
cccgggctgt ggcggtgcaa ctcccgccgc ctgcgttcta gacagaaaag ccccttctga      60
ccatgcatta gtagtactac tccattattc ctgttagaac aagttaaaag taagggttga    120
gcccaaaggc cccaggaggg gggtcatgtg cgccccagtc actcaggctc cctcgcttc    180
tccggttcga gttatgccat caagctaata tattgtgact gctcttctct cctgtgacaa    240
aaggcttgca gctgcctcca aatcaataga ttgtcaaaga aatattgaaa acaatcatga    300
cacaaaaact taatcctggn ttggaggcta cataatcaga aattgtgcta cttgttcttc    360
caagncaccc gatttaattt atccccaaac ttttaggcaa attttttattt cccgggacct    420
ttttcccagc agatcctgct acgtctgtcg ggtttgtaat gtaatttgta attnctnccc    480
ttcatgtggt ccggtgcctt gaaccatctt taattaaaag cataattaag ggaagatcta    540
aagaaagaca attaccagat ggtcttttt ttagaggcgg tagttgcgca gagaggggct    600
cggggtctgt ccccggg                                                  617

<210> SEQ ID NO 9
<211> LENGTH: 605
<212> TYPE: DNA
<213> ORGANISM: Artificial Sequence
<220> FEATURE:
<223> OTHER INFORMATION: Synthetic construct: methylated gene MINT9
<220> FEATURE:
<221> NAME/KEY: misc_feature
<222> LOCATION: (1)...(605)
<223> OTHER INFORMATION: n = A,T,C or G

<400> SEQUENCE: 9
cccgggtcat tgtccatctc cgaccagggg agtagccacc cccactagcc agccgtcttt      60
atctcctaga aggggaggtt acctcttcaa atgaggaggc cccccagtcc tgttcctcca    120
ccagccccac tacggaatgg gagcgcattt tagggtggtt actctgaaac aaggagggcc    180
taggaatcta agagtgtgaa gagtagagag gaagtacctc tacccaccag cccacccagt    240
```

```
ccctctctca gcagtggatg gggatggggt gggggtaggg acgagaaggc agctggtgga     300
gaaacagctt caagactctt tgggttcctc ctgctctcca ggggagctta cctggggcta     360
actttagaca cacaggtttg gagggaggaa agaaggaaga attcttttac aacgaatcaa     420
ttaagagcac ttcctctttt cttaacttgg gggagggcc aggaaaactt cttgagtcaa      480
gaaatcttgg gaggnagaca tcagatgtng gcaagaggca gacagatttt gggaaggcag     540
gctttgggtc aanaaagatc aagcctgtgt tgtccccagg ctcttccctg ttcccccatc     600
ccggg                                                                 605

<210> SEQ ID NO 10
<211> LENGTH: 608
<212> TYPE: DNA
<213> ORGANISM: Artificial Sequence
<220> FEATURE:
<223> OTHER INFORMATION: Synthetic construct: methylated gene MINT10
<220> FEATURE:
<221> NAME/KEY: misc_feature
<222> LOCATION: (1)...(608)
<223> OTHER INFORMATION: n = A,T,C or G

<400> SEQUENCE: 10
cccgggggct gcagaatcag gagtcttcnc ctaggtttgg ccttgggctc catcctacnc       60
cctgaatgtg acngctgcgt cttcgtccca cacctacttt tgaatgccaa gaggggggctc     120 cgctggccag gacngaatat ttttatggta aaaaatgacc ggcagttgca tcagctccag     180
gagggtggga gccgtcaccc gaggtcgcac aggcagactg atgaaaattc tgcttataaa     240
gtcactgctc ccccattaat tagggggggag ggggcgctcc ggagccacca cgcacctcgc    300
ccacggncaa aaagcttgtc aacatttttcc acgaaggatt gaaaatgtaa attaactttc    360
agattattca atgtcaccaa ggtatggaaa aaggtcgcca tactgggtgt catttatctc    420
gttgtggatt taaagagctt tttctattaa atttcttaaa attaatgttt tatgttgctc    480
agagtaattt aaacaattat gggcttaaag aattgatcat tacagcccct gggatttagc    540
gctgcaggct gatnnccctg aaaaacctct gatttatcag ggntcgtatt nggccgggca    600
agcccggg                                                              608

<210> SEQ ID NO 11
<211> LENGTH: 636
<212> TYPE: DNA
<213> ORGANISM: Artificial Sequence
<220> FEATURE:
<223> OTHER INFORMATION: Synthetic construct: methylated gene MINT11
<220> FEATURE:
<221> NAME/KEY: misc_feature
<222> LOCATION: (1)...(636)
<223> OTHER INFORMATION: n = A,T,C or G

<400> SEQUENCE: 11
cccgggagtg gctaaccagg aanannaggc actgnccaca caccangggc tgggaaatca       60
agtggcctgc accaaggcgg cttcggggga cttgtctgtg gcaagtcttg gtagtcccca     120
ttcaaacttt tgcctcgagc gtgttaagaa caacaacaaa aaaaaaatca aagtgccaaa    180
ggtccctctc ttctctccag ctcaagaacc caccactttt ctatgatttc tttacaattt    240
attccctccc ttccccaat tccgttagtc actttacccc cacccaccc tgggtttctt      300 ttgtctgaat cttttttcaac accaaggtcc ctctgtatgc ctctccccaa aagcccttat    360
gaaaagttac ctgcattttt taagtgccta catttcttaa cttcgcctaa cagctctttg     420
ccttaattaa agccttctac caattgcttc ttttttctaa gctcgcgggt ttttttcaat     480
```

```
aagttttttg tttttgtttt ttaaggggggg aacaaaagaa acgtgattac cttggaaggc      540
ggcttattgc agtttggggg gaaaattcac tgcagcgctg cgcgactggg ttcggcgttg      600
cccaggcggg tcacatagga agcgtggtgg cccggg                                636
```

<210> SEQ ID NO 12
<211> LENGTH: 552
<212> TYPE: DNA
<213> ORGANISM: Artificial Sequence
<220> FEATURE:
<223> OTHER INFORMATION: Synthetic construct: methylated gene MINT12
<220> FEATURE:
<221> NAME/KEY: misc_feature
<222> LOCATION: (1)...(552)
<223> OTHER INFORMATION: n = A,T,C or G

<400> SEQUENCE: 12

```
cccgggtccc agccctgagg accaggtttc agggctcaga agactccagc gaggttccct      60
cgcagattgt gtctgcggtc gttggggggag gggccccgca gccttcagca gattatccaa     120
aggtcagtga cccagatatg gttttggnca cgggccatgt ttcacttcct gtgcccaag       180 cagaatttag ctgaataatt cggaccccaa accaaacaaa acgctcttat ttccgtttgg      240
ggattcttcg gagttgggat ttttctgtct caaattagaa taatntgcat tattaaccaa     300
cttaacattt atttgttggt tggctgcctg acctttctga gcctcagttt nttcgtctgt     360
aaattgggag cttacccagg tcggaggact gttggaattg gaaatattcg aataaggaag    420 tgttttttgca agtgctttgt aagcagcaaa gcgcttcttc aggggtcaat ttttttttagc   480 tctgcagtca ccacccaaat tcggaagatc gttgtgcctt tcttggatga gaatgcccgg    540
ctccagcccg gg                                                         552
```

<210> SEQ ID NO 13
<211> LENGTH: 313
<212> TYPE: DNA
<213> ORGANISM: Artificial Sequence
<220> FEATURE:
<223> OTHER INFORMATION: Synthetic construct: methylated gene MINT13
<220> FEATURE:
<221> NAME/KEY: misc_feature
<222> LOCATION: (1)...(313)
<223> OTHER INFORMATION: n = A,T,C or G

<400> SEQUENCE: 13

```
cccgggtgtg tgttgttccc ctccatgtac cacgtgtttg tcctgatggt ctcctacccc      60 ctgtcccct gagaggccct ggtgtgtgtt gttccctcc atgtatccac gtgtttgtcc       120
tgatggtctc ctaccccccg tcccctgag aggccctggt gtgtgttgtt ccctccatg       180 tacccacgtg tttgtcctga tgctctccta ccccctgtcc cctgagagg ccctggtgtg    240 tgttgttccc ctccatgtac ccacgtgttt gtcctgatgc tctcctaccc cctgtccccc    300 tgananggccc ggg                                                       313
```

<210> SEQ ID NO 14
<211> LENGTH: 620
<212> TYPE: DNA
<213> ORGANISM: Artificial Sequence
<220> FEATURE:
<223> OTHER INFORMATION: Synthetic construct: methylated gene MINT14
<220> FEATURE:
<221> NAME/KEY: misc_feature
<222> LOCATION: (1)...(620)
<223> OTHER INFORMATION: n = A,T,C or G

<400> SEQUENCE: 14

```
cccgggagtg gccctgcctg gccatttgct caagcagcat gcaagccgga tctacagccg    60
gtgcaccttg ttccttgttc ttccgggcac cggaggccca cgtgaaacct ctcagaggag   120
agcgaagaag gccaccttc atctcaatga gccaacagcc tcacatcctt aagtcctgcc   180
taatcttacg agtcatgagt catcgcttct tccccgccaa gtcattcagg attcagtgac   240
tccagctgcc ctcaggatct gacgaatct tgaaggcaga gttccgagac tgcagtccag   300
gatagagaag ccccggctc catcagggc tcctcggctt caaggcagga cccacccccaa   360 agctntcaaa gcgcagagg cctgttttca ggtctatttt taaagatntc taggggaagt   420
ggtttctgaa tgctctgtag gatgaggctg tgaacagtga ttgtttcatt tgctcggggc   480
tggcaaaaaa gggatgtaca acccgttctg accacaccag tgagttaaaa agcactgcag   540
actatgaata cctttgcca gttggactgg ttatgggac cgatggcttc ccctacaact   600
ggggaggctg ccagcccggg                                              620

<210> SEQ ID NO 15
<211> LENGTH: 641
<212> TYPE: DNA
<213> ORGANISM: Artificial Sequence
<220> FEATURE:
<223> OTHER INFORMATION: Synthetic construct: methylated gene MINT15
<220> FEATURE:
<221> NAME/KEY: misc_feature
<222> LOCATION: (1)...(641)
<223> OTHER INFORMATION: n = A,T,C or G

<400> SEQUENCE: 15
cccgggacct ctgcggttac ctgggccttc cctgccagcc ccacccccct gccccccacca    60 gaaagcgttt acaggacagg tgaggcccgc aggaggaaaa gcactcccct ggcgcaacat   120
gactccagcg catctgcgtc taagccacac cgtgctcctg gtagattaaa aattaattct   180
aaaaaaaaaa tctctcctat cccaaatgca ctgtttctg ccttgcttga caattgattt    240
gtttttaaag gaaagttatg ggtagatcct cttttttctt tcccattctt tnnttcttct   300
tttatactgg agggagggaa acggaggcga ggacacacac gcgcaggcag gggntgaaaa   360
ggccgaggtg ggtttttcctg tttaatatca aaggagggcg ataatgggt ttcctcggtc   420 cggctaggcc ggccttttgac tcaattggaa atgcaaaggc agcttttgcc tattntctgg   480
ctgctggctg agaccctaaa tttccgtagg aaatcgtcgg acacgcactt aatcggnctt   540
tgcaancttt ccctcgaagt tgcacgcggg tctgggcgga ggaggcgagg taaccctgga   600
ttcgaaccag cgcctttctc tccttcaggc ctccgcccgg g                      641

<210> SEQ ID NO 16
<211> LENGTH: 664
<212> TYPE: DNA
<213> ORGANISM: Artificial Sequence
<220> FEATURE:
<223> OTHER INFORMATION: Synthetic construct: methylated gene MINT16

<400> SEQUENCE: 16
cccgggacaa ggcgggtcac ctctggggcc tcaccgcagt ccacttcct ttctcgggta    60 tttggaaacc gtcaccccgc catttcggtg tgggaagagc gcgcgggccc tgccggactt   120
tagtgcttta ggggttaatt tcgggctgac agggacggaa cctaaggcag tgagcgcccc   180
agtaccctca aaccttattg ctggcccctg ctgtctgagc ttacaagcat taccgccgct   240
atttccgtgc gggctgacac gggagatgaa agtggtgaag acaccagggg tgcggggtg    300 gaggtgggga gaggagccag atgggattga tccccagagc cagatgggat ttaaaggtga   360
```

```
gggaggaggg catcctgatg gcgtgtggtc agttgatgcc agattggatg gctgagacac    420
ctctgcagct tacaggaaag acagagggaa agggttctat gaattctagc tgttcatact    480
caaagcaaat aattaatcaa gtggggggg ggcctctagc tgtaaaccca tacctctagg     540
aaaccttttg tcatgtggag ccacagtgct cacttgacag attccccact gagaagtggg    600
ctaagaggtt ggcctgcatt gctgggtgcc tccaggtggg gagtcctgta cctgggagcc    660
cggg                                                                 664
```

<210> SEQ ID NO 17
<211> LENGTH: 490
<212> TYPE: DNA
<213> ORGANISM: Artificial Sequence
<220> FEATURE:
<223> OTHER INFORMATION: Synthetic construct: methylated gene MINT17
<220> FEATURE:
<221> NAME/KEY: misc_feature
<222> LOCATION: (1)...(490)
<223> OTHER INFORMATION: n = A,T,C or G

<400> SEQUENCE: 17

```
cccgggcgcc gggggtccca tccacttctc cctaccttct ctctctcctg ttggagaggc     60
caggggctcc cgcgactgaa aggggccagg ctgaggctgc ccaatcccag ggacaggaag    120 aacatttgg atggatcgcg gggtgcagaa aaaggaagtt gagcgacaga cgcnaagccc    180
aaagcgtgga atttgggaag aggcagaaaa aaagtgggcg aagaggaaga gaaaaaacna    240
gcnacgagat ggggagggac aagaagtttg gggaggatag agaaaaagag aaactgcctg    300
gaaaacaagt tgcaagacaa ttgaaaagtt gaatgagaag gaaaganagg aaggtngtna    360
aatcaaatta gaactgttgg aaaaganggc tgggacacgg cttctctgg ttctgtcctc     420 ccaagaaatt ggaaacctct ccccttcccg gcaccaanct tncgggatgt tccggtgccc    480
ctcccccggg                                                           490
```

<210> SEQ ID NO 18
<211> LENGTH: 435
<212> TYPE: DNA
<213> ORGANISM: Artificial Sequence
<220> FEATURE:
<223> OTHER INFORMATION: Synthetic construct: methylated gene MINT18
<220> FEATURE:
<221> NAME/KEY: misc_feature
<222> LOCATION: (1)...(435)
<223> OTHER INFORMATION: n = A,T,C or G

<400> SEQUENCE: 18

```
cccgggagtg ctcctgccgg cagcatgtcc acttgctagg ggcagagggg cagtgggagt     60
gtcccccatg tgccagcctg tccccacact tgggttaacc ttcagtcacc aggaggaata    120
aggtgtgaca cctctgagac tgtgggcaca tgtgctgctg cctgacagtc acaggctgta    180
ctgtgccagt gacagaggcc atgatgccca cataacccaa acccgaaccc gaaccctaac    240 ccctaaccc taaccctaac cctacccta ccctaaccca gccctaactc tagccctagc      300
cctagcccta gccctaagcc ctaagccctt aagcctaacc ccaaaccccc aaccccaacc    360
ccnaacccta accctaacc cttccctcaa gcctctcnaa ccctgcttgg gtttacaagg    420
ttattnaacc ccggg                                                     435
```

<210> SEQ ID NO 19
<211> LENGTH: 443
<212> TYPE: DNA
<213> ORGANISM: Artificial Sequence
<220> FEATURE:
<223> OTHER INFORMATION: methylated gene: MINT19

<400> SEQUENCE: 19

| | | | | | |
|---|---|---|---|---|---|
| cccgggattg | gtcttttggc | tgggatgtaa | aggaggagga | actagctggg | gaaaggctgg | 60 |
| gtaaggggga | aaacccaggg | aatttaaccc | cctcttctgt | aaaatgagaa | cccattcatt | 120 |
| cacttagcaa | atctttatgg | agctctgtag | gggccctggg | ggaaggcgac | cagagtgtct | 180 |
| gaaagcaaag | agcaggagag | tgtggactca | gctgagagga | gagcagaggc | tgagtgtcag | 240 |
| ggtggggagt | gggaaggggt | ttccaggtgc | caacaaggac | acaagccaag | gtgttgcagt | 300 |
| agggcatttg | gggaacgtat | gagaagcgct | cctgccagct | tccctggcgg | tgtcctattc | 360 |
| cctgcatcca | ttttggacca | tgagccccct | ctcttaccct | ctggccagga | ccgaatgcca | 420 |
| tagacttccc | cagattgccc | ggg | | | | 443 |

<210> SEQ ID NO 20
<211> LENGTH: 510
<212> TYPE: DNA
<213> ORGANISM: Artificial Sequence
<220> FEATURE:
<223> OTHER INFORMATION: Synthetic construct: methylated gene MINT20

<400> SEQUENCE: 20

| | | | | | |
|---|---|---|---|---|---|
| cccgggcccc | agggcggccc | gaaccccagc | caagccggcc | agcagcaggg | ccaacagaag | 60 |
| cagaagcgcc | accggacgcg | cttcaccccc | gcacagctca | acgagttgga | gaggagcttc | 120 |
| gccaagactc | actaccccga | catctttatg | cgtgaggagc | tggcactgcg | tatcgggctg | 180 |
| accgagtccc | gagtgcaggt | acgaggggct | tgggatctgg | gacagaaggc | aaggacaggg | 240 |
| cgggaggatt | tgggcaaagg | gagcagggtc | ttcccttccc | ctgtcgagat | cctgggctgc | 300 |
| tttcaggctg | cctgtgcgtt | cctgtatcga | gttatctcca | tctctacccg | gaaactggtc | 360 |
| cccatcgcca | tccccaatg | gacacgcaag | gcccgtctcc | ggccagtata | gcgacatccc | 420 |
| ggaagaagct | cctcaaaatc | gaagcccggc | gttgtcgggc | tacagggctc | gcctcctccg | 480 |
| cctgagaagg | caacctcagc | gccccccggg | | | | 510 |

<210> SEQ ID NO 21
<211> LENGTH: 410
<212> TYPE: DNA
<213> ORGANISM: Artificial Sequence
<220> FEATURE:
<223> OTHER INFORMATION: Synthetic construct: methylated gene MINT21

<400> SEQUENCE: 21

| | | | | | |
|---|---|---|---|---|---|
| cccgggaact | acctaacgct | agttcagtcc | caaaatgctg | cccaacgaca | gaatgctcgc | 60 |
| ctccttgctt | cctctaacac | tctggcacac | ccacttggtg | tcgggcctct | atgggctcgc | 120 |
| agtgaagccc | tgagcctggg | ctgccccttc | ccatgtgccc | cctgccagcc | ggccctccct | 180 |
| cccttgggt | gccccatccc | tccagtcaac | tcctagccga | cccttaagag | tcaggtattt | 240 |
| gtagccttcc | ctgacatccc | tcccaggctg | tcccactgcc | agcaggacga | gcctgccct | 300 |
| cctccaccct | ccttacagct | atacctagcc | ttggccataa | tcactaatgg | accaggaaac | 360 |
| accctggcgc | gcagagccac | cgcaaagtgg | cccgctcagg | cccgcccggg | | 410 |

<210> SEQ ID NO 22
<211> LENGTH: 438
<212> TYPE: DNA
<213> ORGANISM: Artificial Sequence
<220> FEATURE:
<223> OTHER INFORMATION: Synthetic construct: methylated gene MINT22

```
<220> FEATURE:
<221> NAME/KEY: misc_feature
<222> LOCATION: (1)...(438)
<223> OTHER INFORMATION: n = A,T,C or G

<400> SEQUENCE: 22
cccggggatc tcagaaaggg aaggatgtgg ggagagtgaa ggtggaggca gtcacaccta      60
tcctggtgac cttggcgtgc ccccctggag tgacgagcca ggggcttata taggtgcgac    120
taggatgttg cctcgttttt cactcggggc tgcgaagagg gcattgctct ttctgatggc    180
tggaagacag gggcaaggag agagagaacc ggccccgaga cgggctggag ggtggggaca    240
ctggggagtt tggagctggg ggttcggagt gggaggtttg ggtcttctga gacgctccag    300
actctccgga ggcggcagag gtcgaggcag gaggcgaatg tgacgcttag ggtcgctacg    360
gttgatgttg ggcgcctttg gaagctggtc attaattctt gtcatcggga ggtttcgcgg    420
anggcgacag cgcccggg                                                  438

<210> SEQ ID NO 23
<211> LENGTH: 414
<212> TYPE: DNA
<213> ORGANISM: Artificial Sequence
<220> FEATURE:
<223> OTHER INFORMATION: Synthetic construct: methylated gene MINT23

<400> SEQUENCE: 23
cccgggcgcc cggccctggc tcgcggaatg ggcggccaga tctcaggccc tgcgtgcccg     60
agctcagtcc cagttccaac cggggtgcc catggactct cggagggcac tcctgggggg    120
acagctaaga caccaggctg caggatcact cattgcacgc tgcataatcg ccgccacaaa    180
ctctcccgtg cgcaagaaca aacgcgcgtg ggacagaaaa agttcctagg tctccgcagg    240
agtgaatgca aaatccaggg gactcagggt catgttggga gcccccttctc cccccgagag    300 tcagggagct gttgaggtgg gatcggtgag ggtcgcgcca cgcgggtccc ttccctacca    360
ggctcggata ccatgcagcg tggacactcc cgagttgctc tgcggaatcc cggg          414

<210> SEQ ID NO 24
<211> LENGTH: 523
<212> TYPE: DNA
<213> ORGANISM: Artificial Sequence
<220> FEATURE:
<223> OTHER INFORMATION: Synthetic construct: methylated gene MINT24
<220> FEATURE:
<221> NAME/KEY: misc_feature
<222> LOCATION: (1)...(523)
<223> OTHER INFORMATION: n = A,T,C or G

<400> SEQUENCE: 24
cccggggacg gggagggagg agggctgccg ggatgtgaac cggggaaggc agctggggct     60
ggagagcagc gcggaaaggg ggcccaggga gctggaaagc gagccaagag gagggcaagg    120
aaggtggcgg gctacgggga ggggaaagaa aaagggtgtc ttggcggtgg ccttggtaag    180 agaaagggc aagggtata attgacaagg cactgaaagt attgaagtca gagccttggg     240
aaggatctac cgaactctcg gcggtccacg cggggacaga cctcagcccg tgagccttga    300
gctccacgcg gggacagacc tcagcccgtg agccttgagc tccacgcggg gacagacctc    360
agcccgtgag ccttgagctc cacgcgggga cagacctcag cccgtgagcc ttgancccag    420
aaggagtggc aacctcanga cgtttgccaa gtggcctgga atgttangga aaccccagcc    480
ccgccaggaa cananctggc actaattccc ngctcggncc ggg                      523
```

```
<210> SEQ ID NO 25
<211> LENGTH: 399
<212> TYPE: DNA
<213> ORGANISM: Artificial Sequence
<220> FEATURE:
<223> OTHER INFORMATION: Synthetic construct: methylated gene MINT25

<400> SEQUENCE: 25
cccggggtgg gagctggctc gtgggggcgt gcgctgcgcg aaagcgaaag ccgcccgcca      60
gagcaacttt gcggcggaag gcgccgacga ggagctgtgc cgtgccgctc ttggggatgg     120
tgagctggcc gcccggccgg gtgggcagcg cgtccgggcg cggtgcttcg ctagctataa     180
ataggtgctg tgcggggaca ggaagatggt tccggccctt tacaagcacc ggcccgttat     240
gtgcgctggg ctaggacctt gccccgcagc ggagtgggag gagtgaggtt aggggtaacg     300
gttgcatggg atgggggtg gcacataga gcctacagca gagttggcgg cggggctctc      360
ccatgcactt ggttgtttgt cgtttctgct tttcccggg                            399

<210> SEQ ID NO 26
<211> LENGTH: 591
<212> TYPE: DNA
<213> ORGANISM: Artificial Sequence
<220> FEATURE:
<223> OTHER INFORMATION: Synthetic construct: methylated gene MINT26
<220> FEATURE:
<221> NAME/KEY: misc_feature
<222> LOCATION: (1)...(591)
<223> OTHER INFORMATION: n = A,T,C or G

<400> SEQUENCE: 26
cccgggctcc ggcatagctc tagattaacg agctgggcga cggggcgggg ggcagcatgc      60
ccagcgtcgg tgcacggccg gggttcttag acatcacaaa ctgtggagcg atacattgga     120
agcgaaatcc aagaacgaca ccggccggcg tgtttctgat gtagtcgtga ttagtgttgg     180
agatggccaa gggcggcttg cggagcccag ggaacgcagc gagccaggcc cgcgcccccc     240
tgcaaagctc tgccttgaac cacgtaattc aggcacccag ggtgtccctc cctaggtcct     300
ggccacattt cccgaaggtt attaaatgga gaattcagca gtggagttag agacggacga     360
atgtacagga agataagagg gaaactcttc ctcatttgct ttagggggtt gtgctgggaa     420
aatgcgggga ggttaaacaa agcttctcct angactccac gattcatttc taacaacttc     480
ttaaaagact cccgtctcng gagcagacgc ncccctcccg ctctctaagc cccgctgcat     540
gaaangatgc cctcggcccc ttgccagagg gccgggtccg ggattcccgg g              591

<210> SEQ ID NO 27
<211> LENGTH: 242
<212> TYPE: DNA
<213> ORGANISM: Artificial Sequence
<220> FEATURE:
<223> OTHER INFORMATION: Synthetic construct: methylated gene MINT27

<400> SEQUENCE: 27
cccgggatcc gggaaggctc ccccgagccg gggtcggaac tgcggctgga ggggcctcgg      60
cttgaggagg atctgggagg gcgggggctc agtcctggcc accaggtgtg aggggtcggg     120
tgcggagccc tgtgtcagac gcggcggtga aggctgtagc cctgctctcc gggatggggg     180
tggtactctc accgcaccct gccccaagcc gcagggagcc cctggcgccc ctggcgcccg     240
gg                                                                   242

<210> SEQ ID NO 28
<211> LENGTH: 463
```

```
<212> TYPE: DNA
<213> ORGANISM: Artificial Sequence
<220> FEATURE:
<223> OTHER INFORMATION: Synthetic construct: methylated gene MINT28
<220> FEATURE:
<221> NAME/KEY: misc_feature
<222> LOCATION: (1)...(463)
<223> OTHER INFORMATION: n = A,T,C or G

<400> SEQUENCE: 28
cccgggcccc tggcggggac accggggggg cgccggggge ctcccactta ttctacacct    60
ctcatgtctc ttcaccgtgc cagactagag tcaagctcaa cagggtcttc tttccccgct   120
gattccgcca agcccgttcc cttggctgtg gtttcgctgg atagtaggta gggacagtgg   180
gaatctcgtt catccattca tgcgcgtcac taattagatg acgaggcatt tggctacctt   240
aagagagtca tagttactcc cgccgtttac ccgcgcttac ttgaatttct tcactttgac   300
attcagagca ctgggcagaa atcacatcgc gtcaacaccc gccgcgggcc ttcgcgatgc   360
tttgttttaa ttaaacagtc ggattcccct ggtccgcacc agttctaagt cggctgctag   420
gcgccggccg angcgaagcg ccgcgcggaa ccgcgggccc ggg                     463

<210> SEQ ID NO 29
<211> LENGTH: 429
<212> TYPE: DNA
<213> ORGANISM: Artificial Sequence
<220> FEATURE:
<223> OTHER INFORMATION: Synthetic construct: methylated gene MINT29
<220> FEATURE:
<221> NAME/KEY: misc_feature
<222> LOCATION: (1)...(429)
<223> OTHER INFORMATION: n = A,T,C or G

<400> SEQUENCE: 29
cccgggagct gaccgtgggg aggccggttc cgctggtttc aaccagccca ctctcccctc    60
ttgggatgcc caaccccgcg tactcaccat ttcctggttt ccaggatgtc ctggcatctt   120
agctatgcat ttccagtacc tccagacctc agggcaacaa aggatgtgac aaagtcacct   180
agtgctcctg aggggcaaca cgcgggacag tagagatgga tctcaggctc cggcctgagc   240
cagagacaaa ggccgcgcca aacgctggaa gccacgccct cctccccaac tgcgtgcctg   300
ataggacggt tcctactctg acagattgaa taaggctcca ggaccctccc ccacacccac   360
cgtccccagc attagtgcgc tttatggaca gggaaacggg atcctgtang cggggtcaca   420
cgccccggg                                                          429

<210> SEQ ID NO 30
<211> LENGTH: 536
<212> TYPE: DNA
<213> ORGANISM: Artificial Sequence
<220> FEATURE:
<223> OTHER INFORMATION: Synthetic construct: methylated gene MINT30

<400> SEQUENCE: 30
cccgggcacc tgggctgggg gggcactcac atggctaccg gaggccccca cgtgcggcgc    60
cccgcggaga caggggttcg cgttcagagc tggtggcgga tggaccaggt ggccgcgggg   120
accagctggg tccagatgtg ctgggcctgc tggaagggga caggtgctac ctggacgtgt   180
aatggccctt ggtctctttt ggccgaacct gccgctccga tcccccctcca tcccttcatc   240 cctccatccc tccatccctc catccctccg gccttctctc ccttcttcct ccgctgcctg   300
tgttgcagag aggggctgtc agagactgtt gatgtggaa aaaatgaaat ggggaggggg   360
ttgtgattgg caaaggccag ttgtgccggg agcggtgggt agaggggtg ccctgagagt   420
```

```
gggaagccct aaacttggag ggcagcgctg atggggagag ggttcctggc accccacct     480 gccttggaag tgggaaatga catagcggga ggggggctgc agttccagcc cccggg        536
```

<210> SEQ ID NO 31
<211> LENGTH: 673
<212> TYPE: DNA
<213> ORGANISM: Artificial Sequence
<220> FEATURE:
<223> OTHER INFORMATION: Synthetic construct: methylated gene MINT31
<220> FEATURE:
<221> NAME/KEY: misc_feature
<222> LOCATION: (1)...(673)
<223> OTHER INFORMATION: n = A,T,C or G

<400> SEQUENCE: 31

```
cccggggcct ctatcctggc gggaagggca ggccgacccg gcagactgcg gcctctcggg     60
agggaagaag gtgtcagacg cgcggagcaa ccataaatag cccccctttc ccagaagacg    120
gcacggggtt caagactcag cgccgcata ctcagaatga gcagagac tcccgccagg      180 aaaaaagggc acttagggga tctgctcatt aacatgaaat gcaaatgagc ccgcccggcc    240
tcatttacac aactctgtgc atggattcgg cgaaagggca accagggaga cgacggcgca    300
gcagccactc tgccacttcc cccatcccct cccccccatc ggccggggcg ggaactgaga    360
cgaccccaac cctctgcggc ggcgggaggt gcgcggggc tgcgtgggtg gtgcagcctt     420 agggagtga acaacgccca ggggtgatgg cctcagcaaa gtgaggggtg gtgatggagg    480
tcatccgacc catcccgccg cctctccgca gtggcgcaag cgcccaaaaa tctccggaga    540
nggaactgag tgacccacta ggttccgccg tgtctacctc tcgcagatgt tggggaagtg     600
cttcccggcg tctaatcctc gctgttcccc cctccaccgg cgcccagcac accgcggcg     660 ctccgctccc ggg                                                       673
```

<210> SEQ ID NO 32
<211> LENGTH: 464
<212> TYPE: DNA
<213> ORGANISM: Artificial Sequence
<220> FEATURE:
<223> OTHER INFORMATION: Synthetic construct: methylated gene MINT32

<400> SEQUENCE: 32

```
cccgggtacc tgcacagctc gctccctccc atccttcggg tcttcgctcg aacgtccgct     60
cctcggtgag gccttccctg acaacgcat ttgaaacgta accccaaggc aagaagccac     120
cttccaggcg cgcagccgaa gcccagtgcc aaggaggccg gagactcggg tgcccgcgca    180
tcccgaaaac agcctctgag gggtcctctg agcatcctcc cagcgtgttt gggaggcaaa    240
ctcgttgact agctcttgag aggagtggct agaggaatcc aggcggggaa ggggacggtg    300
gactccagga gagtgtaatt tacaaaggcg ggggcgggg acgcccaggt ccagtcccca    360
ggactctgcg ccggacgctt cgcccgccct ttcaggtccc ctgcccggtc ctcgtacccg    420
cgcgggtccg gagaacctct gagcaccggc ccccagcccc cggg                     464
```

<210> SEQ ID NO 33
<211> LENGTH: 139
<212> TYPE: DNA
<213> ORGANISM: Artificial Sequence
<220> FEATURE:
<223> OTHER INFORMATION: Synthetic construct: methylated gene MINT33

<400> SEQUENCE: 33

```
cccgggcaga aaggctcgga tggcggtggc agaaaggctc ggaggcggtg gcctcagatc     60
```

```
cctggtccct ccgggtcact gtcggctaat tctgggggaa ggactgggca aggctgtttg      120
gaagaagtca gcgcccggg                                                   139

<210> SEQ ID NO 34
<211> LENGTH: 24
<212> TYPE: DNA
<213> ORGANISM: Artificial Sequence
<220> FEATURE:
<223> OTHER INFORMATION: Synthetic construct: oligonucleotide for PCR

<400> SEQUENCE: 34
agcactctcc agcctctcac cgac                                              24

<210> SEQ ID NO 35
<211> LENGTH: 12
<212> TYPE: DNA
<213> ORGANISM: Artificial Sequence
<220> FEATURE:
<223> OTHER INFORMATION: Synthetic construct: oligonucleotide for PCR

<400> SEQUENCE: 35
ccgggtcggt ga                                                           12

<210> SEQ ID NO 36
<211> LENGTH: 24
<212> TYPE: DNA
<213> ORGANISM: Artificial Sequence
<220> FEATURE:
<223> OTHER INFORMATION: Synthetic construct: oligonucleotide for PCR

<400> SEQUENCE: 36
ccaccgccat ccgagccttt ctgc                                              24

<210> SEQ ID NO 37
<211> LENGTH: 12
<212> TYPE: DNA
<213> ORGANISM: Artificial Sequence
<220> FEATURE:
<223> OTHER INFORMATION: Synthetic construct: oligonucleotide for PCR

<400> SEQUENCE: 37
ccgggcagaa ag                                                           12

<210> SEQ ID NO 38
<211> LENGTH: 24
<212> TYPE: DNA
<213> ORGANISM: Artificial Sequence
<220> FEATURE:
<223> OTHER INFORMATION: Synthetic construct: oligonucleotide for RDA

<400> SEQUENCE: 38
accgacgtcg actatccatg aacc                                              24

<210> SEQ ID NO 39
<211> LENGTH: 12
<212> TYPE: DNA
<213> ORGANISM: Artificial Sequence
<220> FEATURE:
<223> OTHER INFORMATION: Synthetic construct: oligonucleotide for RDA

<400> SEQUENCE: 39
ccggggttca tg                                                           12

<210> SEQ ID NO 40
<211> LENGTH: 24
```

```
<212> TYPE: DNA
<213> ORGANISM: Artificial Sequence
<220> FEATURE:
<223> OTHER INFORMATION: Synthetic construct: oligonucleotide for RDA

<400> SEQUENCE: 40
gtgagggtcg gatctggctg gctc                                             24

<210> SEQ ID NO 41
<211> LENGTH: 12
<212> TYPE: DNA
<213> ORGANISM: Artificial Sequence
<220> FEATURE:
<223> OTHER INFORMATION: Synthetic construct: oligonucleotide for RDA

<400> SEQUENCE: 41
ccgggagcca gc                                                          12

<210> SEQ ID NO 42
<211> LENGTH: 24
<212> TYPE: DNA
<213> ORGANISM: Artificial Sequence
<220> FEATURE:
<223> OTHER INFORMATION: Synthetic construct: oligonucleotide for RDA

<400> SEQUENCE: 42
aggcaactgt gctatccgag tgac                                             24

<210> SEQ ID NO 43
<211> LENGTH: 12
<212> TYPE: DNA
<213> ORGANISM: Artificial Sequence
<220> FEATURE:
<223> OTHER INFORMATION: Synthetic construct: oligonucleotide for RDA

<400> SEQUENCE: 43
ccgggtcact cg                                                          12

<210> SEQ ID NO 44
<211> LENGTH: 24
<212> TYPE: DNA
<213> ORGANISM: Artificial Sequence
<220> FEATURE:
<223> OTHER INFORMATION: Synthetic construct: oligonucleotide for RDA

<400> SEQUENCE: 44
gttagcggac acagggcggg tcac                                             24

<210> SEQ ID NO 45
<211> LENGTH: 12
<212> TYPE: DNA
<213> ORGANISM: Artificial Sequence
<220> FEATURE:
<223> OTHER INFORMATION: Synthetic construct: oligonucleotide for RDA

<400> SEQUENCE: 45
ccgggtgacc cg                                                          12

<210> SEQ ID NO 46
<211> LENGTH: 20
<212> TYPE: DNA
<213> ORGANISM: Artificial Sequence
<220> FEATURE:
<223> OTHER INFORMATION: Synthetic construct: oligonucleotide for PCR

<400> SEQUENCE: 46
aattaaccct cactaaaggg                                                  20
```

<210> SEQ ID NO 47
<211> LENGTH: 22
<212> TYPE: DNA
<213> ORGANISM: Artificial Sequence
<220> FEATURE:
<223> OTHER INFORMATION: Synthetic construct: oligonucleotide for PCR

<400> SEQUENCE: 47
gtaatacgac tcactatagg gc                                              22

<210> SEQ ID NO 48
<211> LENGTH: 23
<212> TYPE: DNA
<213> ORGANISM: Artificial Sequence
<220> FEATURE:
<223> OTHER INFORMATION: primer for PCR
<220> FEATURE:
<221> NAME/KEY: misc_feature
<222> LOCATION: (1)...(1)
<223> OTHER INFORMATION: y = C or T

<400> SEQUENCE: 48
ygttatgatt ttgtttagtt aat                                             23

<210> SEQ ID NO 49
<211> LENGTH: 23
<212> TYPE: DNA
<213> ORGANISM: Artificial Sequence
<220> FEATURE:
<223> OTHER INFORMATION: primer for PCR

<400> SEQUENCE: 49
tacaccaact acccaactac ctc                                             23

<210> SEQ ID NO 50
<211> LENGTH: 22
<212> TYPE: DNA
<213> ORGANISM: Artificial Sequence
<220> FEATURE:
<223> OTHER INFORMATION: primer for PCR
<220> FEATURE:
<221> NAME/KEY: misc_feature
<222> LOCATION: (7)...(7)
<223> OTHER INFORMATION: y = C or T

<400> SEQUENCE: 50
ttattaygtt ttttatgtga tt                                              22

<210> SEQ ID NO 51
<211> LENGTH: 22
<212> TYPE: DNA
<213> ORGANISM: Artificial Sequence
<220> FEATURE:
<223> OTHER INFORMATION: primer for PCR

<400> SEQUENCE: 51
accttctacc aattacttct tt                                              22

<210> SEQ ID NO 52
<211> LENGTH: 25
<212> TYPE: DNA
<213> ORGANISM: Artificial Sequence
<220> FEATURE:
<223> OTHER INFORMATION: primer for PCR

<400> SEQUENCE: 52
gctgcctatg aagatggatt tgagc                                           25

<210> SEQ ID NO 53
<211> LENGTH: 21
<212> TYPE: DNA
<213> ORGANISM: Artificial Sequence
<220> FEATURE:
<223> OTHER INFORMATION: primer for PCR

<400> SEQUENCE: 53
ggagttcccc cactgttgcc a                                              21

<210> SEQ ID NO 54
<211> LENGTH: 23
<212> TYPE: DNA
<213> ORGANISM: Artificial Sequence
<220> FEATURE:
<223> OTHER INFORMATION: primer for PCR

<400> SEQUENCE: 54
cggagtcaac ggattggtcg tat                                            23

<210> SEQ ID NO 55
<211> LENGTH: 24
<212> TYPE: DNA
<213> ORGANISM: Artificial Sequence
<220> FEATURE:
<223> OTHER INFORMATION: primer for PCR

<400> SEQUENCE: 55
agccttctcc atggtggtga agac                                           24

<210> SEQ ID NO 56
<211> LENGTH: 22
<212> TYPE: DNA
<213> ORGANISM: Artificial Sequence
<220> FEATURE:
<223> OTHER INFORMATION: primer for PCR
<220> FEATURE:
<221> NAME/KEY: misc_feature
<222> LOCATION: (8)...(8)
<223> OTHER INFORMATION: y = C or T

<400> SEQUENCE: 56
tagtagtygt tttagggagg ga                                             22

<210> SEQ ID NO 57
<211> LENGTH: 25
<212> TYPE: DNA
<213> ORGANISM: Artificial Sequence
<220> FEATURE:
<223> OTHER INFORMATION: primer for PCR
<220> FEATURE:
<221> NAME/KEY: misc_feature
<222> LOCATION: (15)...(15)
<223> OTHER INFORMATION: r = G or A

<400> SEQUENCE: 57
tctaaatact caacraaaat acctt                                          25

<210> SEQ ID NO 58
<211> LENGTH: 21
<212> TYPE: DNA
<213> ORGANISM: Artificial Sequence
<220> FEATURE:
<223> OTHER INFORMATION: primer for PCR

<400> SEQUENCE: 58
gggttggaga gtaggggagt t                                              21

```
<210> SEQ ID NO 59
<211> LENGTH: 26
<212> TYPE: DNA
<213> ORGANISM: Artificial Sequence
<220> FEATURE:
<223> OTHER INFORMATION: primer for PCR
<220> FEATURE:
<221> NAME/KEY: misc_feature
<222> LOCATION: (18)...(18)
<223> OTHER INFORMATION: r = G or A

<400> SEQUENCE: 59
ccatctaaaa ttacctcrat aactta                                              26
```